(12) United States Patent
Gross et al.

(10) Patent No.: US 7,105,032 B2
(45) Date of Patent: Sep. 12, 2006

(54) AGENTS USED FOR DYEING KERATINOUS FIBERS

(75) Inventors: Wibke Gross, Duesseldorf (DE);
Sandra Mausberg, Erkrath (DE);
Horst Hoeffkes, Duesseldorf (DE);
Doris Oberkobusch, Duesseldorf (DE)

(73) Assignee: Henkel Kommanditgesellschaft auf Aktien (Henkel KGaA), Duesseldorf (DE)

( * ) Notice: Subject to any disclaimer, the term of this patent is extended or adjusted under 35 U.S.C. 154(b) by 0 days.

(21) Appl. No.: 11/069,745

(22) Filed: Mar. 1, 2005

(65) Prior Publication Data

US 2005/0144740 A1 Jul. 7, 2005

Related U.S. Application Data

(63) Continuation of application No. PCT/EP03/09366, filed on Aug. 23, 2003.

(30) Foreign Application Priority Data

Sep. 5, 2002 (DE) ................. 102 41 076

(51) Int. Cl.
*A61K 7/13* (2006.01)
(52) U.S. Cl. ............... 8/405; 8/406; 8/407; 8/408; 8/409; 8/575; 8/576; 8/607; 8/608; 544/242
(58) Field of Classification Search .............. 8/405, 8/406, 407, 408, 409, 575, 576, 607, 608; 546/298; 544/242
See application file for complete search history.

(56) References Cited

U.S. PATENT DOCUMENTS

| | | | |
|---|---|---|---|
| 3,574,200 A | 4/1971 | Brack ................. | 286/240 |
| 4,865,774 A | 9/1989 | Fabry et al. ........... | 252/554 |
| 4,931,218 A | 6/1990 | Schenker et al. ....... | 282/554 |
| 5,061,289 A | 10/1991 | Clausen et al. ........ | 8/405 |
| 5,279,616 A | 1/1994 | Lang et al. ........... | 8/406 |
| 5,294,726 A | 3/1994 | Behler et al. ......... | 554/98 |
| 5,380,340 A | 1/1995 | Neunhoeffer et al. .... | 8/409 |
| 5,534,267 A | 7/1996 | Neunhoeffer et al. .... | 424/701 |
| 5,663,366 A | 9/1997 | Neunhoeffer et al. .... | 548/371.4 |
| 5,725,607 A | 3/1998 | Giera et al. .......... | 8/654 |
| 5,766,576 A | 6/1998 | Lowe et al. .......... | 424/62 |
| 6,099,592 A | 8/2000 | Vidal et al. .......... | 8/409 |
| 6,284,003 B1 | 9/2001 | Rose et al. ........... | 8/412 |
| 6,635,090 B1 | 10/2003 | Andrean et al. ....... | 8/405 |

FOREIGN PATENT DOCUMENTS

| | | |
|---|---|---|
| CA | 2 288 253 | 5/2000 |
| DE | 2 047 431 | 3/1972 |
| DE | 2047431 A * | 3/1972 |
| DE | 2 165 913 | 7/1973 |
| DE | 23 59 399 A1 | 6/1975 |
| DE | 37 23 354 A1 | 1/1989 |
| DE | 37 25 030 A1 | 2/1989 |
| DE | 38 43 892 A1 | 6/1990 |
| DE | 39 26 344 A1 | 2/1991 |
| DE | 41 33 957 A1 | 4/1993 |
| DE | 195 43 988 A1 | 5/1997 |
| DE | 299 08 573 U1 | 9/1999 |
| DE | 101 48 847 A1 | 4/2003 |
| EP | 0 740 931 B1 | 8/1997 |
| EP | 0 873 745 A2 | 10/1998 |
| EP | 0 998 908 A2 | 5/2000 |
| FR | 2 787 707 A1 | 6/2000 |
| GB | 1 026 978 | 4/1966 |
| GB | 1 153 196 | 5/1969 |
| GB | 1 386 269 | 3/1975 |
| GB | 1 486 576 | 9/1977 |
| JP | 02-019576 | 1/1990 |
| JP | 2002-47153 A1 | 2/2002 |
| WO | WO 94/08969 A1 | 4/1994 |
| WO | WO 94/08970 A1 | 4/1994 |
| WO | WO 95/15144 A1 | 6/1995 |
| WO | WO 96/15765 A1 | 5/1996 |

OTHER PUBLICATIONS

John C. et al. "CHEMISTRY".*
English Abstract of DE 2047431 A1.*
Hans Baumann et al., "Reaktionen der Methylenbased von Oxazolidinoen und Pyrimidonen" Justus Liebigs Annalen der Chemie, vol. 717, pp. 124-136 XP002265004 (1968).
Charles Zviak, "Hair Coloring", The Science of Hair Care, Chapter 7, vol. 7, Dermatology, Marcel Dekker Inc., pp. 235-261 (1986).
Charles Zviak, "Oxidation Coloring", The Science of Hair Care, Chapter 8, vol. 7, Dermatolo Marcel Dekker Inc., pp. 263-286 (1986).
EU Inventory of Cosmetic Ingredients, Colipa, (1996) on diskette.
D. Lloyd et al., "Studies of 2-Oxo-and 2-Thioxo-1,3-diydropyrimidiuium Salts", Journal Chem. Soc. Perksin Trans I, vol. 16, pp. 1862-1869 (1977).
S. T. Oswald et al., "Synthesis of 1,3-Diaklyl-1,2-dihydro-2-oxopyrimidinium Salts by Direct Cyclization", Journal Heterocycl. Chem, vol. 11(3), pp. 441-443 (1974).
V. A. Chuiguk, "1,3-Diaryl-1,2-Dihydro-2-Oxopyrimidinium Salts and Methine Dyes Based on Them", Ukr. Khim, Zh (Russ Ed.), vol. 48(11), pp. 1220-1223 (1982).

* cited by examiner

Primary Examiner—Eisa Elhilo
(74) Attorney, Agent, or Firm—John S. Child, Jr.

(57) ABSTRACT

A composition for dyeing keratin-containing fibers, particularly human hair, comprising 1,2-dihydropyrimidinium derivatives in combination with reactive carbonyl compounds and methods of employing this combination for dyeing keratin-containing fibers, for color restoration or shading keratin-containing fibers that are already dyed.

41 Claims, No Drawings

AGENTS USED FOR DYEING KERATINOUS FIBERS

CROSS REFERENCE TO RELATED APPLICATIONS

This application is a continuation under 35 U.S.C. § 365 and 35 U.S.C. § 120 of international application PCT/EP2003/009366, filed on Aug. 23, 2003. This application also claims priority under 35 U.S.C. § 119 of DE 102 41 076.3, filed Sep. 5, 2002, which is incorporated herein by reference in its entirety.

BACKGROUND OF THE INVENTION

The invention relates to an agent for dyeing (coloring) keratin-containing fibers, particularly human hair, comprising 1,2-dihydropyrimidinium derivatives in combination with reactive carbonyl compounds, the use of this combination in compositions for dyeing keratin-containing fibers, for color restoration or shading keratin-containing fibers that are already dyed, as well as a process for dyeing keratin-containing fibers, particularly human hair.

For dyeing keratin-containing fibers, generally either substantive dyestuffs or oxidation dyestuffs are used, the latter resulting from oxidative coupling of one or more developer components with each other or with one or more coupler components. Coupler and developer components are also referred to as oxidation dyestuff precursors.

Usually, primary aromatic amines with a further free or substituted hydroxyl or amino group in the para or ortho position, diaminopyridine derivatives, heterocyclic hydrazones, 4-aminopyrazolone derivatives as well as 2,4,5,6-tetraminopyrimidine and its derivatives are employed as developer components.

Specific representatives are for example p-phenylenediamine, p-toluylenediamine, 2,4,5,6-tetraminopyrimidine, p-aminophenol, N,N-bis-(2-hydroxyethyl)-p-phenylenediamine, 2-(2,5-diaminophenyl)ethanol, 2-(2,5-diaminophenoxy)ethanol, 1-phenyl-3-carboxyamido-4-aminopyrazol-5-one, 4-amino-3-methylphenol, 2-aminomethyl-4-aminophenol, 2-hydroxymethyl-4-aminophenol, 2-hydroxy-4,5,6-triaminopyrimidine, 2,4-dihydroxy-5,6-diaminopyrimidine and 2,5,6-triamino-4-hydroxypyrimidine.

Generally, m-phenylenediamine derivatives, naphthols, resorcinol and resorcinol derivatives, pyrazolones, m-aminophenols and substituted pyridine derivatives. Suitable coupler substances are particularly α-naphthol, 1,5-, 2,7- and 1,7-dihydroxynaphthalene, 5-amino-2-methylphenol, m-aminophenol, resorcinol, resorcinol monomethylether, m-phenylenediamine, 2,4-diaminophenoxyethanol, 2-amino-4-(2-hydroxyethylamino)anisole (Lehmann's Blue), 1-phenyl-3-methylpyrazol-5-one, 2,4-dichloro-3-aminophenol, 1,3-bis-(2,4-diaminophenoxy)propane, 2-chlororesorcinol, 4-chlororesorcinol, 2-chloro-6-methyl-3-aminophenol, 2-methylresorcinol, 5-methylresorcinol, 3-amino-6-methoxy-2-methylaminopyridine and 3,5-diamino-2,6-dimethoxypyridine are employed as coupler components.

With respect to other customary dyestuff components, reference is expressly made to the series "Dermatology", edited by Ch. Culnan, H. Maibach, publisher Marcel Dekker Inc., New York, Basel, 1986, vol. 7, Ch. Zviak, The Science of Hair Care, ch. 7, pages 248–250 (substantive dyestuffs), and ch. 8, pages 264–267 (oxidation dyestuffs) and the "European Inventory of Cosmetic Raw Materials", 1996, published by the European Commission, obtainable as a floppy disk from the Bundesverband der deutschen Industrie-und Handelsunternehmen für Arzneimittel, Reformwaren und Körperpflegemittel e.V., Mannheim.

Although intense colorations with good fastness properties can be obtained with oxidation dyestuffs, the development of the color generally occurs however, under the influence of oxidizing agents such as e.g. $H_2O_2$, which in some cases can result in damage to the fibers. The preparation of oxidation hair colorations in the reddish range with satisfactory fastness properties still proves to be problematic, particularly for very good wash fastness and rubbing fastness. Furthermore, some oxidation dyestuff precursors or particular mixtures of oxidation dyestuff precursors can sometimes produce a sensitizing effect on persons with sensitive skin. Substantive dyestuffs are applied under milder conditions but have the disadvantage that the colorations often suffer from inadequate fastness properties.

Colorants comprising 1,2-dihydropyrimidinium derivatives, together with their use for dyeing keratin-containing fibers or for color restoration or shading keratin-containing fibers that have already been dyed, are so far unknown.

Reactions of pyrimidones as methylene bases are described in the publication of H. Baumann et al., Liebigs Ann. Chem., 1968, 717, 124–136. A hair colorant comprising 1,2-dihydropyrimidinium derivatives, or the use of the disclosed hemicyanines for dyeing keratin-containing fibers is not suggested.

In the German patent application DE-A1-2047431, cationic methine dyestuffs are described for the coloration of anionically modified fibers such as acid modified polyesters or acrylonitrile polymers. For the synthesis of cationic methine dyestuffs, 3,4-dihydro-3-methyl-4-methylenequinazol-2-one and 1,3,6-trimethyl-4-methylenepyrimidine-2-one inter alia are used as well as imperatively terephthalaldehyde.

In the German patent application DE-A1-2165913, a process for the manufacture of bleached images by using light-sensitive dyestuffs is proposed. The claimed light-sensitive dyestuffs belong to the class of pyrimidone or thiopyrimidone dyestuffs.

The object of the present invention is to provide colorants for keratin-containing fibers, particularly human hair, which with respect to depth of color, gray coverage and fastness properties such as for example light-, rubbing- and wash fastness as well as perspiration fastness and cold-waving fastness, are qualitatively at least equal, particularly in the reddish range, to typical oxidation hair colorants, without however being necessarily dependent on oxidizing agents such as for example $H_2O_2$. Moreover, the dyes must not possess any, or only a very low degree of sensitization.

SUMMARY OF THE INVENTION

Surprisingly it has now been found that 1,2-dihydropyrimidinium derivatives in combination with compounds comprising at least one reactive carbonyl group, are outstandingly suitable for dyeing keratin-containing fibers—even in the absence of oxidizing agents. They provide colorations with outstanding brilliance and depth of color and lead to many color shades. In particular, colorations with improved fastness properties are obtained across a range of shades from yellow through yellow-brown, orange, brown-orange, brown, red, red-violet to blue-violet and black. The addition of oxidizing agents should not necessarily be excluded, however.

DETAILED DESCRIPTION OF THE INVENTION

The subject of the invention is an agent for dyeing keratin-containing fibers, particularly human hair, comprising at least one 1,2-dihydropyrimidinium derivative according to Formula 1 and/or its enamine form,

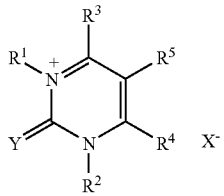

(I)

wherein
- $R^1$ and $R^2$ independently of one another stand for a linear or cyclic $C_1$–$C_6$ alkyl group, a $C_2$–$C_6$ alkenyl group, an optionally substituted aryl group, an optionally substituted heteroaryl group, an aryl $C_1$–$C_6$ alkyl group, a $C_1$–$C_6$ hydroxyalkyl group, a $C_2$–$C_6$ polyhydroxyalkyl group, a $C_1$–$C_6$ alkoxy-$C_1$–$C_6$ alkyl group, a group $R^I R^{II} N$—$(CH_2)_m$— in which $R^I$ and $R^{II}$ independently of one another stand for a hydrogen atom, a $C_1$–$C_4$ alkyl group, a $C_1$–$C_4$ hydroxyalkyl group or an aryl $C_1$–$C_6$ alkyl group, wherein $R^I$ and $R^{II}$ together with the nitrogen atom can form a 5-, 6-, or 7-membered ring, and m stands for a number 2, 3, 4, 5 or 6.
- $R^3$ and $R^4$ independently of one another stand for a hydrogen atom or a $C_1$–$C_6$ alkyl group, wherein at least one of the radicals $R^3$ and $R^4$ means a $C_{1-6}$ alkyl group,
- $R^5$ stands for a hydrogen atom, a $C_1$–$C_6$-alkyl group, a $C_1$–$C_6$ hydroxyalkyl group, a $C_2$–$C_6$ polyhydroxyalkyl group, a $C_1$–$C_6$ alkoxy group, a $C_1$–$C_6$ hydroxyalkoxy group, a group $R^{III} R^{IV} N$—$(CH_2)_q$-, in which $R^{III}$ and $R^{IV}$ stand independently of one another for a hydrogen atom, a $C_1$–$C_6$ alkyl group, a $C_1$–$C_6$ hydroxyalkyl group or an aryl $C_1$–$C_6$ alkyl group, and q stands for a number 1, 2, 3, 4, 5 or 6, wherein the radical $R^5$ together with one of the radicals $R^3$ or $R^4$ can form a 5- or 6-membered aromatic or aliphatic ring that can be optionally substituted with a halogen atom, a $C_1$–$C_6$ alkyl group, a $C_1$–$C_6$ hydroxyalkyl group, a $C_2$–$C_6$ polyhydroxyalkyl group, a $C_1$–$C_6$ alkoxy group, a $C_1$–$C_6$ hydroxyalkoxy group, a nitro group, a hydroxyl group, a group $R^V R^{VI} N$—$(CH_2)_s$—, in which $R^V$ and $R^{VI}$ independently of one another stand for a hydrogen atom, a $C_1$–$C_6$ alkyl group, a $C_1$–$C_6$ hydroxyalkyl group or an aryl $C_1$–$C_6$ alkyl group, and s stands for a number 0, 1, 2, 3, 4, 5 or 6,
- Y stands for an oxygen atom, a sulfur atom or a group $NR^{VII}$, in which $R^{VII}$ stands for a hydrogen atom, an aryl group, a heteroaryl group, a $C_1$–$C_6$ alkyl group or a $C_1$–$C_6$ arylalkyl group,
- $X^-$ stands for halide, benzenesulfonate, p-toluenesulfonate, $C_1$–$C_4$ alkanesulfonate, trifluoromethanesulfonate, perchlorate, 0.5 sulfate, hydrogen sulfate, tetrafluoroborate, hexafluorophosphate or tetrachlorozincate, and at least one compound with a reactive carbonyl group (component B).

In a preferred embodiment, Y stands for an oxygen or a sulfur atom, particularly preferably for an oxygen atom.

Preferably, $X^-$ stands for a halide, particularly chloride, bromide or iodide, p-toluenesulfonate, tetrafluoroborate, trifluoromethanesulfonate, hexafluorophosphate, 0.5 sulfate or hydrogen sulfate. The anions chloride, bromide, iodide, hydrogen sulfate or p-toluenesulfonate are particularly preferred for use as $X^-$.

$R^5$ stands preferably for a hydrogen atom.

At least one group $R^3$ or $R^4$ according to Formula I stands for a $C_1$–$C_6$ alkyl group. This alkyl group carries on its α-carbon atom preferably at least two hydrogen atoms. Particularly preferred alkyl groups are methyl, ethyl, propyl, n-butyl, iso-butyl, n-pentyl, iso-pentyl, n-hexyl. Quite particularly preferred is when $R^3$ and $R^4$ independently of one another stand for hydrogen or a methyl group, wherein at least one group $R^3$ or $R^4$ means a methyl group.

Preferably the compounds according to Formula I are selected from the group consisting of 1,2-dihydro-1,3,4,6-tetramethyl-2-oxo-pyrimidinium chloride, 1,2-dihydro-1,3-diethyl-4,6-dimethyl-2-oxo-pyrimidinium chloride, 1,2-dihydro-1,3-dipropyl-4,6-dimethyl-2-oxo-pyrimidinium chloride, 1,2-dihydro-1,3-di(2-hydroxyethyl)-4,6-dimethyl-2-oxo-pyrimidinium chloride, 1,2-dihydro-1,3-diphenyl-4,6-dimethyl-2-oxo-pyrimidinium chloride, 1,2-dihydro-1,3,4,6-tetramethyl-2-oxo-pyrimidinium hydrogen sulfate, 1,2-dihydro-1,3-diethyl-4,6-dimethyl-2-oxo-pyrimidinium hydrogen sulfate, 1,2-dihydro-1,3-dipropyl-4,6-dimethyl-2-oxo-pyrimidinium hydrogen sulfate, 1,2-dihydro-1,3-di(2-hydroxyethyl)-4,6-dimethyl-2-oxo-pyrimidinium hydrogen sulfate, 1,2-dihydro-1,3-diphenyl-4,6-dimethyl-2-oxo-pyrimidinium hydrogen sulfate, 1,2-dihydro-1,3,4-trimethyl-2-oxo-pyrimidinium chloride, 1,2-dihydro-1,3,4-trimethyl-2-oxo-pyrimidinium hydrogen sulfate, 1,2-dihydro-1,3-diethyl-4-methyl-2-oxo-pyrimidinium chloride, 1,2-dihydro-1,3-diethyl-4-methyl-2-oxo-pyrimidinium hydrogen sulfate, 1,2-dihydro-1,3-dipropyl-4-methyl-2-oxo-pyrimidinium chloride, 1,2-dihydro-1,3-dipropyl-4-methyl-2-oxo-pyrimidinium hydrogen sulfate, 1,2-dihydro-1,3-di(2-hydroxyethyl)-4-methyl-2-oxo-pyrimidinium chloride, 1,2-dihydro-1,3-di(2-hydroxyethyl)-4-methyl-2-oxo-pyrimidinium hydrogen sulfate, 1,2-dihydro-1,3-diphenyl-4-methyl-2-oxo-pyrimidinium chloride, 1,2-dihydro-1,3-diphenyl-4-methyl-2-oxo-pyrimidinium hydrogen sulfate, 1,2-dihydro-1,3,4,5,6-pentamethyl-2-oxo-pyrimidinium chloride, 1,2-dihydro-1,3,4,6-tetramethyl-2-thioxo-pyrimidinium chloride, 1,2-dihydro-1,3-diethyl-4,6-dimethyl-2-thioxo-pyrimidinium chloride, 1,2-dihydro-1,3-dipropyl-4,6-dimethyl-2-thioxo-pyrimidinium chloride, 1,2-dihydro-1,3-di(2-hydroxyethyl)-4,6-dimethyl-2-thioxo-pyrimidinium chloride, 1,2-dihydro-1,3-diphenyl-4,6-dimethyl-2-thioxo-pyrimidinium chloride, 1,2-dihydro-1,3,4,6-tetramethyl-2-thioxo-pyrimidinium hydrogen sulfate, 1,2-dihydro-1,3-dipropyl-4,6-dimethyl-2-thioxo-pyrimidinium hydrogen sulfate, 1,2-dihydro-1,3-di(2-hydroxyethyl)-4,6-dimethyl-2-thioxo-pyrimidinium hydrogen sulfate, 1,2-dihydro-1,3-diphenyl-4,6-dimethyl-2-thioxo-pyrimidinium hydrogen sulfate, 1,2-dihydro-1,3,4-trimethyl-2-thioxo-pyrimidinium chloride, 1,2-dihydro-1,3,4-trimethyl-2-thioxo-pyrimidinium hydrogen sulfate, 1,2-dihydro-1,3-diethyl-4-methyl-2-thioxo-pyrimidinium chloride, 1,2-dihydro-1,3-diethyl-4-methyl-2-thioxo-pyrimidinium hydrogen sulfate, 1,2-dihydro-1,3-dipropyl-4-methyl-2-thioxo-pyrimidinium chloride, 1,2-dihydro-1,3-dipropyl-4-methyl-2-thioxo-pyrimidinium hydrogen sulfate, 1,2-dihydro-1,3-di(2-hydroxyethyl)-4-methyl-2-thioxo-pyrimidinium chloride, 1,2-dihydro-1,3-di(2-hydroxyethyl)-4-methyl-2-thioxopyrimidinium hydrogen sulfate, 1,2-dihydro-1,3-diphenyl-4-methyl-2-thioxo-pyrimidinium chloride, 1,2-dihydro-1,3-diphenyl-4-methyl-2-thioxo-pyrimidinium hydrogen sulfate, 1,2-dihydro-3,4-dimethyl-2-oxo-quinazolinium chloride, 1,2-dihydro-3,4-dimethyl-2-oxo-quinazolinium p-toluenesulfonate, 1,2-dihydro-3,4-dimethyl-2-thioxo-quinazolinium chloride, 1,2-dihydro-3,4-dimethyl-2-thioxo-quinazolinium p-toluenesulfonate, 1,2-dihydro-1,3,4-trimethyl-2-thioxo-quinazolinium hydrogen sulfate, 1,3,4-trimethyl-2-oxo-2,3,5,6,7,8-hexahydroquinolinium hydrogen sulfate, 1,3,4-trimethyl-2-thioxo-2,3,5,6,7,8-hexahydroquinolinium hydrogen sulfate, 1,3,4-trimethyl-2-oxo-3,5,6,7-tetrahydro-2H-cyclopenta[a]pyrimidinium hydrogen sulfate and 1,3,4-trimethyl-2-thioxo-3,5,6,7-tetrahydro-2H-cyclopenta[a]pyrimidinium hydrogen sulfate.

Quite particularly preferred inventive compounds according to Formula I of component A are selected from 1,2-dihydro-1,3,4,6-tetramethyl-2-oxopyrimidinium chloride, 1,2-dihydro-1,3,4,6-tetramethyl-2-oxopyrimidinium hydrogen sulfate, 1,2-dihydro-1,3,4-trimethyl-2-oxopyrimidinium chloride, 1,2-dihydro-4,6-dimethyl-1,3-dipropyl-2-oxopyrimidinium chloride, 1,2-dihydro-1,3,4,6-tetramethyl-2-thioxopyrimidinium hydrogen sulfate and 1,2-dihydro-1,3,4,5,6-pentamethyl-2-oxopyrimidinium chloride.

In the following should be mentioned examples of groups or radicals cited as substituents in the context of this application. Examples of $C_1$–$C_6$ alkyl radicals are the groups methyl, ethyl, propyl, isopropyl, n-butyl, sec-butyl and tert-butyl, n-pentyl and n-hexyl. Preferred alkyl radicals are propyl, methyl and ethyl. Examples of appropriate cyclic alkyl groups are cyclopentyl and cyclohexyl. Examples of $C_2$–$C_6$ alkenyl radicals are vinyl and allyl. According to the invention, preferred exemplary $C_1$–$C_6$ alkoxy radicals are a methoxy or ethoxy group. The methoxycarbonyl-ethoxycarbonyl-n-propoxycarbonyl-, isopropoxycarbonyl-, n-butoxycarbonyl-, sec-butoxycarbonyl- and tert-butoxycarbonyl are examples of $C_1$–$C_4$ alkoxycarbonyl groups; the methoxycarbonyl and ethoxycarbonyl groups are here particularly preferred. In addition, preferred examples of a $C_1$–$C_6$ hydroxyalkyl group can be cited as hydroxymethyl-, 2-hydroxyethyl-, 2-hydroxypropyl-, 3-hydroxypropyl-, 4-hydroxybutyl-, 5-hydroxypentyl- and a 6-hydroxyhexyl group. A 2-hydroxyethyl group is particularly preferred. The methoxyethyl-, ethoxyethyl-, methoxypropyl-, methoxybutyl-, ethoxybutyl- and the methoxyhexyl group are examples of inventive $C_1$–$C_6$ alkoxy $C_1$–$C_6$ alkyl groups. Examples of a $C_2$–$C_6$ polyhydroxyalkyl group are the 2,3-dihydroxypropyl group, 3,4-dihydroxybutyl group and the 2,4-dihydroxybutyl group. A preferred hydroxy $C_1$–$C_6$ alkoxy group is the 2-hydroxyethoxy group. Preferred aryl groups are phenyl, naphthyl and biphenyl. Examples of halogen atoms are F—, Cl—, Br— or I atoms, wherein Cl atoms are quite particularly preferred. Preferred aryl $C_1$–$C_6$ aminoalkyl groups are benzyl and 2-phenylethyl. The aminomethyl-, 2-aminoethyl-, 3-aminopropyl-, 2-dimethylaminoethyl-, diethylaminomethyl-, dimethylaminomethyl-, 2-methylaminoethyl-, dimethylamino-, piperidinomethyl-, pyrrolidinomethyl-, morpholinomethyl- and the amino group are examples of a group R'R''N—(CH$_2$)$_m$— wherein the diethylaminomethyl-, piperidinomethyl-, 2-dimethylaminoethyl-, dimethylamino- and the amino group are particularly preferred. Examples of a heteroaryl group are pyrrolidyl, 2-furyl, 2-thienyl, 4-pyridyl, 3-pyridyl, 2-pyridyl, triazolyl and 1-imidazolyl. Examples of a heterocycle ($C_{1-4}$)alkyl group are pyrrolidino-($C_{1-4}$)alkyl, piperidino-($C_{1-4}$)alkyl, morpholino-($C_{1-4}$)alkyl, 2-furyl-($C_{1-4}$) alkyl, 2-thienyl-($C_{1-4}$) alkyl, 4-pyridyl-($C_{1-4}$)alkyl, 3-pyridyl-($C_{1-4}$)alkyl, 2-pyridyl-($C_{1-4}$)alkyl, triazolyl-($C_{1-4}$)alkyl, and 1-imidazolyl-($C_{1-4}$)alkyl. A preferred ($C_{1-4}$) carboxyalkyl group is the 3-carboxypropyl group. Particularly preferred $C_2$–$C_6$ alkenylene groups are vinylene and propylene. A particularly preferred $C_4$–$C_6$ alkadienylene group is the 1,3-butadien-1,4-diyl group. The groups 1-carboxypropylene and 1-carboxyethylene are preferred carboxy $C_1$–$C_4$ alkylene groups. According to the invention, the subsequently used terms are derived from the definitions given here.

The inventive 1,2-dihydropyrimidinium derivatives according to Formula I are CH-acid compounds. They exist in chemical equilibrium with the enamine form of the 1,2-dihydropyrimidinium derivatives according to Formula I. The corresponding enamines can be specifically synthesized from the compounds of Formula I by the use of a base for deprotonation at the α-carbon atom of the $C_1$–$C_6$ alkyl radical $R^3$ or $R^4$. An example of this deprotonation is illustrated here below, wherein for clarity, the radical R—CH$_2$— was chosen as $R^3$. A compound according to Formula Ia is an example of an inventive enamine form of the 1,2-dihydropyrimidinium derivative.

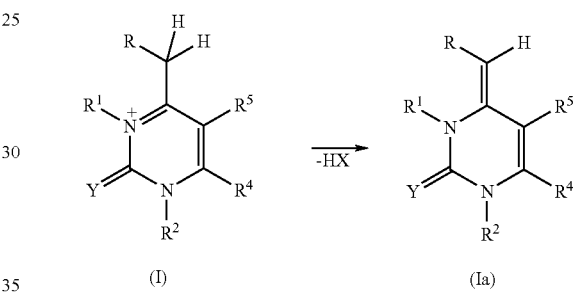

By keratin-containing fibers should be understood wool, fur, feathers and particularly human hair. In principal however, the inventive colorants can also be used for dyeing other natural fibers such as, for example, cotton, jute, sisal, linen or silk, modified natural fibers such as, for example, regenerated cellulose, nitro-, alkyl- or hydroxyalkyl- or acetyl cellulose.

The majority of 1,2-dihydropyrimidinium derivatives according to Formula I are known from the literature, are commercially available or synthesizable by known synthetic processes according to D. Lloyd et al., J. Chem. Soc. Perkin Trans I, 1977, 16, 1862–1869; S. T. Oswald et al., J. Heterocycl. Chem., 1974, 11(3), 441–443; H. Baumann et al., Liebigs Ann. Chem., 1968, 717, 124–136 and V. A. Chuiguk, Ukr. Khim.Zh. (RussEd.), 1982, 48 (11), 1220–1223.

Colorations with increased brilliance and improved fastness properties (fastness to light, washing fastness, fastness to rubbing) over a broad range of shades are obtained if the compounds of Formula I according to the invention, together with at least one substance with a reactive carbonyl group (subsequently referred to as component B or reactive carbonyl compound) are comprised in the inventive agents. Inventive reactive carbonyl compounds possess at least one carbonyl group as the reactive group that reacts with the CH-acid compound according to Formula I with the formation of a carbon-carbon bond. Moreover, those compounds in which the reactive carbonyl group is derivatized in such a manner that the reactivity of the carbon atom of the derivatized carbonyl group towards the CH-acid compounds of Formula I is still present, are also usable according to the invention. These derivatives are preferably addition compounds of a) amines and their derivatives forming imines or oximes as the addition compounds b) alcohols forming acetals or ketals as the addition compound on the carbon atom of the carbonyl group of the reactive carbonyl compound.

Component B is preferably selected from compounds according to Formula II,

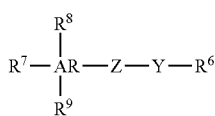

(II)

wherein

AR stands for benzene, naphthalene, pyridine, pyrimidine, pyrazine, pyridazine, carbazole, pyrrole, pyrazole, furan, thiophene, 1,2,3-triazine, 1,3,5-triazine, quinoline, isoquinoline, indole, indoline, indolizine, indane, imidazole, 1,2,4-triazole, 1,2,3-triazole, tetrazole, benzimidazole, 1,3-thiazole, benzothiazole, indazole, benzoxazole, quinoxaline, quinazoline, quinolizine, cinnoline, acridine, julolidine, acenaphthene, fluorene, biphenyl, diphenylmethane, benzophenone, diphenyl ether, azobenzene, chromone, coumarine, diphenylamine, stilbene, wherein the N-heteroaromatics can also be quaternized, $R^6$ stands for a hydrogen atom, a $C_1$–$C_6$ alkyl, $C_2$–$C_6$ acyl, $C_2$–$C_4$ alkenyl, $C_1$–$C_4$ perfluoroalkyl, an optionally substituted aryl or heteroaryl group, $R^7$, $R^8$ and $R^9$ independently from one another stand for a hydrogen atom, a halogen atom, a $C_1$–$C_6$ alkyl, $C_1$–$C_6$ alkoxy, $C_1$–$C_6$ aminoalkyl, $C_1$–$C_6$ hydroxyalkyl group, a $C_1$–$C_6$ alkoxy-$C_1$–$C_6$ alkyloxy group, a $C_2$–$C_6$ acyl group, an acetyl, a carboxyl, carboxylato, carbamoyl, sulfo, sulfato, sulfonamide, sulfonamido, $C_2$–$C_6$ alkenyl, an aryl, an aryl $C_1$–$C_6$ alkyl group, a hydroxyl, a nitro, a pyrrolidino, a morpholino, a piperidino, an amino or ammonio or a 1-imidazol(in)io group, wherein the last three groups can be substituted with one or more $C_1$–$C_6$ alkyl-, $C_1$–$C_6$ carboxyalkyl-$C_1$–$C_6$ hydroxyalkyl, $C_2$–$C_6$ alkenyl, $C_1$–$C_6$ alkoxy-$C_1$–$C_6$ alkyl, with optionally substituted benzylgroups, with sulfo-($C_1$–$C_4$)-alkyl or heterocycle-($C_1$–$C_4$) alkyl groups, wherein also two of the radicals $R^7$, $R^8$, $R^9$ and —Z—Y—$R^6$, together with the remainder of the molecule, can form a condensed, optionally substituted 5-, 6- or 7-membered ring that can equally have a condensed aromatic ring on it, wherein the system AR, depending on the ring size, can have further substituents that independently of one another can stand for the same groups as $R^7$, $R^8$ and $R^9$, Z stands for a direct bond, a carbonyl, a carboxy-($C_1$–$C_4$) alkylene, an optionally substituted $C_2$–$C_6$ alkenylene, $C_4$–$C_6$ alkadienylene, furylene, thienylene, arylene, vinylenearylene, vinylenefurylene, vinylenethienylene group, wherein Z, together with the —Y—$R^6$ group can also form an optionally substituted 5-, 6- or 7-membered ring.

Y stands for a group selected from carbonyl, a group according to Formula III and a group according to Formula IV,

wherein $R^{10}$ stands for a hydrogen atom, a hydroxyl group, a $C_1$–$C_4$ alkoxy group, a $C_1$–$C_6$ alkyl group, a $C_1$–$C_6$ hydroxyalkyl group, a $C_2$–$C_6$ polyhydroxyalkyl group, a $C_1$–$C_6$ alkoxy-$C_1$–$C_6$ alkyl group, $R^{11}$ and $R^{12}$ independently of one another stand for a $C_1$–$C_6$ alkyl group, an aryl group or form together with the structural element O—C—O of Formula IV a 5- or 6-membered ring.

The component B is particularly preferably selected from the group consisting of acetophenone, propiophenone, 2-hydroxyacetophenone, 3-hydroxyacetophenone, 4-hydroxyacetophenone, 2-hydroxypropiophenone, 3-hydroxypropiophenone, 4-hydroxypropiophenone, 2-hydroxybutyrophenone, 3-hydroxybutyrophenone, 4-hydroxybutyrophenone, 2,4-dihydroxyacetophenone, 2,5-dihydroxyacetophenone, 2,6-dihydroxyacetophenone, 2,3,4-trihydroxyacetophenone, 3,4,5-trihydroxyacetophenone, 2,4,6-trihydroxyacetophenone, 2,4,6-trimethoxyacetophenone, 3,4,5-trimethoxyacetophenone, 3,4,5-trimethoxy-acetophenone-diethylketal, 4-hydroxy-3-methoxy-acetophenone, 3,5-dimethoxy-4-hydroxyacetophenone, 4-aminoacetophenone, 4-dimethylaminoacetophenone, 4-morpholinoacetophenone, 4-piperidinoacetophenone, 4-imidazolinoacetophenone, 2-hydroxy-5-bromo-acetophenone, 4-hydroxy-3-nitroacetophenone, acetophenone-2-carboxylic acid, acetophenone-4-carboxylic acid, benzophenone, 4-hydroxybenzophenone, 2-aminobenzophenone, 4,4'-dihydroxybenzophenone, 2,4-dihydroxy-benzophenone, 2,4,4'-trihydroxybenzophenone, 2,3,4-trihydroxybenzophenone, 2-hydroxy-1-acetonaphthone, 1-hydroxy-2-acetonaphthone, chromone, chromone-2-carboxylic acid, flavone, 3-hydroxyflavone, 3,5,7-trihydroxyflavone, 4',5,7-trihydroxyflavone, 5,6,7-trihydroxyflavone, quercetin, 1-indanone, 9-fluorenone, 3-hydroxyfluorenone, anthrone, 1,8-dihydroxyanthrone, vanillin, coniferyl aldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 4-hydroxy-2,3-dimethoxybenzaldehyde, 4-hydroxy-2,5-dimethoxy-benzaldehyde, 4-hydroxy-2,6-dimethoxy-benzaldehyde, 4-hydroxy-2-methylbenzaldehyde, 4-hydroxy-3-methyl-benzaldehyde, 4-hydroxy-2,3-dimethylbenzaldehyde, 4-hydroxy-2,5-dimethyl-benzaldehyde, 4-hydroxy-2,6-dimethylbenzaldehyde, 4-hydroxy-3,5-dimethoxy-benzaldehyde, 4-hydroxy-3,5-dimethylbenzaldehyde, 3,5-diethoxy-4-hydroxy-benzaldehyde, 2,6-diethoxy-4-hydroxybenzaldehyde, 3-hydroxy-4-methoxy-benzaldehyde, 2-hydroxy-4-methoxybenzaldehyde, 2-ethoxy-4-hydroxy-benzaldehyde, 3-ethoxy-4-hydroxy-benzaldehyde, 4-ethoxy-2-hydroxybenzaldehyde, 4-ethoxy-3-hydroxy-benzaldehyde, 2,3-dimethoxybenzaldehyde, 2,4-dimethoxybenzaldehyde, 2,5-dimethoxybenzaldehyde, 2,6-dimethoxybenzaldehyde, 3,4-dimethoxybenzaldehyde, 3,5-dimethoxybenzaldehyde, 2,3

4-trimethoxybenzaldehyde, 2,3,5-trimethoxybenzaldehyde, 2,3,6-trimethoxybenzaldehyde, 2,4,6-trimethoxybenzaldehyde, 2,4,5-trimethoxybenzaldehyde, 2,5,6-trimethoxybenzaldehyde, 2-hydroxybenzaldehyde, 3-hydroxybenzaldehyde, 4-hydroxybenzaldehyde, 2,3-dihydroxybenzaldehyde, 2,4-dihydroxybenzaldehyde, 2,5-dihydroxybenzaldehyde, 2,6-dihydroxybenzaldehyde, 3,4-dihydroxybenzaldehyde, 3,5-dihydroxybenzaldehyde, 2,3,4-trihydroxybenzaldehyde, 2,3,5-trihydroxybenzaldehyde, 2,3,6-trihydroxybenzaldehyde, 2,4,6-trihydroxybenzaldehyde, 2,4,5-trihydroxybenzaldehyde, 2,5,6-trihydroxybenzaldehyde, 4-hydroxy-2-methoxybenzaldehyde, 4-dimethylaminobenzaldehyde, 4-diethylaminobenzaldehyde, 4-dimethylamino-2-hydroxybenzaldehyde, 4-diethylamino-2-hydroxybenzaldehyde, 4-pyrrolidinobenzaldehyde, 4-morpholinobenzaldehyde, 2-morpholinobenzaldehyde, 4-piperidinobenzaldehyde, 2-methoxy-1-naphthaldehyde, 4-methoxy-1-naphthaldehyde, 2-hydroxy-1-naphthaldehyde, 2,4-dihydroxy-1-napthaldehyde, 4-hydroxy-3-methoxy-1-naphthaldehyde, 2-hydroxy-4-methoxy-1-naphthaldehyde, 3-hydroxy-4-methoxy-1-naphthaldehyde, 2,4-dimethoxy-1-naphthaldehyde, 3,4-dimethoxy-1-naphthaldehyde, 4-hydroxy-1-naphthaldehyde, 4-dimethylamino-1-naphthaldehyde, 4-dimethylaminocinnamaldehyde, 2-dimethylaminobenzaldehyde, 2-chloro-4-dimethylaminobenzaldehyde, 4-dimethylamino-2-methylbenzaldehyde, 4-diethylaminocinnamaldehyde, 4-dibutylaminobenzaldehyde, 4-diphenylamino-benzaldehyde, 4-dimethylamino-2-methoxybenzaldehyde, 4-(1-imidazolyl)-benzaldehyde, piperonal, 2,3,6,7-tetrahydro-1H,5H-benzo[ij]quinolizin-9-carboxaldehyde, 2,3,6,7-tetrahydro-8-hydroxy-1H,5H-benzo[ij]quinolizin-9-carboxaldehyde, N-ethylcarbazole-3-aldehyde, 2-formylmethylene-1,3,3-trimethylindoline (Fischer's aldehyde or tribasen aldehyde), 2-indolaldehyde, 3-indolealdehyde, 1-methylindole-3-aldehyde, 2-methylindole-3-aldehyde, 1-acetylindole-3-aldehyde, 3-acetylindole, 1-methyl-3-acetylindole, 2-(1',3',3'-trimethyl-2-indolinylidene)acetaldehyde, 1-methylpyrrole-2-aldehyde, 1-methyl-2-acetylpyrrole, 4-pyridinealdehyde, 2-pyridinealdehyde, 3-pyridinealdehyde, 4-acetylpyridine, 2-acetylpyridine, 3-acetylpyridine, pyridoxal, quinoline-3-aldehyde, quinoline-4-aldehyde, antipyrine-4-aldehyde, furfural, 5-nitrofurfural, 2-thenoyl-trifluoroacetone, chromone-3-aldehyde, 3-(5'-nitro-2'-fury)-acrolein, 3-(2'-furyl)-acrolein and imidazole-2-aldehyde, 1,3-diacetylbenzene, 1,4-diacetylbenzene, 1,3,5-triacetylbenzene, 2-benzoyl-acetophenone, 2-(4'-methoxybenzoyl)acetophenone, 2-(2'-furoyl)acetophenone, 2-(2'-pyridoyl)acetophenone and 2-(3'-pyridoyl)acetophenone, benzylidene acetone, 4-hydroxybenzylidene acetone, 2-hydroxybenzylidene acetone, 4-methoxybenzylidene acetone, 4-hydroxy-3-methoxybenzylidene acetone, 4-dimethylaminobenzylidene acetone, 3,4-methylendioxybenzylidene acetone, 4-pyrrolidinobenzylidene acetone, 4-piperidinobenzylidene acetone, 4-morpholinobenzylidene acetone, 4-diethylaminobenzylidene acetone, 3-benzylidene-2,4-pentanedione, 3-(4'-hydroxybenzylidene)-2,4-pentanedione, 3-(4'-dimethylaminobenzylidene)-2,4-pentanedione, 2-benzylidenecyclohexanone, 2-(4'-hydroxybenzylidene)cyclohexanone, 2-(4'-dimethylaminobenzylidene)cyclohexanone, 2-benzylidene-1,3-cyclohexanedione, 2-(4'-hydroxybenzylidene)-1,3-cyclohexanedione, 3-(4'-dimethylaminobenzylidene)-1,3-cyclohexanedione, 2-benzylidene-5,5-dimethyl-1,3-cyclohexanedione, 2-(4'-hydroxybenzylidene)-5,5-dimethyl-1,3-cyclohexanedione, 2-(4'-hydroxy-3-methoxybenzylidene)-5,5-dimethyl-1,3-cyclohexanedione, 2-(4'-dimethylaminobenzylidene)-5,5-dimethyl-1,3-cyclohexanedione, 2-benzylidenecyclopentanone, 2'-(4-hydroxybenzylidene)-cyclopentanone, 2-(4'-dimethylaminobenzylidene)cyclopentanone, 5-(4-dimethylaminophenyl)penta-2,4-dienal, 5-(4-diethylaminophenyl)penta-2,4-dienal, 5-(4-methoxyphenyl)penta-2,4-dienal, 5-(3,4-dimethoxyphenyl)penta-2,4-dienal, 5-(2,4-dimethoxyphenyl)penta-2,4-dienal, 5-(4-piperidinophenyl)penta-2,4-dienal, 5-(4-morpholinophenyl)penta-2,4-dienal, 5-(4-pyrrolidinophenyl)penta-2,4-dienal, 6-(4-dimethylaminophenyl)hexa-3,5-dien-2-one, 6-(4-diethylaminophenyl)hexa-3,5-dien-2-one, 6-(4-methoxyphenyl)hexa-3,5-dien-2-one, 6-(3,4-dimethoxyphenyl)hexa-3,5-dien-2-one, 6-(2,4-dimethoxyphenyl)hexa-3,5-dien-2-one, 6-(4-piperidinophenyl)hexa-3,5-dien-2-one, 6-(4-morpholinophenyl)hexa-3,5-dien-2-one, 6-(4-pyrrolidinophenyl)hexa-3,5-dien-2-one, 5-(4-dimethylamino-1-naphthyl)penta-3,5-dienal, 2-nitrobenzaldehyde, 3-nitrobenzaldehyde, 4-nitrobenzaldehyde, 4-methyl-3-nitrobenzaldehyde, 3-hydroxy-4-nitrobenzaldehyde, 4-hydroxy-3-nitrobenzaldehyde, 5-hydroxy-2-nitrobenzaldehyde, 2-hydroxy-5-nitrobenzaldehyde, 2-hydroxy-3-nitrobenzaldehyde, 2-fluoro-3-nitrobenzaldehyde, 2-methoxy-2-nitrobenzaldehyde, 4-chloro-3-nitrobenzaldehyde, 2-chloro-6-nitrobenzaldehyde, 5-chloro-2-nitrobenzaldehyde, 4-chloro-2-nitrobenzaldehyde, 2,4-dinitrobenzaldehyde, 2,6-dinitrobenzaldehyde, 2-hydroxy-3-methoxy-5-nitrobenzaldehyde, 4,5-dimethoxy-2-nitrobenzaldehyde, 6-nitropiperonal, 2-nitropiperonal, 5-nitrovanillin, 2,5-dinitrosalicylaldehyde, 5-bromo-3-nitrosalicylaldehyde, 3-nitro-4-formylbenzenesulfonic acid, 4-nitro-1-naphthaldehyde, 2-nitrocinnamaldehyde, 3-nitrocinnamaldehyde, 4-nitrocinnamaldehyde, 9-methyl-3-carbazolealdehyde, 9-ethyl-3-carbazolealdehyde, 3-acetylcarbazole, 3,6-diacetyl-9-ethylcarbazole, 3-acetyl-9-methylcarbazole, 1,4-dimethyl-3-carbazole aldehyde, 1,4,9-trimethyl-3-carbazolealdehyde, 4-formyl-1-methylpyridinium-, 2-formyl-1-methylpyridinium-, 4-formyl-1-ethylpyridinium-, 2-formyl-1-ethylpyridinium-, 4-formyl-1-benzylpyridinium-, 2-formyl-1-benzylpyridinium-, 4-formyl-1,2-dimethylpyridinium-, 4-formyl-1,3-dimethylpyridinium-, 4-formyl-1-methylquinolinium-, 2-formyl-1-methylquinolinium-, 4-acetyl-1-methylpyridinium-, 2-acetyl-1-methylpyridinium-, 4-acetyl-1-methylquinolinium-, 5-formyl-1-methylquinolinium-, 6-formyl-1-methylquinolinium-, 7-formyl-1-methylquinolinium-, 8-formyl-1-methylquinolinium-, 5-formyl-1-ethylquinolinium-, 6-formyl-1-ethylquinolinium-, 7-formyl-1-ethylquinolinium-, 8-formyl-1-ethylquinolinium-, 5-formyl-1-benzylquinolinium-, 6-formyl-1-benzylquinolinium-, 7-formyl-1-benzylquinolinium-, 8-formyl-1-benzylquinolinium, 5-formyl-1-allylquinolinium-, 6-formyl-1-allylquinolinium-, 7-formyl-1-allylquinolinium- and 8-formyl-1-allylquinolinium-, 5-acetyl-1-methylquinolinium-, 6-acetyl-1-methylquinolinium-, 7-acetyl-1-methylquinolinium-, 8-acetyl-1-methylquinolinium, 5-acetyl-1-ethylquinolinium-, 6-acetyl-1-ethylquinolinium-, 7-acetyl-1-ethylquinolinium-, 8-acetyl-1-ethylquinolinium, 5-acetyl-1-benzylquinolinium-, 6-acetyl-1-benzylquinolinium-, 7-acetyl-1-benzylquinolinium-8-acetyl-1-benzylquinolinium-, 5-acetyl-1-allylquinolinium-, 6-acetyl-1-allylquinolinium-, 7-acetyl-1-allylquinolinium- and 8-acetyl-1-allylquinolinium-, 9-formyl-10-methylacridinium-, 4-(2'-formylvinyl)-1-methylpyridinium-, 1,3-dimethyl-2-(4'-formylphenyl)benzimidazolium-, 1,3-dimethyl-2-(4'-formylphenyl)imidazolium-, 2-(4'-formylphenyl)-3-methylbenzothiazolium-, 2-(4'-acetylphenyl)-3- methylbenzothiazolium-, 2-(4'-formylphenyl)-3-methylbenzoxazolium-, 2-(5'-formyl-2'-furyl)-3-methylbenzothiazolium-, 2-(5'-formyl-2'-furyl)-3-methylbenzothiazolium-, 2-(5'-formyl-2'-thienyl)-3-methylbenzothiazolium-, 2-(3'-formylphenyl)-3-methylbenzothiazolium-, 2-(4'-formyl-1-naphthyl)-3-methylbenzothiazolium-, 5-chloro-2-(4'-formylphenyl)-3-methylbenzothiazolium-, 2-(4'-formylphenyl)-3,5-dimethylbenzothiazolium benzenesulfonate, -p-toluenesulfonate, methanesulfonate, -perchlorate, -sulfate, -chloride, -bromide, -iodide, tetrachlorozincate, -methylsulfate-, -trifluoromethansulfonate, -tetrafluoroborate, isatin, 1-methyl-isatin, 1-allyl-isatin, 1-hydroxymethyl-isatin, 5-chloro-isatin, 5-methoxy-isatin, 5-nitroisatin, 6-nitroisatin, 5-sulfoisatin, 5-carboxyisatin, quinisatin, 1-methylquinisatin, together with any mixtures of the above compounds.

In a special embodiment, it can be advantageous to select the component B in such a manner that the group Y of Formula II is not a carbonyl group. In this case, it can be advantageous to select the component B from 2-{[(2-hydroxyethyl)imino]methyl}phenol, 3-{[(2-hydroxyethyl)imino]methyl}phenol, 4-{[(2-hydroxyethyl)imino]methyl}phenol, 3-{[(2-hydroxyethyl)imino]methyl}benzene-1,2-diol, 4-{[(2-hydroxyethyl)imino]methyl}benzene-1,3-diol, 2-{[(2-hydroxyethyl)imino]methyl}benzene-1,4-diol, 2-{[(2-hydroxyethyl)imino]methyl}benzene-1,3-diol, 4-{[(2-hydroxyethyl)imino]methyl}benzene-1,2-diol, 5-{[(2-hydroxyethyl)imino]methyl}benzene-1,3-diol, 4-{[(2-hydroxyethyl)imino]methyl}benzene-1,2,3-triol, 6-{[(2-hydroxyethyl)imino]methyl}benzene-1,2,4-triol, 3-{[(2-hydroxyethyl)imino]methyl}benzene-1,2,4-triol, 2-{[(2-hydroxyethyl)imino]methyl}benzene-1,3,5-triol, 5-{[(2-hydroxyethyl)imino]methyl}benzene-1,2,4-triol, 3-{[(2-hydroxyethyl)imino]methyl}benzene-1,2,4-triol, 2-{[(2-methoxyphenyl)methylene]amino}ethanol, 2-{[(3-methoxyphenyl)methylene]amino}ethanol, 2-{[(4-methoxyphenyl)methylene]amino}ethanol, 2-{[(2-ethoxyphenyl)methylene]amino}ethanol, 2-{[(3-ethoxyphenyl)methylene]amino}ethanol, 2-{[(4-ethoxyphenyl)-methylene]amino}ethanol, 2-{[(2,3-dimethoxyphenyl)methylene]amino}ethanol, 2-{[(2,4-dimethoxyphenyl)methylene]amino}ethanol, 2-[[(2,5-dimethoxyphenyl)methylene]amino}ethanol, 2-{[(2,6-dimethoxyphenyl)methylene]amino}ethanol, 2-{[(2,4-dimethoxyphenyl) methylene]amino}ethanol, 2-{[(3,5-dimethoxyphenyl)methylene]amino}ethanol, 2-[[(2,3,4-trimethoxyphenyl)methylene]amino}ethanol, 2[[(2,3,5-trimethoxyphenyl)methylene]amino}ethanol, 2-[[(2,3,6-trimethoxyphenyl)methylene]amino}ethanol, 2-[[(2,4,6-trimethoxyphenyl)methylene]amino}ethanol, 2-[[(2,4,5-trimethoxyphenyl)methylene]amino}ethanol, 2-[[(2,3,6-trimethoxyphenyl)methylene]amino}ethanol, 4-{[(2-hydroxyethyl)imino]methyl}-3-methoxyphenol, 4-{[(2-hydroxyethyl)imino]methyl}-2-methoxyphenol, 5-{[(2-hydroxyethyl)imino]methyl}-2-methoxyphenol, 2-{[(2-hydroxyethyl)imino]methyl}-5-methoxyphenol, 3-ethoxy-4-{[(2-hydroxyethyl)imino]methyl}phenol, 2-ethoxy-4-{[(2-hydroxyethyl)imino]methyl}phenol, 5-ethoxy-2-{[(2-hydroxyethyl)imino]methyl}phenol, 2-ethoxy-5-{[(2-hydroxyethyl)imino]methyl}phenol, 4-{[(2-hydroxyethyl)imino]methyl}-2,3-dimethoxyphenol, 4-{[(2-hydroxyethyl)imino]methyl}-2,5-dimethoxyphenol, 4-{[(2-hydroxyethyl)imino]methyl}-3,5-dimethoxyphenol, 4-{[(2-hydroxyethyl)imino]methyl}-2,6-dimethoxyphenol, 2,6-diethoxy-4-{[(2-hydroxyethyl)imino]methyl}phenol, 3,5-diethoxy-4-{[(2-hydroxyethyl)imino]methyl}phenol, 4-{[(2-hydroxyethyl)imino]methyl}-3-methylphenol, 4-{[(2-hydroxyethyl)imino]methyl}-2-methylphenol, 4-{[(2-hydroxyethyl)imino]methyl}-2,3-dimethylphenol, dimethylphenol, 4-{[(2-hydroxyethyl)imino]methyl}-2,5-dimethylphenol, 4-{[(2-hydroxyethyl)imino]methyl}-3,5-dimethylphenol, 4-{[(2-hydroxyethyl)imino]methyl}-2,6-dimethylphenol, 2-({[4-(dibutylamino)phenyl]methylene}amino)ethanol, 2-({[2-chloro-4-(dimethylamino)phenyl]methylene}amino)ethanol, 2-({[4-(dimethylamino)-2-methylphenyl]methylene}amino)ethanol, 2-({[4-(dimethylamino)-2-methoxyphenyl]methylene}amino)ethanol, 2-({[2-(dimethylamino)phenyl]methylene}amino)ethanol, 2-({[4-(dimethylamino)phenyl]methylene}amino)ethanol, 2-({[4-(diethylamino)phenyl]methylene}amino)ethanol, 5-(dimethylamino)-2-{[(2-hydroxyethyl)imino]methyl}phenol, 5-(diethylamino)-2-{[(2-hydroxyethyl)imino]methyl}phenol, 2-{[(4-pyrrolidin-1-ylphenyl)methylene]amino}ethanol, 2-{[(4-piperidin-1-ylphenyl)methylene]amino}ethanol, 2-{[(4-morpholin-4-ylphenyl)methylene]amino}ethanol, 2-{[(2-morpholin-4-ylphenyl)methylene]amino}ethanol, 2-{[(2-methoxy-1-naphthyl)methylene]amino}ethanol, 2-{[(4-methoxy-1-naphthyl)methylene]amino}ethanol, 1-{[(2-hydroxyethyl)imino]methyl}-2-naphthol, 4-{[(2-hydroxyethyl)imino]methyl}-1-naphthol, 4-{[(2-hydroxyethyl)imino]methyl}naphthalene-1,3-diol, 4-{[(2-hydroxyethyl)imino]methyl}-2-methoxy-1-naphthol, 1-{[(2-hydroxyethyl)imino]methyl}-2-methoxy-2-naphthol, 4-{[(2-hydroxyethyl)imino]methyl}-1-methoxy-2-naphthol, 2-{[(2,4-dimethoxy-1-naphthyl)methylene]amino}ethanol, 2-{[(3,4-dimethoxy-1-naphthyl)methylene]amino}ethanol, 2-({[4-(dimethylamino)-1-naphthyl]methylene}amino)ethanol, 2-({3-[4-(dimethylamino)phenyl]prop-2-enylidene}amino)ethanol, 2-({3-[4-(diethylamino)phenyl]prop-2-enylidene)amino)ethanol, 4-{3-[(2-hydroxyethyl)-imino]prop-1-enyl}-2-methoxyphenol, 2-(diethoxymethyl)phenol, 3-(diethoxymethyl)phenol, 4-(diethoxymethyl)phenol, 3-(diethoxymethyl)benzene-1,2-diol, 4-(diethoxymethyl)benzene-1,3-diol, 2-(diethoxymethyl)benzene-1,4-diol, 2-(diethoxymethyl)-benzene-1,3-diol, 4-(diethoxymethyl)benzene-1,2-diol, 5-(diethoxymethyl)benzene-1,3-diol, 4-(diethoxymethyl)benzene-1,2,3-triol, 6-(diethoxymethyl)benzene-1,2,4-triol, 3-(diethoxymethyl)benzene-1,2,4-triol, 2-(diethoxymethyl)benzene-1,3,5-triol, 5-(diethoxymethyl)benzene-1,2,4-triol, 3-(diethoxymethyl)benzene-1,2,4-triol, 1-(diethoxymethyl)-2-methoxybenzene, 1-(diethoxymethyl)-3-methoxybenzene, 1-(diethoxymethyl)-4-methoxybenzene, 1-(diethoxymethyl)-2-ethoxybenzene, 1-(diethoxymethyl)-3-ethoxybenzene, 1-(diethoxymethyl)-4-ethoxybenzene, 1-(diethoxymethyl)-2,3-dimethoxybenzene, 1-(diethoxymethyl)-2,4-dimethoxybenzene, 2-(diethoxymethyl)-1,4-dimethoxybenzene, 2-(diethoxymethyl)-1,3-dimethoxybenzene, 4-(diethoxymethyl)-1,2-dimethoxybenzene, 1-(diethoxymethyl)-3,5-dimethoxybenzene, 1-(diethoxymethyl)-2,3,4-trimethoxybenzene, 1-(diethoxymethyl)-2,3,5-trimethoxybenzene, 2-(diethoxymethyl)-1,3,4-trimethoxybenzene, 2-(diethoxymethyl)-1,3,5-trimethoxybenzene, 1-(diethoxymethyl)-2,4,5-trimethoxybenzene, 2-(diethoxymethyl)-1,3,4-trimethoxybenzene, 4-(diethoxymethyl)-3-methoxyphenol, 4-(diethoxymethyl)-2-methoxyphenol, 5-(diethoxymethyl)-2-methoxyphenol, 2-(diethoxymethyl)-5-methoxyphenol, 4-(diethoxymethyl)-3-ethoxyphenol, 4-(diethoxymethyl)-2-ethoxyphenol, 2-(diethoxymethyl)-5-ethoxyphenol, 5-(diethoxymethyl)-2-ethoxyphenol, 4-(diethoxymethyl)-2,3-dimethoxyphenol, 4-(diethoxymethyl)-2,5-dimethoxyphenol, 4-(diethoxymethyl)-3,5- dimethoxyphenol, 4-(diethoxymethyl)-2,6-dimethoxyphenol, 4-(diethoxymethyl)-2,6-diethoxyphenol, 4-(diethoxymethyl)-3,5-diethoxyphenol, 4-(diethoxymethyl)-3-methylphenol, 4-(diethoxymethyl)-2-methylphenol, 4-(diethoxymethyl)-2,3-dimethylphenol, 4-(diethoxymethyl)-2,5-dimethylphenol, 4-(diethoxymethyl)-3,5-dimethylphenol, 4-(diethoxymethyl)-2,6-dimethylphenol, N-[4-(diethoxymethyl)phenyl]-N,N-dibutylamine, N-[3-chloro-4-(diethoxymethyl)phenyl]-N,N-dimethylamine, N-[4-(diethoxymethyl)-3-methylphenyl]-N,N-dimethylamine, N-[4-(diethoxymethyl)-3-methoxyphenyl]-N,N-dimethylamine, N-[2-(diethoxymethyl)phenyl]-N,N-dimethylamine, N-[4-(diethoxymethyl)phenyl]-N,N-dimethylamine, N-[4-(diethoxymethyl)phenyl]-N,N-diethylamine, 2-(diethoxymethyl)-5-(dimethylamino)phenol, 2-(diethoxymethyl)-5-(diethylamino)phenol, 1-[4-(diethoxymethyl)phenyl]pyrrolidine, 1-[4-(diethoxymethyl)phenyl]piperidine, 4-[4-(diethoxymethyl)phenyl]morpholine, 4-[2-(diethoxymethyl)phenyl]morpholine, 1-(diethoxymethyl)-2-methoxynaphthalene, 1-(diethoxymethyl)$_4$-methoxynaphthalene, 1-(diethoxymethyl)-2-naphthol, 4-(diethoxymethyl)-1-naphthol, 4-(diethoxymethyl)-naphthalene-1,3-diol, 4-(diethoxymethyl)-2-methoxy-1-naphthol, 1-(diethoxymethyl)-4-methoxy-2-naphthol, 4-(diethoxymethyl)-1-methoxy-2-naphthol, 1-(diethoxymethyl)-2,4-dimethoxynaphthalene, 4-(diethoxymethyl)-1,2-dimethoxynaphthalene, N-[4-(diethoxymethyl)-1-naphthyl]-N,N-dimethylamine, N-{4-[3,3-diethoxyprop-1-enyl]phenyl}-N,N-dimethylamine, N-{4-[3,3-diethoxyprop-1-enyl]phenyl}-N,N-diethylamine and 4-(3,3-diethoxyprop-1-enyl)-2-methoxyphenol.

Benzaldehyde, cinnamic aldehyde and naphthaldehyde, as well as their derivatives, particularly with one or more hydroxyl, alkoxy and amino substituents, are quite particularly preferred for use as component B. Here again the compounds according to Formula V are preferred,

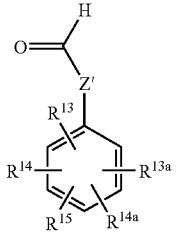

(V)

in which

R$^{13}$, R$^{14}$ and R$^{15}$ independently of one another stand for a hydrogen atom, a halogen atom, a C$_1$–C$_6$ alkyl group, a hydroxyl group, a C$_1$–C$_6$ alkoxy group, an amino group, a C$_1$–C$_6$ dialkylamino group, a di(C$_2$–C$_6$ hydroxyalkyl)amino group, a di(C$_1$–C$_6$ alkoxy-C$_1$–C$_6$ alkyl)amino group, a C$_1$–C$_6$ hydroxyalkyloxy group, a sulfonyl group, a carboxyl group, a sulfonic acid group, a sulfonamide group, a sulfonamide group, a carbamoyl group, a C$_2$–C$_6$ acyl group, an acetyl group or a nitro group, Z' stands for a direct bond or a vinylene group, R$^{13a}$ and R$^{14a}$ stand for hydrogen or together with the remainder of the molecule can form a 5- or 6-membered aromatic or aliphatic ring.

Quite particularly preferred compounds for component B are selected from the group consisting of vanillin, coniferyl aldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 4-hydroxy-2,3-dimethoxy-benzaldehyde, 4-hydroxy-2,5-dimethoxybenzaldehyde, 4-hydroxy-2,6-dimethoxybenzaldehyde, 4-hydroxy-2-methylbenzaldehyde, 4-hydroxy-3-methylbenzaldehyde, 4-hydroxy-2,3-dimethylbenzaldehyde, 4-hydroxy-2,5-dimethylbenzaldehyde, 4-hydroxy-2,6-dimethylbenzaldehyde, 4-hydroxy-3,5-dimethoxybenzaldehyde, 4-hydroxy-3,5-dimethylbenzaldehyde, 3,5-diethoxy-4-hydroxybenzaldehyde, 2,6-diethoxy-4-hydroxybenzaldehyde, 3-hydroxy-4-methoxybenzaldehyde, 2-hydroxy-4-methoxybenzaldehyde, 2-ethoxy-4-hydroxybenzaldehyde, 3-ethoxy-4-hydroxybenzaldehyde, 4-ethoxy-2-hydroxy-benzaldehyde, 4-ethoxy-3-hydroxybenzaldehyde, 2,3-dimethoxybenzaldehyde, 2,4-dimethoxybenzaldehyde, 2,5-dimethoxybenzaldehyde, 2,6-dimethoxybenzaldehyde, 3,4-dimethoxybenzaldehyde, 3,5-dimethoxybenzaldehyde, 2,3,4-trimethoxybenzaldehyde, 2,3,5-trimethoxybenzaldehyde, 2,3,6-trimethoxybenzaldehyde, 2,4,6-trimethoxybenzaldehyde, 2,4,5-trimethoxybenzaldehyde, 2,5,6-trimethoxybenzaldehyde, 2-hydroxybenzaldehyde, 3-hydroxybenzaldehyde, 4-hydroxybenzaldehyde, 2,3-dihydroxybenzaldehyde, 2,4-dihydroxybenzaldehyde, 2,5-dihydroxybenzaldehyde, 2,6-dihydroxybenzaldehyde, 3,4-dihydroxybenzaldehyde, 3,5-dihydroxybenzaldehyde, 2,3,4-trihydroxybenzaldehyde, 2,3,5-trihydroxybenzaldehyde, 2,3,6-trihydroxybenzaldehyde, 2,4,6-trihydroxybenzaldehyde, 2,4,5-trihydroxybenzaldehyde, 2,5,6-trihydroxybenzaldehyde, 4-hydroxy-2-methoxybenzaldehyde, 4-dimethylaminobenzaldehyde, 4-diethylaminobenzaldehyde, 4-dimethylamino-2-hydroxybenzaldehyde, 4-diethylamino-2-hydroxybenzaldehyde, 4-pyrrolidinobenzaldehyde, 4-morpholinobenzaldehyde, 2-morpholinobenzaldehyde, 4-piperidinobenzaldehyde, 2-methoxy-1-naphthaldehyde, 4-methoxy-1-naphthaldehyde, 2-hydroxy-1-naphthaldehyde, 2,4-dihydroxy-1-napthaldehyde, 4-hydroxy-3-methoxy-1-naphthaldehyde, 2-hydroxy-4-methoxy-1-naphthaldehyde, 3-hydroxy-4-methoxy-1-naphthaldehyde, 2,4-dimethoxy-1-naphthaldehyde, 3,4-dimethoxy-1-naphthaldehyde, 4-hydroxy-1-naphthaldehyde, 4-dimethylamino-1-naphthaldehyde, 4-dimethylaminocinnamaldehyde, 2-dimethylaminobenzaldehyde, 2-chloro-4-dimethylaminobenzaldehyde, 4-dimethylamino-2-methylbenzaldehyde, 4-diethylaminocinnamaldehyde, 4-dibutylaminobenzaldehyde, 4-diphenylamino-benzaldehyde, 4-dimethylamino-2-methoxybenzaldehyde, 4-(1-imidazolyl)-benzaldehyde and piperonal.

In a second embodiment, it can be advantageous to broaden the color spectrum and improve the fastness properties by adding to the inventive agent besides at least one compound according to Formula I and at least one reactive carbonyl compound (component B), at least a further compound as component C, selected from (a) CH-acid compounds and (b) compounds with primary or secondary amino or hydroxyl groups, selected from aromatic hydroxyl compounds, primary or secondary aromatic amines and nitrogen-containing heterocyclic compounds.

The CH-acid compounds of the component C are selected from the group consisting of 1,2,3,3-tetramethyl-3H-indolium iodide, 1,2,3,3-tetramethyl-3H-indolium p-toluenesulfonate, 1,2,3,3-tetramethyl-3H-indolium methanesulfonate, 1,3,3-trimethyl-2-methyleneindoline (Fischer Base), 2,3-dimethyl-benzothiazolium iodide, 2,3-dimethylbenzothiazolium p-toluenesulfonate, 2,3-dimethyl-naphtho[1,2-d]thiazolium p-toluenesulfonate, 3-ethyl-2-methyl-naphtho[1,2-d]thiazolium p-toluenesulfonate, rhodanine, rhodanine-3-acetic acid, 1,4-dimethylquinolinium iodide, 1,2-dimethylquinolinium iodide, barbituric acid, thiobarbituric acid, 1,3-dimethylthiobarbituric acid, 1,3-diethylthiobarbituric acid, 1,3-diethylbarbituric acid, oxindole, 3-indoxy]acetate, 2-coumaranone, 5-hydroxy-2-coumaranone, 6-hydroxy-2-coumaranone, 3-methyl-1-phenyl-pyrazolin-5-one, indane-1,2-dione, indane-1,3-dione, indan-1-one, benzoylacetonitrile, 3-dicyanomethyleneindan-1-one, 2-amino-4-imino-1,3-thiazoline hydrochloride, 5,5-dimethylcyclohexane-1,3-dione, 2H-1,4-benzoxazine-4H-3-one, 3-ethyl-2-methyl-benzoxazolium iodide, 3-ethyl-2-methylbenzothiazolium iodide, 1-ethyl-4-methylquinolinium iodide, 1-ethyl-2-methylquinolinium iodide, 1,2,3-trimethylquinoxalinium iodide, 3-ethyl-2-methylbenzoxazolium p-toluenesulfonate, 3-ethyl-2-methylbenzothiazolium p-toluenesulfonate, 1-ethyl-4-methylquinolinium p-toluenesulfonate, 1-ethyl-2-methylquinolinium p-toluenesulfonate, and 1,2,3-trimethylquinoxalinium p-toluenesulfonate.

The primary and secondary aromatic amines of the component C are preferably selected from the group consisting of N,N-dimethyl-p-phenylenediamine, N,N-diethyl-p-phenylenediamine, N-(2-hydroxyethyl)-N-ethyl-p-phenylenediamine, N,N-bis-(2-hydroxyethyl)-p-phenylenediamine, N-(2-methoxyethyl)-p-phenylenediamine, 2,3-dichloro-p-phenylenediamine, 2,4-dichloro-p-phenylenediamine, 2,5-dichloro-p-phenylenediamine, 2-chloro-p-phenylenediamine, 2,5-dihydroxy-4-morpholinoaniline, 2-aminophenol, 3-aminophenol, 4-aminophenol, 2-aminomethyl-4-aminophenol, 2-hydroxymethyl-4-aminophenol, o-phenylenediamine, m-phenylenediamine, p-phenylenediamine, 2,5-diaminotoluene, 2,5-diaminophenol, 2,5-diaminoanisole, 2,5-diaminophenethol, 4-amino-3-methylphenol, 2-(2,5-diaminophenyl)ethanol, 2,4-diaminophenoxyethanol, 2-(2,5-diaminophenoxy)ethanol, 3-amino-4-(2-hydroxyethyloxy)phenol, 3,4-methylenedioxyphenol, 3,4-methylenedioxyaniline, 3-amino-2,4-dichlorophenol, 4-methylaminophenol, 2-methyl-5-aminophenol, 3-methyl-4-aminophenol, 2-methyl-5-(2-hydroxyethylamino)phenol, 3-amino-2-chloro-6-methylphenol, 2-methyl-5-amino-4-chlorophenol, 5-(2-hydroxyethylamino)$_4$-methoxy-2-methylphenol, 4-amino-2-hydroxymethylphenol, 2-(diethylaminomethyl)4-aminophenol, 4-amino-1-hydroxy-2-(2-hydroxyethylaminomethyl)benzene, 1-hydroxy-2-amino-5-methyl-benzene, 1-hydroxy-2-amino-6-methyl-benzene, 2-amino-5-acetamidophenol, 1,3-dimethyl-2,5-diaminobenzene, 5-(3-hydroxypropylamino)-2-methylphenol, 5-amino-4-methoxy-2-methylphenol, N,N-dimethyl-3-aminophenol, N-cyclopentyl-3-aminophenol, 5-amino-4-fluoro-2-methylphenol, 2,4-diamino-5-fluorotoluene, 2,4-diamino-5-(2-hydroxyethoxy)-toluene, 2,4-diamino-5-methylphenetol, 3,5-diamino-2-methoxy-1-methylbenzene, 2-amino-4-(2-hydroxyethylamino)anisole, 2,6-bis-(2-hydroxyethylamino)-1-methylbenzene, 1,3-diamino-2,4-dimethoxybenzene, 3,5-diamino-2-methoxy-toluene, 2-aminobenzoic acid, 3-aminobenzoic acid, 4-aminobenzoic acid, 2-aminophenylacetic acid, 3-aminophenylacetic acid, 4-aminophenylacetic acid, 2,3-diaminobenzoic acid, 2,4-diaminobenzoic acid, 2,5-diaminobenzoic acid, 3,4-diaminobenzoic acid, 3,5-diaminobenzoic acid, 4-aminosalicylic acid, 5-aminosalicylic acid, 3-amino-4-hydroxybenzoic acid, 4-amino-3-hydroxybenzoic acid, 2-aminobenzenesulfonic acid, 3-aminobenzenesulfonic acid, 4-aminobenzenesulfonic acid, 3-amino-4-hydroxybenzenesulfonic acid, 4-amino-3-hydroxynaphthalene-1-sulfonic acid, 6-amino-7-hydroxynaphthalene-2-sulfonic acid, 7-amino-4-hydroxynaphthalene-2-sulfonic acid, 4-amino-5-hydroxynaphthalene-2,7-disulfonic acid, 3-amino-2-naphthoic acid, 3-aminophthalic acid, 5-aminoisophthalic acid, 1,3,5-triaminobenzene, 1,2,4-triaminobenzene, 1,2,4,5-tetraminobenzene, 2,4,5-triaminophenol, pentaminobenzene, hexaminobenzene, 2,4,6-triaminoresorcine, 4,5-diaminopyrocatechol, 4,6-diaminopyrogallol, 1-(2-hydroxy-5-aminobenzyl)-2-imidazolidinone, 4-amino-2((4-[(5-amino-2-hydroxyphenyl)methyl]-piperazinyl)methyl)phenol, 3,5-diamino-4-hydroxypyrocatechol, 1,4-bis-(4-aminophenyl)-1,4-diazacycloheptane, aromatic nitriles, such as 2-amino-4-hydroxybenzonitrile, 4-amino-2-hydroxybenzonitrile, 4-aminobenzonitrile, 2,4-diaminobenzonitrile, amino compounds with nitro groups, such as 3-amino-6-methylamino-2-nitropyridine, picramic acid, [8-[(4-amino-2-nitrophenyl)-azo]-7-hydroxy-naphth-2-yl]trimethylammonium chloride, [8-[(4-amino-3-nitrophenyl)-azo)-7-hydroxy-naphth-2-yl] trimethylammonium chloride (Basic Brown 17), 1-hydroxy-2-amino-4,6-dinitrobenzene, 1-amino-2-nitro-4-[bis(2-hydroxyethyl)amino]benzene, 1-amino-2-[(2-hydroxyethyl) amino]-5-nitrobenzene (HC Yellow Nr. 5), 1-amino-2-nitro-4-[(2-hydroxyethyl)amino]benzene (HC Red Nr. 7), 2-chloro-5-nitro-N-2-hydroxyethyl-1,4-phenylenediamine, 1-[(2-hydroxyethyl)amino]-2-nitro-4-aminobenzene (HC Red Nr. 3), 4-amino-3-nitrophenol, 4-amino-2-nitrophenol, 6-nitro-o-toluidine, 1-amino-3-methyl-4-[(2-hydroxyethyl) amino]-6-nitrobenzene (HC Violet Nr. 1), 1-amino-2-nitro-4-[(2,3-dihydroxypropyl)amino]-5-chlorobenzene (HC Red Nr. 10), 2-(4-amino-2-nitroanilino)benzoic acid, 6-nitro-2,5-diaminopyridine, 2-amino-6-chloro-4-nitrophenol, disodium salt of 1-amino-2-(3-nitrophenylazo)-7-phenylazo-8-naphthol-3,6-disulfonic acid (acid blue Nr.29), disodium salt of 1-amino-2-(2-hydroxy-4-nitrophenylazo)-8-naphthol-3,6-disulfonic acid (Palatinchrome green), disodium salt of 1-amino-2-(3-chloro-2-hydroxy-5-nitrophenylazo)-8-naphthol-3,6-disulfonic acid (Gallion), disodium salt of 4-amino-4'-nitrostilbene-2,2'-disulfonic acid, 2,4-diamino-3',5'-dinitro-2'-hydroxy-5-methylazobenzene (Mordant brown 4), 4'-amino-4-nitrodiphenylamine-2-sulfonic acid, 4'-amino-3'-nitrobenzophenone-2-carboxylic acid, 1-amino-4-nitro-2-(2-nitrobenzylideneamino)benzene, 2-[2-(diethylamino) ethylamino]-5-nitroaniline, 3-amino-4-hydroxy-5-nitrobenzenesulfonic acid, 3-amino-3'-nitrobiphenyl, 3-amino-4-nitroacenaphthene, 2-amino-1-nitronaphthalene, 5-amino-6-nitrobenzo-1,3-dioxol, anilines, particularly anilines containing nitro groups, such as 4-nitroaniline, 2-nitroaniline, 1,4-diamino-2-nitrobenzene, 1,2-diamino-4-nitrobenzene, 1-amino-2-methyl-6-nitrobenzene, 4-nitro-1, 3-phenylenediamine, 2-nitro-4-amino-1-(2-hydroxyethylamino)benzene, 2-nitro-1-amino-4-[bis(2-hydroxyethyl) amino]benzene, 4-amino-2-nitrodiphenylamine-2'-carboxylic acid, 1-amino-5-chloro-4-(2-hydroxyethylamino)-2-nitrobenzene, aromatic anilines or phenols with a further aromatic radical, as illustrated in Formula VI (VI)

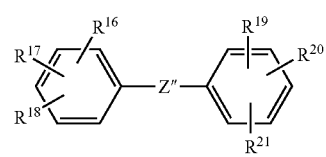

in which

R$^{16}$ stands for a hydroxyl or amino group that can be substituted with C$_1$–C$_6$ alkyl-, C$_1$–C$_6$ hydroxyalkyl-, C$_1$–C$_6$ alkoxy- or C$_1$–C$_6$ alkoxy-C$_1$–C$_6$ alkyl groups, R$^{17}$, R$^{18}$, R$^{19}$, R$^{20}$ and R$^{21}$ independently of one another stand for a hydrogen atom, a hydroxyl or an amino group that can be substituted with C$_1$–C$_6$ alkyl-, C$_1$–C$_6$ hydroxyalkyl-, C$_1$–C$_6$ alkoxy-, C$_1$–C$_6$ aminoalkyl- or C$_1$–C$_6$ alkoxy-C$_1$–C$_6$ alkyl groups, and Z" is a direct bond, a saturated or unsaturated carbon chain with 1 to 4 carbon atoms, optionally substituted with hydroxyl groups, a carbonyl-, sulfonyl- or imino group, an oxygen- or sulfur atom, or a group with the Formula VII

—Q'—(CH$_2$—Q—CH$_2$—Q")$_o$—  (VII)

in which

Q means a direct bond, a CH$_2$— or CHOH group,

Q' and Q" independently of one another stand for an oxygen atom, an NR$^{22}$ group, in which R$^{22}$ means a hydrogen atom, a C$_1$–C$_6$ alkyl group or C$_1$–C$_6$ hydroxyalkyl group, wherein also both groups, together with the remainder of the molecule can form a 5-, 6- or 7-membered ring, the groups O—(CH$_2$)$_p$—NH or NH—(CH$_2$)$_{p'}$—O, in which p and p' are 2 or 3, and o means a number from 1 to 4, such as, for example 4,4'-diaminostilbene and its hydrochloride, mono- or di-Na-salt of 4,4'-diaminostilbene-2,2'-disulfonic acid, 4-amino-4'-dimethylaminostilbene and its hydrochloride, 4,4'-diaminodiphenylmethane, 4,4'-diaminodiphenylsulfide, 4,4'-diaminodiphenylsulfoxide, 4,4'-diaminodiphenylamine, 4,4'-diaminodiphenylamine-2-sulfonic acid, 4,4'-diaminobenzophenone, 4,4'-diaminodiphenylether, 3,3',4,4'-tetraminodiphenyl, 3,3',4,4'-tetramino-benzophenone, 1,3-bis-(2,4-diaminophenoxy)propane, 1,8-bis-(2,5-diaminophenoxy)-3,6-dioxaoctane, 1,3-bis-(4-aminophenylamino)propane, 1,3-bis-(4-aminophenylamino)-2-propanol, 1,3-bis-[N-(4-aminophenyl)-2-hydroxyethylamino]-2-propanol, N,N-bis-[2-(4-aminophenoxy)ethyl]methyl amine, N-phenyl-1,4-phenylenediamine and bis(5-amino-2-hydroxyphenyl)methane.

The nitrogen-containing heterocyclic compounds of the component C are preferably selected from the group consisting of 2-aminopyridine, 3-aminopyridine, 4-aminopyridine, 2-amino-3-hydroxypyridine, 2,6-diaminopyridine, 2,5-diaminopyridine, 2-(aminoethylamino)-5-aminopyridine, 2,3-diaminopyridine, 2-dimethylamino-5-aminopyridine, 2-methylamino-3-amino-6-methoxypyridine, 2,3-diamino-6-methoxypyridine, 2,6-dimethoxy-3,5-diaminopyridine, 2,4,5-triaminopyridine, 2,6-dihydroxy-3,4-dimethylpyridine, N-[2-(2,4-diaminophenyl)aminoethyl]-N-(5-amino-2-pyridyl)amine, N-[2-(4-aminophenyl)aminoethyl]-N-(5-amino-2-pyridyl)amine, 2,4-dihydroxy-5,6-diaminopyrimidine, 4,5,6-triaminopyrimidine, 4-hydroxy-2,5,6-triaminopyrimidine, 2-hydroxy-4,5,6-triaminopyrimidine, 2,4,5,6-tetraminopyrimidine, 2-methylamino-4,5,6-triaminopyrimidine, 2,4-diaminopyrimidine, 4,5-diaminopyrimidine, 2-amino-4-methoxy-6-methyl-pyrimidine, 3,5-diaminopyrazole, 3,5-diamino-1,2,4-triazole, 3-aminopyrazole, 3-amino-5-hydroxypyrazole, 1-phenyl-4,5-diaminopyrazole, 1-(2-hydroxyethyl)-4,5-diaminopyrazole, 1-phenyl-3-methyl-4,5-diaminopyrazole, 4-amino-2,3-dimethyl-1-phenyl-3-pyrazolin-5-one (4-aminoantipyrine), 1-phenyl-3-methylpyrazol-5-one, 2-aminoquinoline, 3-aminoquinoline, 8-aminoquinoline, 4-aminoquinaldine, 2-aminonicotinic acid, 6-aminonicotinic acid, 5-aminoisoquinoline, 5-aminoindazole, 6-aminoindazole, 5-aminobenzimidazole, 7-aminobenzimidazole, 5-aminobenzothiazole, 7-aminobenzothiazole, 2,5-dihydroxy-4-morpholino-aniline as well as indole- and indoline derivatives, such as 4-aminoindole, 5-aminoindole, 6-aminoindole, 7-aminoindole, 5,6-dihydroxyindole, 5,6-dihydroxyindoline, 4-hydroxyindoline. Further heterocyclic compounds that can be used according to the invention are the hydroxypyrimidines disclosed in DE-U1-299 08 573. The above named compounds can be used both in their free form and in the form of their physiologically compatible salts, e.g. as salts of inorganic acids, such as hydrochloric or sulfuric acid.

The aromatic hydroxyl compounds of the component C are preferably selected from the group consisting of 2-, 4-, 5-methylresorcinol, 2,5-dimethylresorcinol, resorcinol, 3-methoxyphenol, pyrocatechol, hydroquinone, pyrogallol, phloroglucine, hydroxyhydroquinone, 2-, 3-, 4-methoxy-, 3-dimethylamino-, 2-(2-hydroxyethyl)-, 3,4-methylenedioxyphenol, 2,4-, 3,4-dihydroxybenzoic acid, -phenylacetic acid, gallic acid, 2,4,6-trihydroxybenzoic acid, -acetophenone, 2-, 4-chlororesorcinol, 1-naphthol, 1,5-, 2,3-, 2,7-dihydroxynaphthalene, 6-dimethylamino-4-hydroxy-2-naphthalenesulfonic acid and 3,6-dihydroxy-2,7-naphthalenesulfonic acid.

Hair dyes that inter alia comprise at least one compound with a 1,2-dihydropyrimidinium radical as the substantive dyestuff are known to the person skilled in the art from the printed publications EP-A2-998 908 and JP-A2-2002047153. In a third embodiment the dye comprises at least one reaction product (subsequently called reaction product RP) from a 1,2-dihydropyrimidinium derivative of Formula I and a compound of component B, particularly compounds according to Formula II, as the substantive dyestuff. Such reaction products RP can be obtained by e.g. heating both reaction partners in an aqueous, neutral to weakly alkaline medium, whereby the reaction products RP either precipitate out as a solid from the solution or are isolated therefrom by evaporating the solution. There is also the possibility of synthesizing the reaction products according to the literature H. Baumann et al., J. Liebigs Ann. Chem., 1968, 717, 124–136 or DE-A1-2165913.

Consequently, the inventive agents can comprise reaction products RP according to the Formula VIII,

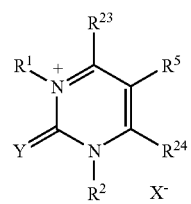

(VIII)

in which

R$^1$, R$^2$, R$^5$, Y and X$^{-1}$ are defined according to claim 1,

R$^{23}$ and R$^{24}$ independently of one another stand for a hydrogen atom, a C$_1$–C$_6$ alkyl group, a group according to Formula IX,

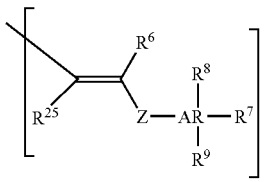

in which
R⁶, R⁷, R⁸, R⁹, AR and Z are defined as described under Formula II,
$R^{25}$ stands for a hydrogen atom or a $C_1$–$C_5$ alkyl group with the proviso that at least one of the radicals $R^{23}$ and $R^{24}$ stands for a group according to Formula IX.

Molar ratios of component B to the compound according to Formula I can be expediently from about 1:1 to about 2.1 for the synthesis of the reaction product RP. For a 1,2-dihydropyrimidinium derivative according to Formula I when only one substituent $R^{23}$ or $R^{24}$ differs from hydrogen, then about 1 mole-equivalent of component B is reacted with one mole-equivalent 1,2-dihydropyrimidinium derivative. In this case, either $R^{23}$ or $R^{24}$ in Formula VIII stands for a hydrogen atom and the other radical for a group according to Formula IX. If both substituents $R^3$ and $R^4$ in Formula I are different from a hydrogen atom, then these 1,2-dihydropyrimidinium derivatives can be reacted with both about one and about two mole-equivalents of component B. In the last case, both radicals $R^{23}$ and $R^{24}$ in the resulting reaction products RP stand for a group according to Formula IX.

It is particularly preferred if the inventive agent comprise such reaction products RP according to Formula VIII, in which AR, according to Formula IX stands for benzene or naphthalene.

It is further particularly preferred if the inventive agent comprises such reaction products RP according to Formula VIII, in which Z, according to Formula IX stands for a direct bond or vinylene.

It is particularly preferred if the inventive agent comprises such reaction products RP according to Formula. VIII, in which $R^{25}$, according to Formula IX stands for a hydrogen atom.

It is particularly preferred if the inventive agent comprises such reaction products RP according to Formula VIII, in which $R^6$, according to Formula IX stands for a hydrogen atom.

It is particularly preferred if the inventive agent comprises such reaction products RP according to Formula VIII, in which $R^7$, $R^8$ and $R^9$, according to Formula IX stand, independently of one another for a hydrogen atom, a halogen atom, a $C_1$–$C_6$ alkyl group, a hydroxyl group, a $C_1$–$C_6$ alkoxy group, an amino group, a $C_1$–$C_6$ dialkylamino group, a di($C_2$–$C_6$ hydroxyalkyl)amino group, a di($C_1$–$C_6$ alkoxy-$C_1$–$C_6$-alkyl)amino group, a $C_1$–$C_6$ hydroxyalkyloxy group, a sulfonyl group, a carboxyl group, a sulfonamide group, a carbamoyl group, a $C_2$–$C_6$ acyl group, an acetyl group, a sulfonic acid group, a sulfonamide group or a nitro group.

It is particularly preferred if the inventive agent comprises such reaction products RP according to Formula VIII, in which $R^7$, $R^8$ and $R^9$, according to Formula IX stand, independently of one another for a hydrogen atom, a halogen atom, a $C_1$–$C_6$ alkyl group, a hydroxyl group, a $C_1$–$C_6$ alkoxy group, an amino group, a $C_1$–$C_6$ dialkylamino group, a di($C_2$–$C_6$ hydroxyalkyl)amino group, a di($C_1$–$C_6$ alkoxy-$C_1$–$C_6$-alkyl)amino group, a $C_1$–$C_6$ hydroxyalkyloxy group, a sulfonyl group, a carboxyl group, a sulfonamide group, a carbamoyl group, a $C_2$–$C_6$ acyl group, an acetyl group, a sulfonic acid group, a sulfonamide group or a nitro group, with the proviso that if AR stands for benzene and one of the radicals $R^7$, $R^8$ or $R^9$, para to group Z stands for a hydrogen atom, a halogen atom, a $C_1$–$C_6$ alkoxy group or an amino group, then both the other radicals independently of one another mean neither a hydrogen atom nor a halogen atom.

It is particularly preferred if the inventive agent comprises such reaction products RP according to Formula VIII, in which $R^7$, $R^8$ and $R^9$, according to Formula IX stand, independently of one another for a hydrogen atom, a halogen atom, a $C_1$–$C_6$ alkyl group, a hydroxyl group, a $C_1$–$C_6$ alkoxy group, an amino group, a $C_1$–$C_6$ dialkylamino group, a di($C_2$–$C_6$ hydroxyalkyl)amino group, a di($C_1$–$C_6$ alkoxy-$C_1$–$C_6$-alkyl)amino group, a $C_1$–$C_6$ hydroxyalkyloxy group, a sulfonyl group, a carboxyl group, a sulfonamide group, a carbamoyl group, a $C_2$–$C_6$ acyl group, an acetyl group, a sulfonic acid group, a sulfonamide group or a nitro group, with the proviso that if AR stands for benzene, at least one of the radicals $R^7$, $R^8$ or $R^9$ stands for a group selected from a hydroxyl group, a $C_1$–$C_6$ dialkylamino group, a di($C_2$–$C_6$ hydroxyalkyl)amino group, a di($C_1$–$C_6$ alkoxy-$C_1$–$C_6$-alkyl) amino group and a $C_1$–$C_6$ hydroxyalkyloxy group.

According to this embodiment, a quite particularly preferred reaction product RP according to Formula VIII comprised in the inventive agents is at least one compound selected from the group consisting of 4-[2-[2-hydroxyphenyl]ethenyl]-2,3-dihydro-1,3,6-trimethyl-2-oxo-pyrimidinium chloride, 4-[2-[3-hydroxyphenyl]ethenyl]-2,3-dihydro-1,3,6-trimethyl-2-oxo-pyrimidinium hydrogen sulfate, 4-[2-[4-hydroxyphenyl]ethenyl]-2,3-dihydro-1,3,6-trimethyl-2-oxo-pyrimidinium chloride, 4-[2-[2,3-dihydroxyphenyl]ethenyl]-2,3-dihydro-1,3,6-trimethyl-2-oxo-pyrimidinium chloride, 4-[2-[2,4-dihydroxyphenyl]ethenyl]-2,3-dihydro-1,3,6-trimethyl-2-oxo-pyrimidinium chloride, 4-[2-[2,5-dihydroxyphenyl]ethenyl]-2,3-dihydro-1,3,6-trimethyl-2-oxo-pyrimidinium hydrogen sulfate, 4-[2-[2,6-dihydroxyphenyl]ethenyl]-2,3-dihydro-1,3,6-trimethyl-2-oxo-pyrimidinium chloride, 4-[2-[3,4-dihydroxyphenyl]ethenyl]-2,3-dihydro-1,3,6-trimethyl-2-oxo-pyrimidinium chloride, 4-[2-[3,5-dihydroxyphenyl]ethenyl]-2,3-dihydro-1,3,6-trimethyl-2-oxo-pyrimidinium chloride, 4-[2-[3,6-dihydroxyphenyl]ethenyl]-2,3-dihydro-1,3,6-trimethyl-2-oxo-pyrimidinium chloride, 4-[2-[2,3,4-trihydroxyphenyl]ethenyl]-2,3-dihydro-1,3,6-trimethyl-2-oxo-pyrimidinium chloride, 4-[2-[2,3,5-trihydroxyphenyl]ethenyl]-2,3-dihydro-1,3,6-trimethyl-2-oxo-pyrimidinium hydrogen sulfate, 4-[2-[2,3,6-trihydroxyphenyl]ethenyl]-2,3-dihydro-1,3,6-trimethyl-2-oxo-pyrimidinium chloride, 4-[2-[3,4,5-trihydroxyphenyl]ethenyl]-2,3-dihydro-1,3,6-trimethyl-2-oxo-pyrimidinium hydrogen sulfate, 4-[2-[3,4,6-trihydroxyphenyl]-ethenyl]-2,3-dihydro-1,3,6-trimethyl-2-oxo-pyrimidinium chloride, 4-(2-[2,4,5-trihydroxy-phenyl]ethenyl]-2,3-dihydro-1,3,6-trimethyl-2-oxo-pyrimidinium chloride, 4-[2-[2,4,6-trihydroxyphenyl]ethenyl]-2,3-dihydro-1,3,6-trimethyl-2-oxo-pyrimidinium hydrogen sulfate, 4-[2-[2,3-dimethoxyphenyl]ethenyl]-2,3-dihydro-1,3,6-trimethyl-2-oxo-pyrimidinium chloride, 4-[2-[2,4-dimethoxyphenyl]ethenyl]-2,3-dihydro-1,3,6-trimethyl-2-oxo-pyrimidinium chloride, 4-[2-[2,5-dimethoxyphenyl]ethenyl]-2,3-dihydro-1,3,6-trimethyl-2-oxo-pyrimidinium chloride, 4-[2-[2,6-dimethoxyphenyl]ethenyl]-2,3-dihydro-1,3,6-trimethyl-2-oxo-pyrimidinium chloride, 4-[2-[3,4-dimethoxyphenyl]ethenyl]-2,3-dihydro-1,3,6-trimethyl-2-oxo-pyrimidinium chloride, 4-[2-[3,5-dimethoxyphenyl]ethenyl]-2, 3-dihydro-1,3,6-trimethyl-2-oxo-pyrimidinium chloride, 4-[2-[3,6-dimethoxyphenyl]ethenyl]-2,3-dihydro-1,3,6-trimethyl-2-oxo-pyrimidinium chloride, 4-[2-[2,3,4-trimethoxyphenyl]ethenyl]-2,3-dihydro-1,3,6-trimethyl-2-oxo-pyrimidinium chloride, 4-[2-[2,3,5-trimethoxyphenyl]ethenyl]-2,3-dihydro-1,3,6-trimethyl-2-oxo-pyrimidinium chloride, 4-[2-[2,3,6-trimethoxyphenyl]ethenyl]-2,3-dihydro-1,3,6-trimethyl-2-oxo-pyrimidinium chloride, 4-[2-[3,4,5-trimethoxyphenyl]ethenyl]-2,3-dihydro-1,3,6-trimethyl-2-oxo-pyrimidinium chloride, 4-[2-[3,4,6-trimethoxyphenyl]ethenyl]-2,3-dihydro-1,3,6-trimethyl-2-oxo-pyrimidinium hydrogen sulfate, 4-[2-[2,4,6-trimethoxyphenyl)ethenyl]-2,3-dihydro-1,3,6-trimethyl-2-oxo-pyrimidinium chloride, 4-[2-[2-hydroxy-3-methoxyphenyl]-ethenyl]-2,3-dihydro-1,3,6-trimethyl-2-oxo-pyrimidinium chloride, 4-[2-[2-hydroxy-4-methoxyphenyl)ethenyl)-2,3-dihydro-1,3,6-trimethyl-2-oxo-pyrimidinium chloride, 4-[2-[2-hydroxy-5-methoxyphenyl]ethenyl]-2,3-dihydro-1,3,6-trimethyl-2-oxo-pyrimidinium chloride, 4-[2-[2-hydroxy-6-methoxyphenyl]ethenyl]-2,3-dihydro-1,3,6-trimethyl-2-oxo-pyrimidinium hydrogen sulfate, 4-[2-[3-hydroxy-2-methoxyphenyl]ethenyl]-2,3-dihydro-1,3,6-trimethyl-2-oxo-pyrimidinium chloride, 4-[2-[4-hydroxy-4-methoxyphenyl]ethenyl]-2,3-dihydro-1,3,6-trimethyl-2-oxo-pyrimidinium hydrogen sulfate, 4-[2-[3-hydroxy-5-methoxyphenyl]ethenyl]-2,3-dihydro-1,3,6-trimethyl-2-oxo-pyrimidinium chloride, 4-[2-3-hydroxy-6-methoxyphenyl]ethenyl]-2,3-dihydro-1,3,6-trimethyl-2-oxo-pyrimidinium hydrogen sulfate, 4-[2-[4-hydroxy-2-methoxyphenyl]ethenyl]-2,3-dihydro-1,3,6-trimethyl-2-oxo-pyrimidinium chloride, 4-[2-[4-hydroxy-3-methoxyphenyl]ethenyl]-2,3-dihydro-1,3,6-trimethyl-2-oxo-pyrimidinium chloride, 4-[2-[2,3-dihydroxy-4-methoxyphenyl]ethenyl]-2,3-dihydro-1,3,6-trimethyl-2-oxo-pyrimidinium chloride, 4-[2-[2,3-dihydroxy-5-methoxyphenyl]ethenyl]-2,3-dihydro-1,3,6-trimethyl-2-oxo-pyrimidinium chloride, 4-[2-[2,3-dihydroxy-6-methoxyphenyl]ethenyl]-2,3-dihydro-1,3,6-trimethyl-2-oxo-pyrimidinium chloride, 4-[2-[2,4-dihydroxy-3-methoxyphenyl]ethenyl]-2,3-dihydro-1,3,6-trimethyl-2-oxo-pyrimidinium chloride, 4-[2-[2,4-dihydroxy-5-methoxyphenyl]ethenyl]-2,3-dihydro-1,3,6-trimethyl-2-oxo-pyrimidinium chloride, 4-[2-[2,4-dihydroxy-6-methoxyphenyl]ethenyl]-2,3-dihydro-1,3,6-trimethyl-2-oxo-pyrimidinium hydrogen sulfate, 4-[2-[2,5-dihydroxy-3-methoxyphenyl]ethenyl]-2,3-dihydro-1,3,6-trimethyl-2-oxo-pyrimidinium hydrogen sulfate, 4-[2-[2,5-dihydroxy-4-methoxyphenyl]ethenyl]-2,3-dihydro-1,3,6-trimethyl-2-oxo-pyrimidinium chloride, 4-[2-[2,5-dihydroxy-6-methoxyphenyl]ethenyl)-2,3-dihydro-1,3,6-trimethyl-2-oxo-pyrimidinium chloride, 4-[2-[2,6-dihydroxy-3-methoxyphenyl]ethenyl)-2,3-dihydro-1,3,6-trimethyl-2-oxo-pyrimidinium chloride, 4-[2-[2,6-dihydroxy-4-methoxyphenyl]ethenyl]-2,3-dihydro-1,3,6-trimethyl-2-oxo-pyrimidinium chloride, 4-[2-[2,6-dihydroxy-5-methoxyphenyl]ethenyl]-2,3-dihydro-1,3,6-trimethyl-2-oxo-pyrimidinium chloride, 4-[2-[2,3-dimethoxy-4-hydroxy-phenyl]ethenyl]-2,3-dihydro-1,3,6-trimethyl-2-oxo-pyrimidinium chloride, 4-[2-[2,3-dimethoxy-5-hydroxyphenyl]ethenyl]-2,3-dihydro-1,3,6-trimethyl-2-oxo-pyrimidinium chloride, 4-[2-[2,3-dimethoxy-6-hydroxy-phenyl]ethenyl]-2,3-dihydro-1,3,6-trimethyl-2-oxo-pyrimidinium chloride, 4-[2-[2,4-dimethoxy-3-hydroxy-phenyl]ethenyl]-2,3-dihydro-1,3,6-trimethyl-2-oxo-pyrimidinium chloride, 4-[2-[2,4-dimethoxy-5-hydroxy-phenyl]ethenyl]-2,3-dihydro-1,3,6-trimethyl-2-oxo-pyrimidinium chloride, 4-[2-[2,4-dimethoxy-6-hydroxy-phenyl]ethenyl]-2,3-dihydro-1,3,6-trimethyl-2-oxo-pyrimidinium chloride, 4-[2-[2,5-dimethoxy-3-hydroxyphenyl]ethenyl]-2,3-dihydro-1,3,6-trimethyl-2-oxo-pyrimidinium chloride, 4-[2-[2,5-dimethoxy-4-hydroxy-phenyl]ethenyl]-2,3-dihydro-1,3,6-trimethyl-2-oxo-pyrimidinium hydrogen sulfate, 4-[2-[2,5-dimethoxy-6-hydroxy-phenyl]ethenyl]-2,3-dihydro-1,3,6-trimethyl-2-oxo-pyrimidinium chloride, 4-[2-[2,6-dimethoxy-3-hydroxy-phenyl]ethenyl]-2,3-dihydro-1,3,6-trimethyl-2-oxo-pyrimidinium hydrogen sulfate, 4-[2-[2,6-dimethoxy-4-hydroxy-phenyl]ethenyl]-2,3-dihydro-1,3,6-trimethyl-2-oxo-pyrimidinium chloride, 4-[2-[2,6-dimethoxy-5-hydroxy-phenyl]ethenyl]-2,3-dihydro-1,3,6-trimethyl-2-oxo-pyrimidinium chloride, 4-[2-[3,4-dimethoxy-3-hydroxy-phenyl]ethenyl]-2,3-dihydro-1,3,6-trimethyl-2-oxo-pyrimidinium hydrogen sulfate, 4-[2-[3,4-dimethoxy-5-hydroxy-phenyl]ethenyl]-2,3-dihydro-1,3,6-trimethyl-2-oxo-pyrimidinium chloride, 4-[2-[3,4-dimethoxy-6-hydroxy-phenyl]-ethenyl]-2,3-dihydro-1,3,6-trimethyl-2-oxo-pyrimidinium hydrogen sulfate, 4-[2-[3,5-dimethoxy-2-hydroxy-phenyl]ethenyl]-2,3-dihydro-1,3,6-trimethyl-2-oxo-pyrimidinium chloride, 4-[2-[3,5-dimethoxy-4-hydroxy-phenyl]ethenyl]-2,3-dihydro-1,3,6-trimethyl-2-oxo-pyrimidinium chloride, 4-[2-[3,5-dimethoxy-6-hydroxy-phenyl]ethenyl]-2,3-dihydro-1,3,6-trimethyl-2-oxo-pyrimidinium chloride, 4-[2-[3,5-dimethyl-4-hydroxy-phenyl]ethenyl)-2,3-dihydro-1,3,6-trimethyl-2-oxo-pyrimidinium chloride, 4-[2-[3,5-dimethyl-2-hydroxy-phenyl]-ethenyl]-2,3-dihydro-1,3,6-trimethyl-2-oxo-pyrimidinium chloride, 4-[2-[4-(dimethylamino)-2-hydroxyphenyl]ethenyl]-2,3-dihydro-1,3,6-trimethyl-2-oxo-pyrimidinium chloride, 4-[2-[4-(dimethylamino)-3-hydroxyphenyl]ethenyl]-2,3-dihydro-1,3,6-trimethyl-2-oxo-pyrimidinium chloride, 4-[2-[4-(diethylamino)-2-hydroxyphenyl]ethenyl]-2,3-dihydro-1,3,6-trimethyl-2-oxo-pyrimidinium chloride, 4-[2-[4-(diethylamino)-3-hydroxyphenyl]ethenyl]-2,3-dihydro-1,3,6-trimethyl-2-oxo-pyrimidinium chloride, 4-[2-[4-(diethylamino)-2-methylphenyl]ethenyl]-2,3-dihydro-1,3,6-trimethyl-2-oxo-pyrimidinium chloride, 4-[2-[4-(diethylamino)-3-methylphenyl]-ethenyl]-2,3-dihydro-1,3,6-trimethyl-2-oxo-pyrimidinium chloride, 4-[2-[2-hydroxy-naphth-1-yl]ethenyl]-2,3-dihydro-1,3,6-trimethyl-2-oxo-pyrimidinium chloride, 4-[2-[3-hydroxy-naphth-1-yl]ethenyl]-2,3-dihydro-1,3,6-trimethyl-2-oxo-pyrimidinium chloride, 4-[2-[4-hydroxynaphth-1-yl]ethenyl]-2,3-dihydro-1,3,6-trimethyl-2-oxo-pyrimidinium chloride, 4-[2-[2-methoxy]-2,3-dihydro-1,3,6-trimethyl-2-oxopyrimidinium chloride, 4-[2-[3-methoxynaphth-1-yl]ethenyl]-2,3-dihydro-1,3,6-trimethyl-2-oxopyrimidinium chloride, 4-[2-[4-methoxynaphth-1-yl]ethenyl]-2,3-dihydro-1,3,6-trimethyl-2-oxopyrimidinium chloride, 4-[2-[4-(dimethylamino)naphth-1-yl]ethenyl]-2,3-dihydro-1,3,6-trimethyl-2-oxo-pyrimidinium hydrogen sulfate, 4-[2-[4-(diethylamino)-naphth-1-yl]ethenyl]-2,3-dihydro-1,3,6-trimethyl-2-oxo-pyrimidinium chloride, 4,6-bis[2-[2-hydroxyphenyl]ethenyl]-2,3-dihydro-1,3-dimethyl-2-oxo-pyrimidinium chloride, 4,6-bis[2-[3-hydroxyphenyl]ethenyl]-2,3-dihydro-1,3-dimethyl-2-oxo-pyrimidinium chloride, 4,6-bis[2-[4-hydroxyphenyl]ethenyl]-2,3-dihydro-1,3-dimethyl-2-oxo-pyrimidinium chloride, 4,6-bis[2-[2,3-dihydroxyphenyl]ethenyl]-2,3-dihydro-1,3-dimethyl-2-oxo-pyrimidinium hydrogen sulfate, 4,6-bis[2-[2,4-dihydroxyphenyl]ethenyl]-2,3-dihydro-1,3-dimethyl-2-oxo-pyrimidinium chloride, 4,6-bis[2-[2,5-dihydroxyphenyl]ethenyl]-2,3-dihydro-1,3-dimethyl-2-oxo-pyrimidinium chloride, 4,6-bis[2-[2,6-dihydroxyphenyl]ethenyl]-2,3-dihydro-1,3-dimethyl-2-oxo-pyrimidinium hydrogen sulfate, 4,6-bis[2-[3,4-dihydroxyphenyl]ethenyl]-2,3-dihydro-1,3-dimethyl-2-oxo-pyrimidinium chloride, 4,6-bis[2-[3,5-dihydroxyphenyl]ethenyl]-2,3-dihydro-1,3-dimethyl-2-oxo-pyrimidinium hydrogen sulfate, 4,6-bis[2-[3,6-dihydroxyphenyl]ethenyl]-2,3-dihydro-1,3-dimethyl-2-oxo-pyrimidinium chloride, 4,6-bis[2-[2,3,4-trihydroxyphenyl]ethenyl]-2,3-dihydro-1,3-dimethyl-2-oxo-pyrimidinium chloride, 4,6-bis[2-[2,3,5-trihydroxyphenyl)ethenyl]-2,3-dihydro-1,3-dimethyl-2-oxo-pyrimidinium chloride, 4,6-bis[2-[2,3,6-trihydroxyphenyl]ethenyl]-2,3-dihydro-1,3-dimethyl-2-oxo-pyrimidinium chloride, 4,6-bis[2-[3,4,5-trihydroxyphenyl]ethenyl]-2,3-dihydro-1,3-dimethyl-2-oxo-pyrimidinium chloride, 4,6-bis[2-[2,4,6-trihydroxyphenyl]ethenyl]-2,3-dihydro-1,3-dimethyl-2-oxo-pyrimidinium chloride, 4,6-bis[2-[2-methoxyphenyl]ethenyl]-2,3-dihydro-1,3-dimethyl-2-oxo-pyrimidinium chloride, 4,6-bis[2-[3-methoxyphenyl]ethenyl]-2,3-dihydro-1,3-dimethyl-2-oxo-pyrimidinium chloride, 4,6-bis[2-[4-methoxyphenyl]ethenyl]-2,3-dihydro-1,3-dimethyl-2-oxo-pyrimidinium chloride, 4,6-bis[2-[2-hydroxy-3-methoxyphenyl]ethenyl]-2,3-dihydro-1,3-dimethyl-2-oxopyrimidinium chloride, 4,6-bis[2-[2-hydroxy-4-methoxyphenyl]ethenyl]-2,3-dihydro-1,3-dimethyl-2-oxo-pyrimidinium chloride, 4,6-bis[2-[2-hydroxy-5-methoxyphenyl]ethenyl]-2,3-dihydro-1,3-dimethyl-2-oxo-pyrimidinium chloride, 4,6-bis[2-[2-hydroxy-6-methoxyphenyl]ethenyl]-2,3-dihydro-1,3-dimethyl-2-oxo-pyrimidinium chloride, 4,6-bis[2-[2-hydroxy-3,4-dimethoxyphenyl]ethenyl]-2,3-dihydro-1,3-dimethyl-2-oxo-pyrimidinium chloride, 4,6-bis[2-[2-hydroxy-3,5-dimethoxyphenyl]ethenyl]-2,3-dihydro-1,3-dimethyl-2-oxo-pyrimidinium chloride, 4,6-bis[2-[2-hydroxy-3,6-methoxyphenyl]ethenyl]-2,3-dihydro-1,3-dimethyl-2-oxo-pyrimidinium chloride, 4,6-bis[2-[3-hydroxy-2,4-dimethoxyphenyl]ethenyl]-2,3-dihydro-1,3-dimethyl-2-oxo-pyrimidinium chloride, 4,6-bis[2-[3-hydroxy-2,5-dimethoxyphenyl)ethenyl]-2,3-dihydro-1,3-dimethyl-2-oxo-pyrimidinium chloride, 4,6-bis[2-[3-hydroxy-2,6-dimethoxyphenyl]ethenyl]-2,3-dihydro-1,3-dimethyl-2-oxo-pyrimidinium chloride, 4,6-bis[2-[4-hydroxy-2,3-dimethoxyphenyl]ethenyl]-2,3-dihydro-1,3-dimethyl-2-oxo-pyrimidinium chloride, 4,6-bis[2-[4-hydroxy-2,5-dimethoxyphenyl]ethenyl]-2,3-dihydro-1,3-dimethyl-2-oxo-pyrimidinium chloride, 4,6-bis[2-[4-hydroxy-2,6-dimethoxyphenyl]ethenyl]-2,3-dihydro-1,3-dimethyl-2-oxo-pyrimidinium chloride, 4,6-bis[2-[4-hydroxy-3,5-dimethoxyphenyl]ethenyl]-2,3-dihydro-1,3-dimethyl-2-oxo-pyrimidinium chloride, 4,6-bis[2-[4-(diethylamino)phenyl]ethenyl]-2,3-dihydro-1,3-dimethyl-2-oxo-pyrimidinium chloride and 4,6-bis[2-[4-(diethylamino)-2-hydroxyphenyl]ethenyl]-2,3-dihydro-1,3-dimethyl-2-oxo-pyrimidinium chloride.

The above cited compounds of Formula 1, the compounds of component B, the compounds of component C and the reaction products RP are each preferably used in an amount from 0.03 to 65 mmol, particularly from 1 to 40 mmol based on 100 g of the total colorant.

In a fourth embodiment, the inventive agents comprise, besides at least one compound according to Formula I and at least one reactive carbonyl compound, at least one developer component and optionally one coupler component as oxidation dyestuff precursor.

According to the invention, it can be preferred to use a p-phenylenediamine derivative or one of its physiologically compatible salts as the developer component p-Phenylenediamine derivatives of formula (E1) are particularly preferred

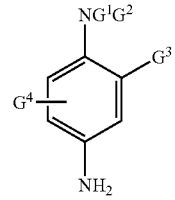

(E1)

wherein
$G^1$ stands for a hydrogen atom, a $C_1$ to $C_4$ alkyl radical, a $C_1$ to $C_4$ monohydroxyalkyl radical, a $C_2$ to $C_4$ polyhydroxyalkyl radical, a ($C_1$ to $C_4$)-alkoxy-($C_1$ to $C_4$)-alkyl radical, a 4'-aminophenyl radical or a $C_1$ to $C_4$ alkyl radical substituted by a nitrogen-containing group, a phenyl radical or a 4'-aminophenyl radical;

$G^2$ stands for a hydrogen atom, a $C_1$ to $C_4$ alkyl radical, a $C_1$ to $C_4$ monohydroxyalkyl radical, a $C_2$ to $C_4$ polyhydroxyalkyl radical, a ($C_1$ to $C_4$)-alkoxy-($_1$ to $C_4$)-alkyl radical or a $C_1$ to $C_4$ alkyl radical substituted by a nitrogen-containing group;

$G^3$ stands for a hydrogen atom, a halogen atom, such as a chlorine, bromine, iodine or fluorine atom, a $C_1$ to $C_4$ alkyl radical, a $C_1$ to $C_4$ monohydroxyalkyl radical, a $C_2$ to $C_4$ polyhydroxyalkyl radical, a $C_1$ to $C_4$ hydroxyalkoxy radical, a $C_1$ to $C_4$ acetylaminoalkoxy radical, a $C_1$ to $C_4$ mesylaminoalkoxy radical or a $C_1$ to $C_4$ carbamoylaminoalkoxy radical;

$G^4$ is a hydrogen atom, a halogen atom or a $C_1$ to $C_4$ alkyl radical or if $G^3$ and $G^4$ are in the ortho position to one another, they may together form a bridging α,ω-alkylenedioxo group such as, for example, an ethylenedioxy group.

Examples of substituents of the cited $C_1$ to $C_4$ alkyl radicals in the inventive compounds are the methyl, ethyl, propyl, isopropyl and butyl groups. Ethyl and methyl are preferred alkyl radicals. According to the invention, preferred $C_1$ to $C_4$ alkoxy radicals are, for example, methoxy or ethoxy groups. In addition, preferred examples of a $C_1$ to $C_4$ hydroxyalkyl group can be cited as a hydroxymethyl, a 2-hydroxyethyl, a 3-hydroxypropyl or a 4-hydroxybutyl group. A 2-hydroxyethyl group is particularly preferred. A particularly preferred $C_2$ to $C_4$ polyhydroxyalkyl group is the 1,2-dihydroxyethyl group. According to the invention, examples of halogen atoms are F, Cl or Br atoms, Cl atoms are quite particularly preferred. According to the invention, the terms used later are derived from the definitions given here. Examples of nitrogen-containing groups of formula (E1) are particularly the amino groups, $C_1$ to $C_4$ monoalkylamino groups, $C_1$ to $C_4$ dialkylamino groups, $C_1$ to $C_4$ trialkylamino groups, $C_1$ to $C_4$ monohydroxyalkylamino groups, imadazolinium and ammonium.

Particularly preferred p-phenylenediamines of formula (E1) are selected from p-phenylenediamine, p-toluylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)-aniline, N,N-bis-(β-hydroxyethyl)-p-phenylenediamine, 4-N,N-bis-(β-hydroxyethyl)-amino-2-methylaniline, 4-N,N-bis-(β-hydroxyethyl)amino-2-chloroaniline, 2-(β-hydroxyethyl)-p-phenylenediamine, 2-fluoro-p-phenylenediamine, 2-isopropyl-p-phenylenediamine, N-(β-hydroxypropyl)-p-phenylenediamine, 2-hydroxymethyl-p-phenylenediamine, N,N-dimethyl-3-methyl-p-phenylenediamine, N,N-(ethyl-β-hydroxyethyl)-p-phenylenediamine, N-(β,γ-dihydroxypropyl)-p-phenylenediamine, N-(4'-aminophenyl)-p-phenylenediamine, N-phenyl-p-phenylenediamine, 2-(β-hydroxyethyloxy)-p-phenylenediamine, 2-(β-acetylaminoethyloxy)-p-phenylenediamine, N-(β-methoxyethyl)-p-phenylenediamine and 5,8-diaminobenzo-1,4-dioxane and their physiologically compatible salts.

According to the invention, quite particularly preferred p-phenylenediamine derivatives corresponding to formula (E1) are p-phenylenediamine, p-toluylenediamine, 2-(β-hydroxyethyl)-p-phenylenediamine and N,N-bis(β-hydroxyethyl)-p-phenylenediamine.

According to the invention, it can be further preferred to use developer components that are compounds comprising at least two aromatic nuclei substituted by amino and/or hydroxyl groups.

The binuclear developer components, which may be used in the coloring compositions according to the invention, include in particular compounds corresponding to formula (E2) as well as their physiologically compatible salts:

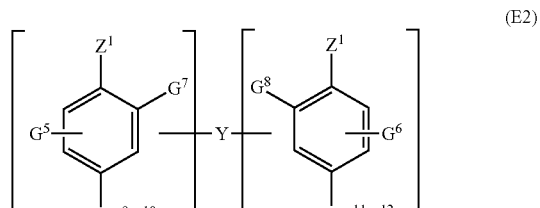

(E2)

in which:
- $Z^1$ and $Z^2$ independently of one another stand for a hydroxyl or $NH_2$ radical which is optionally substituted by a $C_1$ to $C_4$ alkyl radical, by a $C_1$ to $C_4$ hydroxyalkyl radical and/or by a bridging group Y or which is optionally part of a bridging ring system,
- the bridging group Y is an alkylene group with 1 to 14 carbon atoms, such as, for example, a linear or branched alkylene chain or an alkylene ring which may be interrupted or terminated by one or more nitrogen-containing groups and/or one or more hetero atoms, such as oxygen, sulfur or nitrogen atoms, and may optionally be substituted by one or more hydroxyl or $C_1$ to $C_8$ alkoxy radicals or is a direct bond,
- $G^5$ and $G^6$ independently of one another stand for a hydrogen or halogen atom, a $C_1$ to $C_4$ alkyl radical, a $C_1$ to $C_4$ monohydroxyalkyl radical, a $C_2$ to $C_4$ polyhydroxyalkyl radical, a $C_1$ to $C_4$ aminoalkyl radical or a direct bond to the bridging group Y,
- $G^7$, $G^8$, $G^9$, $G^{10}$, $G^{11}$ and $G^{12}$ independently of one another stand for a hydrogen atom, a direct bond to the bridging group Y or a $C_1$ to $C_4$ alkyl radical, with the provisos that
- the compounds of formula (E2) contain only one bridging group Y per molecule and
- the compounds of formula (E2) contain at least one amino group that carries at least one hydrogen atom.

According to the invention, the substituents used in formula (E2) are as defined in the foregoing embodiments.

Preferred binuclear primary intermediates corresponding to formula (E2) are, in particular, N,N'-bis-(β-hydroxyethyl)-N,N'-bis-(4'-aminophenyl)-1,3-diaminopropan-2-ol, N,N'-bis-(β-hydroxyethyl)-N,N'-bis-(4'-aminophenyl)-ethylenediamine, N,N'-bis-(4-aminophenyl)tetramethylenediamine, N,N'-bis-(β-hydroxyethyl)-N,N'-bis-(4'-aminophenyl)tetramethylenediamine, N,N'-bis-(4-methylaminophenyl)tetramethylenediamine, N,N'-bis-(ethyl)-N,N'-bis-(4'-amino-3'-methylphenyl)ethylenediamine, bis-(2-hydroxy-5-aminophenyl)methane, 1,4-bis-(4'-aminophenyl)diazacycloheptane, N,N'-bis-(2-hydroxy-5-aminobenzyl)-piperazine, N-(4'-aminophenyl)-p-phenylenediamine and 1,10-bis-(2',5'-diaminophenyl)-1,4,7,10-tetraoxadecane and their physiologically compatible salts.

Quite particularly preferred binuclear developer components of formula (E2) are N,N'-bis-(β-hydroxyethyl)-N,N'-bis-(4'-aminophenyl)-1,3-diaminopropan-2-ol, bis-(2-hydroxy-5-aminophenyl)methane, N,N'-bis-(4'-aminophenyl)-1,4-diazacycloheptane and 1,10-bis-(2',5'-diaminophenyl)-1,4,7,10-tetraoxadecane or one of their physiologically compatible salts.

According to the invention, it can be further preferred to use a p-aminophenol derivative or one of its physiologically compatible salts as the developer component. p-Aminophenol derivatives of formula (E3) are particularly preferred

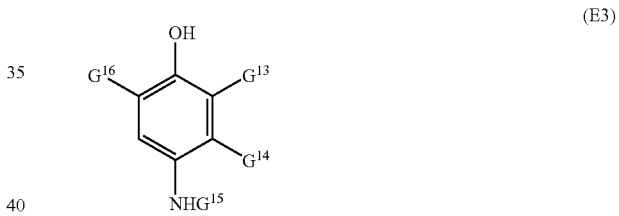

(E3)

in which:
- $G^{13}$ stands for a hydrogen atom, a halogen atom, a $C_1$ to $C_4$ alkyl radical, a $c_1$ to $C_4$ monohydroxyalkyl radical, a $C_2$ to $C_4$ polyhydroxyalkyl radical, a ($C_1$ to $C_4$)-alkoxy-($C_1$ to $C_4$)-alkyl radical, a $C_1$ to $C_4$ aminoalkyl radical, a hydroxy-($C_1$ to $C_4$)-alkylamino radical, a $C_1$ to $C_4$ hydroxyalkyoxy radical, a $C_1$ to $C_4$ hydroxyalkyl-($C_1$ to $C_4$)-aminoalkyl radical or a (di-$C_1$ to $C_4$ alkylamino)-($C_1$ to $C_4$)-alkyl radical, and
- $G^{14}$ stands for a hydrogen atom or a halogen atom, a $C_1$ to $C_4$ alkyl radical, a $C_1$ to $C_4$ monohydroxyalkyl radical, a $C_2$ to $C_4$ polyhydroxyalkyl radical, a ($C_1$ to $C_4$)-alkoxy-($C_1$ to $C_4$)-alkyl radical, a $C_1$ to $C_4$ aminoalkyl radical or a $C_1$ to $C_4$ cyanoalkyl radical,
- $G^{15}$ stands for hydrogen, a $C_1$ to $C_4$ alkyl radical, a $C_1$ to $C_4$ monohydroxyalkyl radical, a $C_2$ to $C_4$ polyhydroxyalkyl radical, a phenyl radical or a benzyl radical and
- $G^{16}$ stands for hydrogen or a halogen atom.

According to the invention, the substituents used in formula (E3) are defined as in the foregoing embodiments.

Preferred p-aminophenols of Formula (E3) are, in particular, p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(2-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-(α,β-dihydroxyethyl)phenol, 4-amino-2-fluorophenol, 4-amino-2-chlorophenol, 2,6-dichloro-4-aminophenol, 4-amino-2-(diethylaminomethyl)phenol and their physiologically compatible salts.

Quite particularly preferred compounds corresponding to formula (E3) are p-aminophenol, 4-amino-3-methylphenol, 4-amino-2-aminomethylphenol, 4-amino-2-(α,β-dihydroxyethyl)phenol and 4-amino-2-(diethylaminomethyl)phenol.

The developer component may also be selected from o-aminophenol and derivatives thereof such as, for example, 2-amino-4-methylphenol, 2-amino-5-methylphenol or 2-amino-4-chlorophenol.

The developer component may also be selected from heterocyclic developer components such as, for example, the pyridine, pyrimidine, pyrazole, pyrazole-pyrimidine derivatives and physiologically compatible salts thereof.

Preferred pyridine derivatives are particularly the compounds described in the patents GB 1 026 978 and GB 1 153 196, such as 2,5-diaminopyridine, 2-(4'-methoxyphenyl) amino-3-aminopyridine, 2,3-diamino-6-methoxypyridine, 2-(β-methoxyethyl)amino-3-amino-6-methoxypyridine and 3,4-diaminopyridine.

Preferred pyrimidine derivatives are, in particular, the compounds described in German patent DE 2 359 399, Japanese laid-open patent JP 02019576 A2 or the laid-open patent WO 96/15765, such as 2,4,5,6-tetraminopyrimidine, 4-hydroxy-2,5,6-triaminopyrimidine, 2-hydroxy-4,5,6-triaminopyrimidine, 2-dimethylamino-4,5,6-triamino-pyrimidine, 2,4-dihydroxy-5,6-diaminopyrimidine and 2,5,6-triaminopyrimidine.

Preferred pyrazole derivatives are, in particular, the compounds described in the patents DE 3 843 892, DE 4 133 957 and patent applications WO 94/08969, WO 94/08970, EP 740 931 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert.butyl-1-methylpyrazole, 4,5-diamino-1-tert.butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)-amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)-amino-1-methylpyrazole.

Preferred pyrazole-pyrimidine derivatives are, in particular, the derivatives of pyrazole-[1,5-a]-pyrimidine corresponding to formula (E4) below and tautomeric forms thereof, in so far that a tautomeric equilibrium exists:

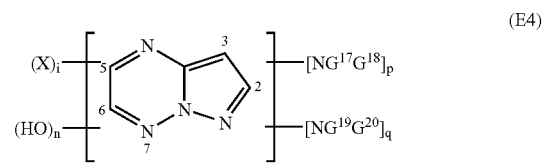

in which:
G$^{17}$, G$^{18}$, G$^{19}$ and G$^{20}$ independently of one another stand for a hydrogen atom, a C$_1$ to C$_4$ alkyl radical, an aryl radical, a C$_1$ to C$_4$ hydroxyalkyl radical, a C$_2$ to C$_4$ polyhydroxyalkyl radical, a (C$_1$ to C$_4$)-alkoxy-(C$_1$ to C$_4$)-alkyl radical, a C$_1$ to C$_4$ aminoalkyl radical which may optionally be protected by an acetylureido or sulfonyl radical, a (C$_1$ to C$_4$)-alkylamino-(C$_1$ to C$_4$)-alkyl radical, a di[(C$_1$ to C$_4$)-alkyl]-(C$_1$ to C$_4$)-aminoalkyl radical, the dialkyl radicals optionally forming a carbon cycle or a heterocycle with 5 or 6 members, a C$_1$ to C$_4$ hydroxyalkyl or a di-(C$_1$ to C$_4$)-[hydroxyalkyl]-(C$_1$ to C$_4$)-aminoalkyl radical;
the X radicals independently of one another stand for a hydrogen atom, a C$_1$, to C$_4$ alkyl radical, an aryl radical, a C$_1$ to C$_4$ hydroxyalkyl radical, a C$_2$ to C$_4$ polyhydroxyalkyl radical, a C$_1$ to C$_4$ aminoalkyl radical, a (C$_1$ to C$_4$)-alkylamino-(C$_1$ to C$_4$)-alkyl radical, a di[(C$_1$ to C$_4$)-alkyl]-(C$_1$ to C$_4$)-aminoalkyl radical, the dialkyl radicals optionally forming a carbon cycle or a heterocycle with 5 or 6 members, a C$_1$ to C$_4$ hydroxyalkyl or a di-(C$_1$ to C$_4$)-[hydroxyalkyl]-(C$_1$ to C$_4$)-aminoalkyl radical, an amino radical, a C$_1$ to C$_4$ alkyl or a di-(C$_1$ to C$_4$-hydroxyalkyl)-amino radical, a halogen atom, a carboxylic acid group or a sulfonic acid group,
i has the value 0, 1, 2 or 3,
p has the value 0 or 1,
q has the value 0 or 1 and
n has the value 0 or 1,
with the proviso that
the sum of p+q is not 0,
when p+q=2, n has the value 0 and the groups NG$^{17}$G$^{18}$ and NG$^{19}$G$^{20}$ occupy the (2,3); (5,6); (6,7); (3,5) or (3,7) positions;
when p+q=1, n has the value 1 and the groups NG$^{17}$G$^{18}$ (or NG$^{19}$G$^{20}$) and the group OH occupy the (2,3); (5,6); (6,7); (3,5) or (3,7) positions;
According to the invention, the substituents used in formula (E4) are as defined in the foregoing embodiments.
If the pyrazole-[1,5-a]-pyrimidine corresponding to formula (E4) above contains a hydroxyl group in one of the positions 2, 5 or 7 of the ring system, a tautomeric equilibrium exists as illustrated, for example, in the following scheme:

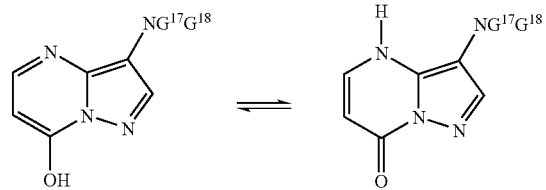

Among the pyrazole-[1,5-a]-pyrimidines corresponding to formula (E4) above, the following may be particularly mentioned:
pyrazole-[1,5-a]-pyrimidine-3,7-diamine;
2,5-dimethylpyrazole-[1,5-a]-pyrimidine-3,7-diamine;
pyrazole-[1,5-a]-pyrimidine-3,5-diamine;
2,7-dimethylpyrazole-[1,5-a]-pyrimidine-3,5-diamine;
3-aminopyrazole-[1,5-a]-pyrimidin-7-ol;
3-aminopyrazole-[1,5-a]-pyrimidin-5-ol;
2-(3-aminopyrazole-[1,5-a]-pyrimidin-7-ylamino)ethanol;
2-(7-aminopyrazole-[1,5-a]-pyrimidin-3-ylamino)ethanol;
2-[(3-aminopyrazole-[1,5-a]-pyrimidin-7-yl)-(2-hydroxyethyl)amino]ethanol;
2-[(7-aminopyrazole-[1,5-a]-pyrimidin-3-yl)-(2-hydroxyethyl)amino]ethanol;
5,6-dimethylpyrazole-[1,5-a]-pyrimidine-3,7-diamine;
2,6-dimethylpyrazole-[1,5-a]-pyrimidine-3,7-diamine;
3-amino-7-dimethylamino-2,5-dimethylpyrazole-[1,5-a]-pyrimidine;

as well as their physiologically compatible salts and their tautomeric forms if a tautomeric equilibrium exists.

The pyrazole-[1,5-a]-pyrimidines corresponding to Formula (E4) above may be prepared by cyclization starting from an aminopyrazole or from hydrazine, as described in the literature.

Coupler components optionally comprised in the inventive agents are preferably selected from m-aminophenol and derivatives thereof such as, for example, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-(diethylamino)phenol, N-cyclopentyl-3-aminophenol, 1,3-dihydroxy-5-(methylamino)benzene, 3-(ethylamino)-4-methylphenol and 2,4-dichloro-3-aminophenol, o-aminophenol and derivatives thereof, m-diaminobenzene and derivatives thereof such as, for example, 2,4-diaminophenoxyethanol, 1,3-bis-(2',4'-diaminophenoxy)propane, 1-methoxy-2-amino-4-(2'-hydroxyethylamino)benzene, 1,3-bis-(2',4'-diaminophenyl)propane, 2,6-bis-(2'-hydroxyethylamino)-1-methylbenzene and 1-amino-3-bis-(2'-hydroxyethyl)aminobenzene, o-diaminobenzene and derivatives thereof such as, for example, 3,4-diaminobenzoic acid and 2,3-diamino-1-methylbenzene, di- and trihydroxybenzene derivatives such as, for example, resorcinol, resorcinol monomethyl ether, 2-methyl resorcinol, 5-methyl resorcinol, 2,5-dimethyl resorcinol, 2-chlororesorcinol, 4-chlororesorcinol, pyrogallol and 1,2,4-trihydroxybenzene, pyridine derivatives such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine and 3,5-diamino-2,6-dimethoxypyridine, naphthalene derivatives such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihdroxynaphthalene, 1,7-dihydroxy-naphthalene, 1,8-dihydroxynaphthalene, 2,7-dihdroxynaphthalene and 2,3-dihdroxynaphthalene, morpholine derivatives such as, for example, 6-hydroxybenzomorpholine and 6-aminobenzomorpholine, quinoxaline derivatives such as, for example, 6-methyl-1,2,3,4-tetrahydroquinoxaline, pyrazole derivatives such as, for example, 1-phenyl-3-methylpyrazol-5-one, indole derivatives such as, for example, 4-hydroxyindole, 6-hydroxyindole and 7-hydroxyindole, pyrimidine derivatives such as, for example, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine or methylenedioxybenzene derivatives such as, for example, 1-hydroxy-3,4-methylenedioxybenzene, 1-amino-3,4-methylene-dioxybenzene and 1-(2'-hydroxyethyl)-amino-3,4-methylene-dioxybenzene.

According to the invention, particularly preferred coupling components are 1-naphthol, 1,5-, 2,7- and 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methylresorcinol, 2,5-dimethylresorcinol and 2,6-dihydroxy-3,4-dimethylpyridine.

In the scope of a fifth embodiment of the present invention, it can be further preferred to add to the inventive agents precursors of a natural dyestuff analog such as indoles and/or indolines which contain at least one hydroxyl or amino group, preferably as a substituent on the six-membered ring. These groups may carry further substituents, for example in the form of an etherified or esterified hydroxyl group or an alkylated amino group. In a second preferred embodiment, the colorants comprise at least one indole and/or indoline derivative.

Derivatives of 5,6-dihydroxyindoline of Formula Xa are particularly good as precursors of natural hair dyestuff analogs,

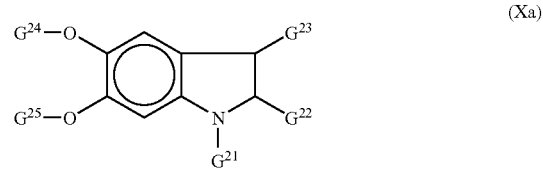

(Xa)

in which, independently of one another
$G^{21}$ is hydrogen, a $C_1$–$C_4$ alkyl group or a $C_1$–$C_4$ hydroxyalkyl-group,
$G^{22}$ is hydrogen or a —COOH group, the —COOH group optionally being present as a salt with a physiologically compatible cation,
$G^{23}$ is hydrogen or a $C_1$–$C_4$ alkyl group,
$G^{24}$ is hydrogen, a $C_1$–$C_4$ alkyl group or a group —CO-$G^{26}$, where
$G^{26}$ is a $C_1$–$C_4$ alkyl group, and
$G^{25}$ is one of the groups mentioned for $G^{24}$, and physiologically compatible salts of these compounds with an organic or inorganic acid.

Particularly preferred derivatives of indoline are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid and 6-hydroxyindoline, 6-aminoindoline and 4-aminoindoline.

Within this group, particular emphasis is placed on N-methyl-5,6-dihydroxyindoline, N-ethyl-5,6-dihydroxyindoline, N-propyl-5,6-dihydroxyindoline, N-butyl-5,6-dihydroxyindoline and, in particular 5,6-dihydroxyindoline. Other particularly suitable precursors of natural hair-dye analogs are derivatives of 5,6-dihydroxyindole corresponding to formula (IIIb):

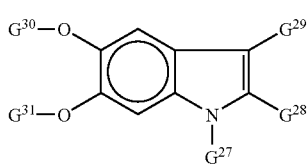
(Xb)

in which, independently of one another
$G^{27}$ is hydrogen, a $C_1$–$C_4$ alkyl group or a $C_1$–$C_4$ hydroxyalkyl group,
$G^{28}$ is hydrogen or a —COOH group, the —COOH group optionally being present as a salt with a physiologically compatible cation,
$G^{29}$ is hydrogen or a $C_1$–$C_4$ alkyl group,
$G^{30}$ is hydrogen, a $C_1$–$C_4$ alkyl group or a group —CO-$G^{32}$, where $G^{32}$ is a $C_1$–$C_4$ alkyl group, and
$G^{31}$ is one of the groups mentioned for $G^{30}$, and
physiologically compatible salts of these compounds with an organic or inorganic acid.

Particularly preferred derivatives of indole are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminoindole.

Within this group, particular emphasis is placed on N-methyl-5,6-dihydroxyindole, N-ethyl-5,6-dihydroxyindole, N-propyl-5,6-dihydroxyindole, N-butyl-5,6-dihydroxyindole and, in particular, 5,6-dihydroxyindole.

The indoline and indole derivatives may be used in the colorants according to the invention both as free bases and in the form of their physiologically compatible salts with inorganic or organic acids, for example, hydrochlorides, sulfates and hydrobromides. The indole or indoline derivatives are normally present in these colorants in amounts of 0.05–10 wt. %, preferably 0.2–5 wt. %.

In a sixth embodiment of the present invention, the inventive hair colorants may comprise, besides the comprised inventive compounds, additional typical substantive dyes for modifying the shades such as nitrophenylenediamines, nitroaminophenols, azo dyes, anthraquinones or indophenols. Preferred substantive dyes are the compounds known under the international names or commercial names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red. 57:1, HC Blue 2, HC Blue 12, Disperse Blue 3, Acid Blue 7, Acid Green 50, HC Violet 1, Disperse Violet 1, Disperse Violet 4, Acid Violet 43, Disperse. Black 9, Acid Black 1 and Acid Black 52 as well as 1,4-diamino-2-nitrobenzene, 2-amino-4-nitrophenol, 1,4-bis-(β-hydroxyethyl)amino-2-nitrobenzene, 3-nitro-4-(β-hydroxyethyl)aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)-amino-5-chloro-2-nitrobenzene, 4-amino-3-nitrophenol, 1-(2'-ureidoethyl)-amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-1-hydroxy-4-nitrobenzene.

Moreover, according to the invention, the inventive compositions may comprise a cationic substantive dye. Particularly preferred thereby are (a) cationic triphenylmethane dyestuffs such as, for example, Basic Blue 7, Basic Blue 26, Basic Violet 2 and Basic Violet 14, (b) aromatic systems substituted by a quaternary nitrogen group such as, for example, Basic Yellow 57, Basic Red 76, Basic Blue 99, Basic Brown 16 and Basic Brown 17 and (c) substantive dyestuffs containing a heterocycle with at least one quaternary nitrogen atom, such as, for example, those explicitly referred to in claims 6 to 11 of EP-A2 998 908.

Preferred cationic substantive dyes of group (c) are, in particular, the following compounds:

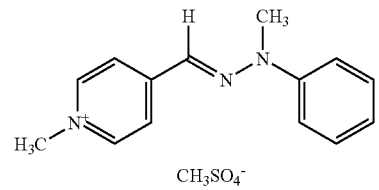
(DZ1) (Basic Yellow 87)

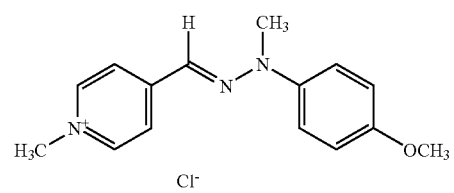
(DZ2)

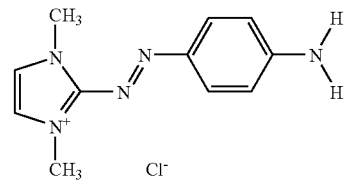
(DZ3) (Basic Orange 31)

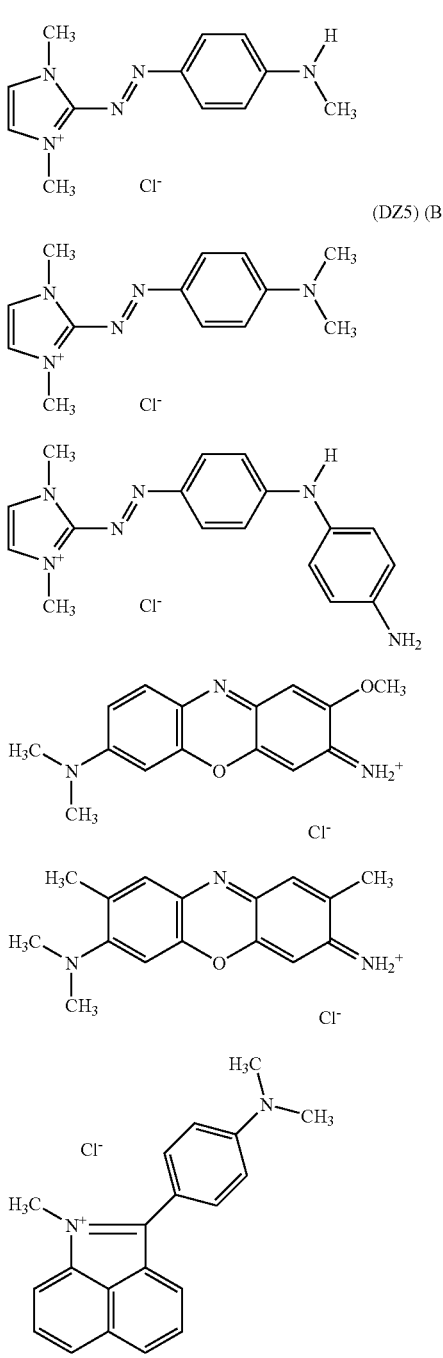

The compounds corresponding to formulae (DZ1), (DZ3) and (DZ5), are quite particularly preferred cationic substantive dyestuffs of group (c). The cationic substantive dyestuffs commercialized under the name Arianor® are particularly preferred substantive dyestuffs according to the invention.

The inventive compositions according to this embodiment preferably comprise the substantive dyes in a quantity of 0.01 to 20 wt. %, based on the total colorant.

The preparations according to the invention may also contain naturally occurring dyestuffs such as, for example, henna red, henna neutral, henna black, camomile blossom, sandalwood, black tea, black alder bark, sage, logwood, madder root, catechu, cedar and alkanet root.

It is not necessary for the optionally comprised substantive dyes to each represent homogeneous compounds. Rather, it is possible that because of the synthetic procedures for the individual dyestuffs, further components are present in minor amounts in the inventive colorants, provided that these do not adversely affect the coloration result, or have to be excluded for other reasons, e.g. toxicological grounds.

To obtain further and more intensive colorations the inventive agents can comprise additional color boosters. The color boosters are advantageously selected from the group consisting of piperidine, piperidine-2-carboxylic acid, piperidine-3-carboxylic acid, piperidine-4-carboxylic acid, pyridine, 2-hydroxypyridine, 3-hydroxypyridine, 4-hydroxypyridine, imidazole, 1-methylimidazole, arginine, histidine, pyrrolidine, proline, pyrrolidone, pyrrolidone-5-carboxylic acid, pyrazole, 1,2,4-triazole, piperazidine, their derivatives and their physiologically compatible salts.

The above named color boosters can each be used in a quantity of 0.03 to 65 mmol, particularly 1 to 40 mmol, each based on 100 g of the total colorant.

The presence of oxidizing agents, e.g. $H_2O_2$ can be avoided, particularly if the inventive agent does not contain any oxidation dyestuff precursors. If the inventive agent contains air-oxidizable oxidation dyestuff precursors or indole or indoline derivatives, then in such a case the oxidizing agents can be avoided without problem. Under certain circumstances, however, it may be desirable to add hydrogen peroxide or other oxidizing agents to the inventive agents in order to achieve shades that are lighter than the keratin-containing fibers that are being dyed. Oxidizing agents are generally added in an amount from 0.01 to 6 wt. % based on the application solution. A preferred oxidizing agent for human hair is $H_2O_2$. Mixtures of a plurality of oxidizing agents, such as, for example a combination of hydrogen peroxide and peroxydisulfates of the alkali- and earth alkali metals or from iodide ion sources, such as, for example alkali metal iodides and hydrogen peroxide or the above-cited peroxydisulfates can also be used. According to the invention, the oxidizing agent and the oxidizing agent combination can be used in combination with oxidation catalysts in the hair colorant. Exemplary oxidation catalysts are metal salts, metal chelate complexes or metal oxides, which enable a facile transition between two oxidation states of the metal ions. Examples are salts, chelate complexes or oxides of iron, ruthenium, manganese and copper. Other possible oxidation catalysts are enzymes. Suitable enzymes are e.g. peroxidases, which can markedly enhance the effect of minor amounts of hydrogen peroxide. According to the invention, such enzymes are moreover suited to directly oxidize the oxidation dyestuff precursors with oxygen in the air, such as, for example the laccases, or to produce minor quantities of hydrogen peroxide in situ and in this manner biocatalytically activate the oxidation of the dyestuff precursors. Particularly suitable catalysts for the oxidation of the dyestuff precursors are the so-called 2-electron oxidoreductases combined with the specific substrates for them, e.g.

pyranose-oxidase and e.g. D-glucose or galactose,
glucose-oxidase and D-glucose,
glycerol-oxidase and glycerol,
pyruvate-oxidase and pyruvic acid or its salts,
alcohol-oxidase and alcohols (MeOH, EtOH),
lactate oxidase and lactic acid and its salts,
tyrosinase-oxidase and tyrosine,
uricase and uric acid or its salts choline-oxidase and choline, amino acid-oxidase and amino acids.

The inventive colorants produce intensive colorations already at physiologically acceptable temperatures below 45° C. They are thus particularly suitable for dyeing human hair. For use on human hair, the colorants are usually mixed into an aqueous cosmetic carrier. Suitable aqueous cosmetic carriers are, for example, creams, emulsions, gels or other foaming solutions that contain surfactants, such as, for example shampoos or other preparations suitable for application on keratin-containing fibers. When required, it is also possible to mix the colorant into an anhydrous carrier.

The colorants according to the invention may also contain any of the known active substances, additives and auxiliaries typical of such preparations. In many cases, the colorants contain at least one surfactant, both anionic and zwitterionic, ampholytic, nonionic and cationic surfactants being suitable in principle. In many cases, however, it has been found to be advantageous to select the surfactants from anionic, zwitterionic or nonionic surfactants.

Suitable anionic surfactants for the preparations according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ester, ether, amide and hydroxyl groups may also be present in the molecule. The following are examples of suitable anionic surfactants, each in the form of the sodium, potassium and ammonium salts as well as mono-, di- and trialkanolammonium salts containing 2 or 3 carbon atoms in the alkanol group, linear fatty acids containing 10 to 22 carbon atoms (soaps), ether carboxylic acids with the formula R—O—($CH_2$—$CH_2O$)$_x$—$CH_2$—COOH, in which R is a linear alkyl group containing 10 to 22 carbon atoms and x=0 or 1 to 16, acyl sarcosides containing 10 to 18 carbon atoms in the acyl group, acyl taurides containing 10 to 18 carbon atoms in the acyl group, acyl isethionates containing 10 to 18 carbon atoms in the acyl group, mono- and dialkyl sulfosuccinates containing 8 to 18 carbon atoms in the alkyl group and monoalkyl polyoxyethyl sulfosuccinates containing 8 to 18 carbon atoms in the alkyl group and 1 to 6 oxyethyl groups, linear alkanesulfonates containing 12 to 18 carbon atoms, linear alpha-olefinesulfonates containing 12 to 18 carbon atoms, methyl esters of alpha-sulfofatty acids from fatty acids containing 12 to 18 carbon atoms, alkyl sulfates and alkyl polyglycol ether sulfates corresponding to the formula R—O($CH_2$—$CH_2O$)$_x$—$OSO_3H$, in which R is a preferably linear alkyl group containing 10 to 18 carbon atoms and x=0 or 1 to 12, mixtures of surface-active hydroxysulfonates according to DE-A-37 25 030, sulfated hydroxyalkylpolyethylene- and/or hydroxyalkylenepropylene glycol ethers according to DE-A-37 23 354, sulfonates of unsaturated fatty acids containing 12 to 24 carbon atoms and 1 to 6 double bonds according to DE-A-39 26 344, esters of tartaric acid and citric acid with alcohols in the form of addition products of around 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule as well as particularly salts of saturated and particularly unsaturated $C_8$–$C_{22}$ carboxylic acids such as oleic acid stearic acid, isostearic acid and palmitic acid.

Zwitterionic surfactants are defined as surface-active compounds, which contain at least one quaternary ammonium group and at least one —$COO^{(-)}$ or —$SO_3^{(-)}$ group in the molecule. Particularly suitable zwitterionic surfactants are the so-called betaines, such as N-alkyl-N,N-dimethylammonium glycinates, for example cocoalkyldimethylammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. A preferred zwitterionic surfactant is the fatty acid amide derivative known by the CTFA name of Cocamidopropyl Betaine.

Ampholytic surfactants are understood to be such surface-active compounds which, in addition to a $C_8$–$C_{18}$ alkyl or acyl group, contain at least one free amino group and at least one —COOH or —$SO_3H$ group in the molecule and which are capable of forming internal salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids each containing around 8 to 18 carbon atoms in the alkyl group. Particularly preferred ampholytic surfactants are N-cocoalkyl aminopropionate, cocoacyl aminoethyl aminopropionate and $C_{12}$–$C_{18}$ acylsarcosine.

Nonionic surfactants contain as the hydrophilic group for example a polyol group, a polyalkylene glycol ether group or a combination of polyol and polyglycol ether groups. Examples of such compounds are products of the addition of 2 to 30 mol ethylene oxide and/or 0 to 5 mol propylene oxide onto linear and branched fatty alcohols containing 8 to 22 carbon atoms, onto fatty acids containing 12 to 22 carbon atoms and onto alkylphenols containing 8 to 15 carbon atoms in the alkyl group, $C_{12}$–$C_{22}$ fatty acid monoesters and diesters of products of the addition of 1 to 30 mol ethylene oxide onto glycerol, $C_8$–$C_{22}$ alkylmono- and oligoglycosides and their ethoxylated analogs, products of the addition of 5 to 60 mol ethylene oxide onto castor oil and hydrogenated castor oil, products of the addition of ethylene oxide onto sorbitan fatty acid esters, products of the addition of ethylene oxide onto fatty acid alkanolamides.

Examples of cationic surfactants suitable for the inventive hair treatment agents are particularly quaternary ammonium compounds. Ammonium halides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other suitable cationic surfactants according to the invention are represented by quaternized protein hydrolyzates.

According to the invention, also suitable are cationic silicone oils such as, for example the commercially available products Q2-7224 (manufacturer: Dow Corning; a stabilized trimethylsilylamodimethicone), Dow Corning® 929 Emulsion (comprising a hydroxylamino-modified silicone, which is also referred to as amodimethicone), SM-2059 (manufacturer: General Electric), SLM-55067 (manufacturer: Wacker) and Abil®-Quat 3270 and 3272 (manufacturer: Th. Goldschmidt; diquaternary polydimethylsiloxanes, Quaternium-80).

Alkylamidoamines, particularly fatty acid amidoamines such as stearylamido propyl dimethyl amine, available under the name Tego Amid®S 18, are characterized by a good conditioning action, especially by their good biodegradability.

Quaternary ester compounds, known as "esterquats" likewise have good biodegradability such as methylhydroxyalkyldialkoyloxyalkylammonium methosulfate commercialized under the trade name Stepantex®.

An example of a suitable cationic surfactant quaternary sugar derivative is the commercial product Glucquat®100, a "lauryl methyl gluceth-10 hydroxypropyl dimonium chloride" according to CTFA nomenclature.

The compounds used as surfactants with alkyl groups may each be homogeneous compounds. In general, however, these compounds are preferably produced from natural vegetal or animal raw materials and result in mixtures of products with raw material-dependent, different alkyl chain lengths.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained from the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be preferred.

Further active products, adjuvants and additives are for example
- nonionic polymers such as, for example, vinyl pyrrolidone/vinyl acrylate copolymers, polyvinyl pyrrolidone and vinyl pyrrolidone/vinyl acetate copolymers and polysiloxanes,
- cationic polymers such as quaternized cellulose ethers, polysiloxanes with quaternized groups, dimethyldiallylammonium chloride polymers, acrylamide-dimethyldiallylammonium chloride copolymers, dimethylaminoethylmethacrylate-vinyl pyrrolidone copolymers quaternized with diethyl sulfate, vinyl pyrrolidone-imidazolinium methochloride copolymers and quaternized polyvinyl alcohol,
- zwitterionic and amphoteric polymers such as, for example, acrylamidopropyltrimethylammonium chloride/acrylate copolymers and octyl acrylamide/methyl methacrylate/tert.-butylaminoethyl methacrylate/2-hydroxypropyl methacrylate copolymers,
- anionic polymers such as, for example polyacrylic acid, crosslinked polyacrylic acid, vinyl acetate/crotonic acid copolymers, vinyl pyrrolidone/vinyl acetate copolymers, vinyl acetate/butyl maleate/isobornyl acrylate copolymers, methyl vinyl ether/maleic anhydride copolymers and acrylic acid/ethyl acrylate/N-tert.butylacrylamide terpolymers,
- thickeners, such as agar agar, guar gum, alginates, xanthane gum, gum arabic, karaya gum, locust bean flour, linseed gums, dextrans, cellulose derivatives, for example methyl cellulose, hydroxyalkyl cellulose and carboxymethyl cellulose, starch fractions and derivatives, such as amylose, amylopectin and dextrins, clays such as, for example, bentonite or fully synthetic hydrocolloids such as, for example, polyvinyl alcohol,
- structurants such as glucose and maleic acid,
- hair-conditioning compounds, such as phospholipids, for example soya lecithin, egg lecithin and kephalins, as well as silicone oils,
- protein hydrolyzates, particularly hydrolyzates of elastin, collagen, keratin, milk protein, soya protein and wheat protein, their condensation products with fatty acids as well as quaternized protein hydrolyzates,
- perfume oils, dimethyl isosorbide and cyclodextrins,
- solubilizers such as ethanol, isopropanol, ethylene glycol, propylene glycol, glycerine and diethylene glycol,
- anti-dandruff agents, such as piroctone oleamine and zinc omadine,
- additional substances to adjust the pH,
- active substances such as panthenol, pantothenic acid, allantoin, pyrrolidone carboxylic acids and their salts, plant extracts and vitamins,
- cholesterol,
- light stabilizers
- consistency factors, such as sugar esters, polyol esters or polyol alkyl ethers,
- fats and waxes, such as spermaceti, beeswax, montan wax and paraffins,
- fatty acid alkanolamides,
- complexing agents, such as EDTA, NTA and phosphonic acids,
- swelling and penetration agents, such as glycerine, propylene glycol monomethyl ether, carbonates, bicarbonates, guanidines, ureas and primary, secondary and tertiary phosphates, imidazoles, tannins, pyrrole,
- opacifiers, such as latex,
- pearlizers, such as ethylene glycol mono- and distearate,
- propellants, such as propane/butane mixtures, $N_2O$, dimethyl ether, $CO_2$ and air and
- antioxidants.

For the manufacture of the inventive colorant, the constituents of the aqueous carrier are added in typical quantities for this application; e.g. emulsifiers are added in concentrations from 0.5 to 30 wt. % and thickeners in concentrations from 0.1 to 25 wt. % of the total colorant.

For the color result it can be advantageous to add ammonium or metal salts to the colorant. Suitable metal salts are e.g. formates, carbonates, halides, sulfates, butyrates, valeriates, capronates, acetates, lactates, glycolates, tartrates, citrates, gluconates, propionates, phosphates and phosphonates of alkali metals, such as potassium, sodium or lithium, earth alkali metals such as magnesium, calcium, strontium or barium, or aluminum, manganese, iron, cobalt, copper or zinc, wherein sodium acetate, lithium bromide, calcium bromide, calcium gluconate, zinc chloride, zinc sulfate, magnesium chloride, magnesium sulfate, ammonium carbonate, -chloride and -acetate are preferred. These salts are preferably comprised in a quantity of 0.03 to 65 mmol, particularly 1 to 40 mmol based on 100 g of the total colorant.

The pH of the ready-to-use dye preparations lies typically between 2 and 11, preferably between 5 and 10.

A second subject of the invention is colorants for keratin-containing fibers, particularly human hair, comprising the reaction products RP according to Formula VIII as coloring components,

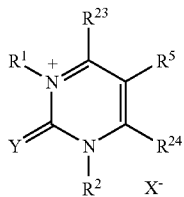

(VIII)

in which
R$^1$, R$^2$, R$^5$, Y and X$^-$ are as defined as under Formula I,
R$^{23}$ and R$^{24}$ independently of one another stand for a hydrogen atom, a C$_1$–C$_6$ alkyl group, a group according to Formula IX,

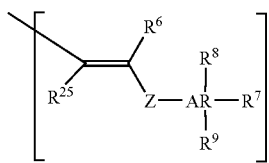

(IX)

in which
R$^6$, R$^7$, R$^8$, R$^9$, AR and Z are defined as described under Formula II,
R$^{25}$ stands for a hydrogen atom or a C$_1$–C$_5$ alkyl group, with the proviso that at least one of the radicals R$^{23}$ and R$^{24}$ stands for a group according to Formula IX.

It is particularly preferred if the inventive agent comprises such reaction products RP according to Formula VIII in which AR according to Formula IX stands for benzene or naphthalene.

Further, it is particularly preferred if the inventive agent comprises such reaction products according to Formula VIII in which Z according to Formula IX stands for a direct bond or vinylene.

It is particularly preferred if the inventive agent comprises such reaction products RP according to Formula VIII in which R$^{25}$ according to Formula IX stands for a hydrogen atom.

It is particularly preferred if the inventive agent comprises such reaction products RP according to Formula VIII in which R$^6$ according to Formula IX stands for a hydrogen atom.

It is particularly preferred if the inventive agents comprise such reaction products RP according to Formula VIII in which R$^7$, R$^8$ and R$^9$ according to Formula IX, independently of one another stand for a hydrogen atom, a halogen atom, a C$_1$–C$_6$ alkyl group, a hydroxyl group, a C$_1$–C$_6$ alkoxy group, an amino group, a C$_1$–C$_6$ dialkylamino group, a di(C$_2$–C$_6$ hydroxyalkyl)amino group, a di(C$_1$–C$_6$ alkoxy-C$_1$–C$_6$-alkyl)amino group, a C$_1$–C$_6$ hydroxyalkyloxy group, a sulfonyl group, a carboxyl group, a sulfonamide group, a carbamoyl group, a C$_2$–C$_6$ acyl group, an acetyl group, a sulfonic acid group, a sulfonamide group or a nitro group.

It is particularly preferred if the inventive agents comprise such reaction products RP according to Formula VIII in which R$^7$, R$^8$ and R$^9$ according to Formula IX, independently of one another stand for a hydrogen atom, a halogen atom, a C$_1$–C$_6$ alkyl group, a hydroxyl group, a C$_1$–C$_6$ alkoxy group, an amino group, a C$_1$–C$_6$ dialkylamino group, a di(C$_2$–C$_6$ hydroxyalkyl)amino group, a di(C$_1$–C$_6$ alkoxy-C$_1$–C$_6$-alkyl)amino group, a C$_1$–C$_6$ hydroxyalkyloxy group, a sulfonyl group, a carboxyl group, a sulfonamide group, a carbamoyl group, a C$_2$–C$_6$ acyl group, an acetyl group, a sulfonic acid group, a sulfonamide group or a nitro group, with the proviso that if AR stands for benzene and one of the radicals R$^7$, R$^8$ or R$^9$ para to group Z stands for a hydrogen atom, a halogen atom, a C$_1$–C$_6$ alkoxy group or an amino group then both the other radicals, independently of one another mean neither a hydrogen atom nor a halogen atom.

It is particularly preferred if the inventive agents comprise such reaction products RP according to Formula VIII in which R$^7$, R$^8$ and R$^9$ according to Formula IX, independently of one another stand for a hydrogen atom, a halogen atom, a C$_1$–C$_6$ alkyl group, a hydroxyl group, a C$_1$–C$_6$ alkoxy group, an amino group, a C$_1$–C$_6$ dialkylamino group, a di(C$_2$–C$_6$ hydroxyalkyl)amino group, a di(C$_1$–C$_6$ alkoxy-C$_1$–C$_6$-alkyl)amino group, a C$_1$–C$_6$ hydroxyalkyloxy group, a sulfonyl group, a carboxyl group, a sulfonamide group, a carbamoyl group, a C$_2$–C$_6$ acyl group, an acetyl group, a sulfonic acid group, a sulfonamide group or a nitro group, with the proviso that at least one of the radicals R$^7$, R$^8$ or R$^9$ para to group Z stands for a group that is selected from a hydroxyl group, a C$_1$–C$_6$ dialkylamino group, a di(C$_2$–C$_6$ hydroxyalkyl)amino group, a di(C$_1$–C$_6$ alkoxy-C$_1$–C$_6$-alkyl) amino group and a C$_1$–C$_6$ hydroxyalkyloxy group.

The particularly preferred compounds according to Formula VIII are the compounds cited in the first subject matter of the invention.

The reaction product RP is preferably comprised in the agents in an amount from 0.03 to 65 mmol, particularly from 1 to 40 mmol, based on 100 g of the total colorant.

These colorants can additionally comprise
a) at least one further afore mentioned substantive dyestuff and/or
b) at least one afore mentioned oxidation dystuff precursor and/or at least one afore mentioned derivative of indoline or indole and
c) optional oxidizing agent such as e.g. hydrogen peroxide.

Moreover, all surfactants, color boosters, metal salts or oxidizing agents as well as additional adjuvants, active substances and additives that were already mentioned above, can be comprised in the inventive agent of the second subject matter of the invention.

A third subject-matter of the present invention relates to the use of at least one 1,2-dihydropyrimidinium derivative according to Formula 1 and/or its enamine form,

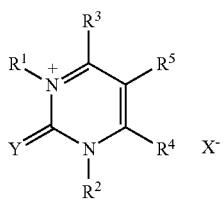

wherein $R^1$, $R^2$, $R^3$, $R^4$, $R^5$, Y and $X^-$ are as defined above, in combination with at least one reactive carbonyl compound (component B) as the coloring component in hair colorants.

In a preferred embodiment, the 1,2-dihydropyrimidinium derivatives according to Formula I are used in combination with at least one reactive carbonyl compound of the component B selected from the previous cited preferred and particularly preferred representatives, as the coloring component in hair colorants.

Moreover, it can be preferred to use at least one reaction product RP of a 1,2-dihydropyridinium derivative according to Formula I and a compound of component B as the coloring components in hair colorants.

A fourth subject-matter of the present invention relates to a process for dyeing keratin-containing fibers, particularly human hair, wherein a colorant comprising at least one 1,2-dihydropyrimidinium derivative according to Formula 1 and/or its enamine form,

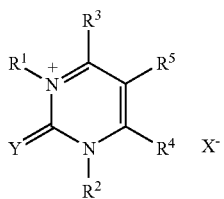

wherein $R^1$, $R^2$, $R^3$, $R^4$, $R^5$, Y and $X^-$ are as defined above, in combination with at least one compound with a reactive carbonyl group (component B), as well as customary cosmetic ingredients are applied to the keratin-containing fibers for some time, normally 15–30 minutes, left on the fibers and subsequently rinsed out or washed out with a shampoo. During the contact time of the agent on the fibers, it can be advantageous to support the dyeing procedure by providing heat. The heat can be supplied from an external heat source, such as e.g. warm air from a hairdryer or also, particularly with a hair coloration on living test persons, by means of the body temperature of the test persons. The latter option is usually by means of a hood covering over the parts to be dyed.

In doing so, the 1,2-dihydrpyrimidinium derivatives according to Formula I and the compounds of component B, particularly their representatives cited above as being preferred and particularly preferred, are applied to the hair as color-providing components either simultaneously or one after the other, i.e. in a multi-step process in which it is unimportant which of the components is applied first. The optionally contained ammonium or metal salts can be added here to the compounds of Formula I or to the compounds of component B. There can be an interval of up to 30 minutes between the application of the individual components. It is also possible to pretreat the fibers with the salt solution.

If desired, the keratin-containing fibers that are to be dyed can be pretreated before the application of the inventive agent in the inventive process. The chronology of the required pretreatment step and the application of the inventive agent must not be immediately one after the other, as there can be an interval of up to a maximum of two weeks between the pretreatment step and the application of the inventive agent. A plurality of pretreatment methods is suitable for this purpose. Preferably, the fiber is subjected to V1 bleaching prior to the application of the inventive agent or V2 an oxidative coloration prior to the application of the inventive agent.

In the context of the pretreatment V1, the keratin-containing fiber is treated with a bleach. In addition to an oxidizing agent, typically hydrogen peroxide, the bleach preferably contains at least one inorganic peroxy salt as active oxidizing booster and bleach booster, such as, e.g. a peroxydisulfate of sodium, potassium or ammonium. The pretreatment V1 provides a particular brilliance and color depth to the coloration according to the inventive process.

In the context of the pretreatment V2, the fiber is treated with a composition comprising the afore mentioned oxidation dyestuff precursors as developer and optional coupler components, together with optional afore mentioned derivatives of indole or indoline, and with an optional addition of suitable afore mentioned oxidizing agents to the hair, and left on the keratin fibers for a contact time of 5 to 45 minutes. The hair is then washed. By a final application of the inventive agent, a new shade of color can be imparted to the existent oxidation colorations. By choosing a color shade of the inventive agent in the same shade as the oxidative coloration, this enables, after the inventive process, the coloration of the existent oxidation coloration to be restored. It turns out that the color restoration or shading according to the inventive process is superior in color brilliance and color depth to a color restoration or shading made solely with customary substantive dyestuffs.

If in addition to the compounds according to Formula I and the optional component B, the hair colorant contains hydrogen peroxide or an oxidizing agent mixture that contains hydrogen peroxide, then the pH of the hydrogen peroxide-containing hair colorant preferably lies in a pH range of pH 7 to pH 11, particularly preferably pH 8 to pH 10. The oxidizing agent can be mixed with the hair colorant immediately prior to use and the mixture applied to the hair. When the compounds of Formula I and the component B are applied to the hair in a two-step process, the oxidizing agent is used together with the corresponding coloring components in one of the two process steps. For this purpose, it can be preferred to mix the oxidizing agent with one of the coloring components in a container.

The 1,2-dihydropyrimidinium derivatives according to Formula I and the compounds of component B can either be stored separately or together, either in a liquid to pasty preparation (aqueous or anhydrous) or as dry powder. If the components are stored together in a liquid preparation, then this should be substantially anhydrous in order to reduce any reaction of the components. For separate storage, the reactive components are to be well mixed together immediately prior to their use. For dry storage, normally a defined amount of warm water (30° C. to 80° C.) is added prior to usage and a homogeneous mixture is prepared.

A fifth subject of the invention is the use of at least one 1,2-dihydropyrimidinium derivative according to Formula 1, and/or its enamine form,

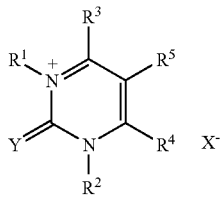

wherein $R^1$, $R^2$, $R^3$, $R^4$, $R^5$, Y and $X^-$ are as defined above, in combination with at least one reactive carbonyl compound (component B) for shading the oxidation colorations of keratin-containing fibers, particularly human hair. On usage it is immaterial if the shading occurs simultaneously to the oxidative coloration or if the oxidative coloration occurrs prior to the shading.

A sixth subject of the invention is the use of at least one 1,2-dihydropyrimidinium derivative according to Formula I1, and/or its enamine form,

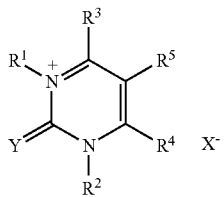

wherein, $R^1$, $R^2$; $R^3$, $R^4$, $R^5$, Y and $X^-$ are as defined above, in combination with at least one reactive carbonyl compound (component B) for restoring the color of keratin-containing fibers dyed with oxidative colorants.

The colorations of keratin-containing fibers are known to be affected by environmental influences, such as, for example, light, rubbing or washing and can thereby lose in brilliance and color depth. In the worst case, a shift in color of the shade may occur. When the user wishes, such aged colorations of keratin-containing fibers can be restored by a color refreshment to present a color close to that of the original coloration. According to the invention, a combination of at least one compound of Formula I and at least one reactive carbonyl compound is used for such a color restoration.

EXAMPLES

Preparation of a Colorant Solution.

Each slurry or solution was prepared at about 50° C. with 3 mmol of 1,2-dihydropyrimidinium derivative of Formula I (component A) with 0.41 g sodium acetate in 30 ml water. 3 mmol of the compound of component B are added to this mixture immediately prior to use. The mixture was adjusted either to pH 9 with a 10% aqueous sodium hydroxide solution or to pH 4 or 6 with hydrochloric acid (see Table 1).

Coloring Tests

A strand of 90% gray, un-pretreated human hair was placed in the freshly prepared colorant solution for 30 minutes at 30° C. The strand was then rinsed with luke-warm water for 30 seconds, dried with warm air (30° C. to 40° C.) and finally combed out.

Each color shade and color depth of the color-test examples are presented in the following Table 1.

Compounds of Component A (in Table 1);

A1  1,2-dihydro-1,3,4,6-tetramethyl-2-oxo-pyrimidinium chloride

A2  1,2-dihydro-1,3,4-trimethyl-2-oxo-pyrimidinium chloride

A3  1,2-dihydro-4,6-dimethyl-1,3-dipropyl-2-oxo-pyrimidinium chloride

A4  1,2-dihydro-1,3,4,6-tetramethyl-2-thioxo-pyrimidinium hydrogen sulfate

A5  1,2-dihydro-1,3,4,6-tetramethyl-2-oxo-pyrimidinium hydrogen sulfate

A6  1,2-dihydro-1,3,4,5,6-pentamethyl-2-oxo-pyrimidinium chloride

Compounds of Component B (in Table 1):

B1 2,4-dihydroxybenzaldehyde
B2 vanillin
B3 isatin
B4 3-indolealdehyde
B5 coniferyl aldehyde
B6 3,5-dimethoxy4-hydroxybenzaldehyde
B7 4-dimethylamino-1-naphthaldehyde
B8 4-hydroxybenzaldehyde
B9 4-hydroxy-1-naphthaldehyde
B10 4-diethylamino-2-hydroxybenzaldehyde
B11 4-dimethylaminobenzaldehyde
B12 4-hydroxy-2-methoxybenzaldehyde
B13 3,4-dihydroxybenzaldehyde
B14 4-dimethylaminocinnamaldehyde
B15 3,5-dimethyl4-hydroxybenzaldehyde
B16 2,3,4-trihydroxybenzaldehyde
B17 2,4,6-trihydroxybenzaldehyde
B18 3-hydroxy-4-methoxybenzaldehyde
B19 2-hydroxy4-methoxybenzaldehyde
B20 2,3-dimethoxybenzaldehyde
B21 2,4-dimethoxybenzaldehyde
B22 2,3,4-trimethoxybenzaldehyde
B23 2,4,5-trimethoxybenzaldehyde
B24 3-bromo-4-methoxybenzaldehyde
B25 3-methyl-4-methoxybenzaldehyde
B26 4-dimethylamino-2-methoxybenzaldehyde
B27 4-formyl-1-methylquinolinium p-toluenesulfonate
B28 pyrrole-2-carboxaldehyde
B29 1-methylpyrrole-2-carboxaldehyde
B30 2-furaldehyde
B31 4-diethylaminobenzaldehyde
B32 2,5-dihydroxybenzaldehyde
B33 3-hydroxy4-nitrobenzaldehyde
B34 2-hydroxy-3-methoxy-5-nitrobenzaldehyde
B35 5-bromo4-hydroxy-3-methoxybenzaldehyde
B36 4-methoxybenzaldehyde
B37 2-hydroxy-1-naphthaldehyde
B38 2-methoxy-1-naphthaldehyde
B39 4-methoxy-1-naphthaldehyde
B40 2-{[(4-methoxyphenyl)methylene]amino}ethanol
B41  4-{[(2-hydroxyethyl)imino]methyl}-2,6-dimethoxyphenol
B42 1-(diethoxymethyl)4-methoxybenzene
B43 4-(diethoxymethyl)-2,6-dimethoxyphenol

TABLE 1

| Component A | Component B | Color | pH |
|---|---|---|---|
| A1 | B1 | intense red violet | 9 |
| A1 | B2 | bright violet | 9 |
| A1 | B3 | intense orange | 9 |
| A1 | B4 | intense orange | 9 |
| A1 | B5 | dark gray | 9 |
| A1 | B6 | intense dark blue | 9 |
| A1 | B7 | pale gray | 9 |
| A1 | B8 | intense purple-red | 9 |
| A1 | B9 | gray black | 9 |
| A1 | B10 | light pink | 9 |
| A1 | B11 | intense red violet | 9 |
| A1 | B15 | bright violet | 9 |
| A1 | B16 | red brown | 9 |
| A1 | B17 | pale pink | 9 |
| A1 | B18 | brown | 9 |
| A1 | B19 | dark red | 9 |
| A1 | B20 | yellow brown | 9 |
| A1 | B21 | bright orange | 9 |
| A1 | B22 | orange brown | 9 |
| A1 | B23 | intense orange | 9 |
| A1 | B24 | yellow | 9 |
| A1 | B25 | brown orange | 9 |
| A1 | B26 | intense violet | 9 |
| A1 | B27 | brown | 9 |
| A1 | B28 | red brown | 9 |
| A1 | B29 | orange | 9 |
| A1 | B30 | beige brown | 9 |
| A2 | B1 | red | 9 |
| A2 | B2 | bright violet | 9 |
| A2 | B3 | orange | 9 |
| A2 | B4 | orange | 9 |
| A2 | B6 | turquoise blue | 9 |
| A2 | B8 | pink | 9 |
| A2 | B9 | black | 9 |
| A2 | B12 | bright pinky red | 9 |
| A2 | B13 | intense dark blue | 9 |
| A2 | B14 | yellow brown | 9 |
| A2 | B15 | violet | 9 |
| A3 | B1 | intensive dark red | 9 |
| A3 | B2 | intense violet | 9 |
| A4 | B1 | pinky red | 9 |
| A4 | B2 | medium blue | 9 |
| A4 | B6 | dark | 9 |
| A4 | B9 | blue black | 6 |
| A4 | B10 | intense dark red | 6 |
| A4 | B11 | black | 6 |
| A4 | B15 | bright violet | 6 |
| A4 | B23 | bright red | 6 |
| A4 | B25 | intense red | 6 |
| A4 | B27 | brown | 6 |
| A4 | B31 | dark blue | 6 |
| A4 | B40 | yellow orange | 9 |
| A4 | B41 | dark blue | 9 |
| A4 | B42 | yellow orange | 4 |
| A4 | B43 | dark blue | 6 |
| A5 | B9 | dark blue | 6 |
| A5 | B32 | green brown | 9 |
| A5 | B33 | brown orange | 9 |
| A5 | B34 | black | 9 |
| A5 | B35 | bright violet | 9 |
| A5 | B36 | bright orange | 9 |
| A5 | B37 | dark blue | 9 |
| A5 | B38 | gray pink | 9 |
| A6 | B1 | pinky red | 9 |
| A6 | B2 | intense violet | 9 |
| A6 | B6 | intense turquoise | 9 |
| A6 | B8 | pinky red | 9 |
| A6 | B9 | green | 9 |
| A6 | B12 | pinky red | 9 |
| A6 | B13 | intense gray blue | 9 |
| A6 | B15 | violet | 9 |

What is claimed is:

1. A composition for dyeing keratin-containing fibers comprising at least one 1,2-dihydropyrimidinium derivative (component A) according to Formula I and/or its enamine form

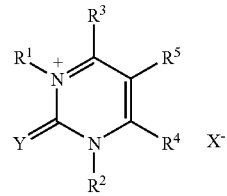

(I)

wherein $R^1$ and $R^2$ independently of one another are a linear or cyclic $C_1$–$C_6$ alkyl group, a $C_2$–$C_6$ alkenyl group, an optionally substituted aryl group, an optionally substituted heteroaryl group, an aryl $C_1$–$C_6$ alkyl group, a $C_1$–$C_6$ hydroxyalkyl group, a $C_2$–$C_6$ polyhydroxyalkyl group, a $C_1$–$C_6$ alkoxy-$C_1$–$C_6$ alkyl group, a group $R^I R^{II} N$—$(CH_2)_m$— in which $R^I$ and $R^{II}$ independently of one another stand for a hydrogen atom, a $C_1$–$C_4$ alkyl group, a $C_1$–$C_4$ hydroxyalkyl group or an aryl $C_1$–$C_6$ alkyl group, wherein $R^I$ and $R^{II}$ together with the nitrogen atom can form a 5-, 6-, or 7-membered ring, and m stands for a number 2, 3, 4, 5 or 6.

$R^3$ and $R^4$ independently of one another are a hydrogen atom or an alkyl group, wherein at least one of the radicals $R^3$ and $R^4$ means a $C_1$–$C_6$ alkyl group, $R^5$ is a hydrogen atom, a $C_1$–$C_6$ alkyl group, a $C_1$–$C_6$ hydroxyalkyl group, a $C_2$–$C_6$ polyhydroxyalkyl group, a $C_1$–$C_6$ alkoxy group, a $C_1$–$C_6$ hydroxyalkoxy group, a group $R^{III} R^{IV} N$—$(CH_2)_q$—, in which $R^{III}$ and $R^{IV}$ stand independently of one another for a hydrogen atom, a $C_1$–$C_6$ alkyl group, a $C_1$–$C_6$ hydroxyalkyl group or an aryl $C_1$–$C_6$ alkyl group, and q stands for a number 1, 2, 3, 4, 5 or 6, wherein the radical $R^5$ together with one of the radicals $R^3$ or $R^4$ can form a 5- or 6-membered aromatic or aliphatic ring that can be optionally substituted with a halogen atom, a $C_1$–$C_6$ alkyl group, a $C_1$–$C_6$ hydroxyalkyl group, a $C_2$–$C_6$ polyhydroxyalkyl group, a $C_1$–$C_6$ alkoxy group, a $C_1$–$C_6$ hydroxyalkoxy group, a nitro group, a hydroxyl group, a group $R^V R^{VI} N$—$(CH_2)_s$—, in which $R^V$ and $R^{VI}$ independently of one another stand for a hydrogen atom, a $C_1$–$C_6$ alkyl group, a $C_1$–$C_6$ hydroxyalkyl group or an aryl $C_1$–$C_6$ alkyl group, and s stands for a number 0, 1, 2, 3, 4, 5 or 6, Y is an oxygen atom, a sulfur atom or a group $NR^{VII}$, in which $R^{VII}$ stands for a hydrogen atom, an aryl group, a heteroaryl group, a $C_1$–$C_6$ alkyl group or a $C_1$–$C_6$ arylalkyl group, $X^-$ is a halide, benzenesulfonate, p-toluenesulfonate, $C_1$–$C_4$ alkanesulfonate, trifluoromethanesulfonate, perchlorate, 0.5 $SO_4^{-2}$, hydrogen sulfate, tetrafluoroborate, hexafluorophosphate or tetrachlorozincate, and at least one compound with a reactive carbonyl group (component B).

2. The composition of claim 1 wherein Y is an oxygen atom or a sulfur atom.

3. The composition of claim 2 wherein Y is an oxygen atom.

4. The composition of claim 1 wherein at least one of $R^3$ or $R^4$ is a methyl group.

5. The composition of claim 1 wherein $X^-$ is chloride, bromide, iodide, hydrogen sulfate or p-toluenesulfonate.

6. The composition of claim 1 wherein the compound according to Formula I is selected from the group consisting of 1,2-dihydro-1,3,4,6-tetramethyl-2-oxo-pyrimidinium chloride, 1,2-dihydro-1,3-diethyl-4,6-dimethyl-2-oxo-pyrimidinium chloride, 1,2-dihydro-1,3-dipropyl-4,6-dimethyl-2-oxo-pyrimidinium chloride, 1,2-dihydro-1,3-di (2-hydroxyethyl)-4,6-dimethyl-2-oxo-pyrimidinium chloride, 1,2-dihydro-1,3-diphenyl-4,6-dimethyl-2-oxo-pyrimidinium chloride, 1,2-dihydro-1,3,4,6-tetramethyl-2-oxo-pyrimidinium hydrogen sulfate, 1,2-dihydro-1,3-diethyl-4,6-dimethyl-2-oxo-pyrimidinium hydrogen sulfate, 1,2-dihydro-1,3-dipropyl-4,6-dimethyl-2-oxo-pyrimidinium hydrogen sulfate, 1,2-dihydro-1,3-di(2-hydroxyethyl)-4,6-dimethyl-2-oxo-pyrimidinium hydrogen sulfate, 1,2-dihydro-1,3-diphenyl-4,6-dimethyl-2-oxo-pyrimidinium hydrogen sulfate, 1,2-dihydro-1,3,4-trimethyl-2-oxo-pyrimidinium chloride, 1,2-dihydro-1,3,4-trimethyl-2-oxo-pyrimidinium hydrogen sulfate, 1,2-dihydro-1,3-diethyl-4-methyl-2-oxo-pyrimidinium chloride, 1,2-dihydro-1,3-diethyl-4-methyl-2-oxo-pyrimidinium hydrogen sulfate, 1,2-dihydro-1,3-dipropyl-4-methyl-2-oxo-pyrimidinium chloride, 1,2-dihydro-1,3-dipropyl-4-methyl-2-oxo-pyrimidinium hydrogen sulfate, 1,2-dihydro-1,3-di (2-hydroxyethyl)-4-methyl-2-oxo-pyrimidinium chloride, 1,2-dihydro-1,3-di (2-hydroxyethyl)-4-methyl-2-oxo-pyrimidinium hydrogen sulfate, 1,2-dihydro-1,3-diphenyl-4-methyl-2-oxo-pyrimidinium chloride, 1,2-dihydro-1,3-diphenyl-4-methyl-2-oxo-pyrimidinium hydrogen sulfate, 1,2-dihydro-1,3,4,5,6-pentamethyl-2-oxo-pyrimidinium chloride, 1,2-dihydro-1,3,4,6-tetramethyl-2-thioxo-pyrimidinium chloride, 1,2-dihydro-1,3-diethyl-4,6-dimethyl-2-thioxo-pyrimidinium chloride, 1,2-dihydro-1,3-dipropyl-4,6-dimethyl-2-thioxo-pyrimidinium chloride, 1,2-dihydro-1,3-di (2-hydroxyethyl)-4,6-dimethyl-2-thioxo-pyrimidinium chloride, 1,2-dihydro-1,3-diphenyl-4,6-dimethyl-2-thioxo-pyrimidinium chloride, 1,2-dihydro-1,3,4,6-tetramethyl-2-thioxo-pyrimidinium hydrogen sulfate, 1,2-dihydro-1,3-dipropyl-4,6-dimethyl-2-thioxo-pyrimidinium hydrogen sulfate, 1,2-dihydro-1,3-di(2-hydroxyethyl)-4,6-dimethyl-2-thioxo-pyrimidinium hydrogen sulfate, 1,2-dihydro-1,3-diphenyl-4,6-dimethyl-2-thioxo-pyrimidinium hydrogen sulfate, 1,2-dihydro-1,3,4-trimethyl-2-thioxo-pyrimidinium chloride, 1,2-dihydro-1,3,4-trimethyl-2-thioxo-pyrimidinium hydrogen sulfate, 1,2-dihydro-1,3-diethyl-4-methyl-2-thioxo-pyrimidinium chloride, 1,2-dihydro-1,3-diethyl-4-methyl-2-thioxo-pyrimidinium hydrogen sulfate, 1,2-dihydro-1,3-dipropyl-4-methyl-2-thioxo-pyrimidiniumchloride, 1,2-dihydro-1,3-dipropyl-4-methyl-2-thioxo-pyrimidinium hydrogen sulfate, 1,2-dihydro-1,3-di (2-hydroxyethyl)-4-methyl-2-thioxo-pyrimidinium chloride, 1,2-dihydro-1,3-di(2-hydroxyethyl)-4-methyl-2-thioxo-pyrimidinium hydrogen sulfate, 1,2-dihydro-1,3-diphenyl-4-methyl-2-thioxo-pyrimidinium chloride, 1,2-dihydro-1,3-diphenyl-4-methyl-2-thioxo-pyrimidinium hydrogen sulfate, 1,2-dihydro-3,4-dimethyl-2-oxo-quinazolinium chloride, 1,2-dihydro-3,4-dimethyl-2-oxo-quinazolinium p-toluenesulfonate, 1,2-dihydro-3,4-dimethyl-2-thioxo-quinazolinium chloride, 1,2-dihydro-3,4-dimethyl-2-thioxo-quinazolinium p-toluenesulfonate, 1,2-dihydro-1,3,4-trimethyl-2-thioxo-quinazolinium hydrogen sulfate, 1,3,4-trimethyl-2-oxo-2,3,5,6,7,8-hexahydroquinolinium hydrogen sulfate, 1,3,4-trimethyl-2-thioxo-2,3,5,6,7,8-hexahydroquinolinium hydrogen sulfate, 1,3,4-trimethyl-2-oxo-3,5,6,7-tetrahydro-2H-cyclopenta[a]pyrimidinium hydrogen sulfate and 1,3,4-trimethyl-2-thioxo-3,5,6,7-tetrahydro-2H-cyclopenta[a]pyrimidinium hydrogen sulfate.

7. The composition of claim 1 wherein component B is selected from compounds according to Formula II

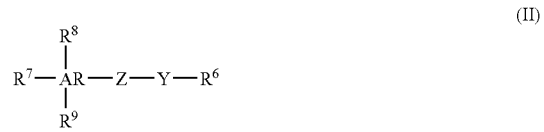

wherein
AR represents benzene, naphthalene, pyridine, pyrimidine, pyrazine, pyridazine, carbazole, pyrrole, pyrazole, furan, thiophene, 1,2,3-triazine, 1,3,5-triazine, quinoline, isoquinoline, indole, indoline, indolizine, indane, imidazole, 1,2,4-triazole, 1,2,3-triazole, tetrazole, benzimidazole, 1,3-thiazole, benzothiazole, indazole, benzoxazole, quinoxaline, quinazoline, quinolizine, quinnoline, acridine, iulolidine, acenaphthene, fluorene, biphenyl, diphenylmethane, benzophenone, diphenylether, azobenzene, chromone, cumarine, diphenylamine, stilbene, wherein the N-heteroaromatics can also be quaternized, $R^6$ is a hydrogen atom, a $C_1$–$C_6$ alkyl, $C_2$–$C_6$ acyl, $C_2$–$C_4$ alkenyl, $C_1$–$C_4$ perfluoroalkyl, an optionally substituted aryl or heteroaryl group, $R^7$, $R^8$ and $R^9$ independently from one another are a hydrogen atom, a halogen atom, a $C_1$–$C_6$ alkyl, $C_1$–$C_6$ alkoxy, $C_1$–$C_6$ aminoalkyl, $C_1$–$C_6$ hydroxyalkyl group, a $C_1$–$C_6$ alkoxy-$C_1$–$C_6$ alkyloxy group, a $C_2$–$C_6$ acyl group, an acetyl, a carboxyl, carboxylato, carbamoyl, sulfo, sulfato, sulfonamide, sulfonamido, $C_2$–$C_6$ alkenyl, an aryl, an aryl $C_1$–$C_6$ alkyl group, a hydroxyl, a nitro, a pyrrolidino, a morpholino, a piperidino, an amino or ammonio or a 1-imidazol(in)io group, wherein the last three groups can be substituted with one or more $C_1$–$C_6$ alkyl-, $C_1$–$C_6$ carboxyalkyl-$C_1$–$C_6$ hydroxyalkyl, $C_2$–$C_6$ alkenyl, $C_1$–$C_6$ alkoxy-$C_1$–$C_6$ alkyl, with optionally substituted benzylgroups, with sulfo-($C_1$ –$C_4$)-alkyl or heterocycle-($C_1$–$C_4$) alkyl groups, wherein two of the radicals $R^7$, $R^8$, $R^9$ and —Z—Y—$R^6$, together with the remainder of the molecule can form a condensed, optionally substituted 5-, 6- or 7-membered ring that can equally have a condensed aromatic ring, wherein AR, depending on the ring size, can have further substituents that independently of one another consist of the same groups as $R^7$, $R^8$ and $R^9$, Z is a direct bond, a carbonyl, a carboxy-($C_1$–$C_4$) alkylene, an optionally substituted $C_2$–$C_6$ alkenylene, $C_4$–$C_6$ alkadienylene, furylene, thienylene, arylene, vinylenearylene, vinylenefurylene, vinylenethienylene group, wherein Z, together with the —Y—$R^6$ group can also form an optionally substituted 5-, 6- or 7-membered ring.

Y is carbonyl.

8. The composition of claim 7 wherein component B is selected from the group consisting of acetophenone, propiophenone, 2-hydroxyacetophenone, 3-hydroxyacetophenone, 4-hydroxyacetophenone, 2-hydroxypropiophenone, 3-hydroxypropiophenone, 4-hydroxypropiophenone, 2-hydroxybutyrophenone, 3-hydroxybutyrophenone, 4-hydroxybutyrophenone, 2,4-dihydroxyacetophenone, 2,5-dihydroxyacetophenone, 2,6-dihydroxyacetophenone, 2,3,4-trihydroxyacetophenone, 3,4,5-trihydroxyacetophenone, 2,4,6-trihydroxyacetophenone, 2,4,6-trimethoxyacetophenone, 3,4,5-trimethoxyacetophenone, 3,4,5-trimethoxy-acetophenone-diethylketal, 4-hydroxy-3-methoxy-acetophenone, 3,5-dimethoxy-4-hydroxyacetophenone, 4-aminoacetophenone, 4-dimethylaminoacetophenone, 4-morpholinoacetophenone, 4-piperidinoacetophenone, 4-imidazolinoacetophenone, 2-hydroxy-5-bromo-acetophenone, 4-hydroxy-3-nitroacetophenone, acetophenone-2-carboxylic acid, acetophenone-4-carboxylic acid, benzophenone, 4-hydroxybenzophenone, 2-aminobenzophenone, 4,4'-dihydroxybenzophenone, 2,4-dihydroxy-benzophenone, 2,4,4'-trihydroxybenzophenone, 2,3,4-trihydroxybenzophenone, 2-hydroxy-1-acetonaphthone, 1-hydroxy-2-acetonaphthone, chromone, chromone-2-carboxylic acid, flavone, 3-hydroxyflavone, 3,5,7-trihydroxyflavone, 4',5,7-trihydroxyflavone, 5,6,7-trihydroxyflavone, quercetin, 1-indanone, 9-fluorenone, 3-hydroxyfluorenone, anthrone, 1,8-dihydroxyanthrone, vanillin, coniferyl aldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 4-hydroxy-2,3-dimethoxybenzaldehyde, 4-hydroxy-2,5-dimethoxy-benzaldehyde, 4-hydroxy-2,6-dimethoxybenzaldehyde, 4-hydroxy-2-methylbenzaldehyde, 4-hydroxy-3-methyl-benzaldehyde, 4-hydroxy-2,3-dimethylbenzaldehyde, 4-hydroxy-2,5-dimethyl-benzaldehyde, 4-hydroxy-2,6-dimethylbenzaldehyde, 4-hydroxy-3,5-dimethoxy-benzaldehyde, 4-hydroxy-3,5-dimethylbenzaldehyde, 3,5-diethoxy-4-hydroxy-benzaldehyde, 2,6-diethoxy-4-hydroxybenzaldehyde, 3-hydroxy-4-methoxy-benzaldehyde, 2-hydroxy-4-methoxybenzaldehyde, 2-ethoxy-4-hydroxy-benzaldehyde, 3-ethoxy-4-hydroxy-benzaldehyde, 4-ethoxy-2-hydroxybenzaldehyde, 4-ethoxy-3-hydroxy-benzaldehyde, 2,3-dimethoxybenzaldehyde, 2,4-dimethoxybenzaldehyde, 2,5-dimethoxybenzaldehyde, 2,6-dimethoxybenzaldehyde, 3,4-dimethoxybenzaldehyde, 3,5-dimethoxybenzaldehyde, 2,3,4-trimethoxybenzaldehyde, 2,3,5-trimethoxybenzaldehyde, 2,3,6-trimethoxybenzaldehyde, 2,4,6-trimethoxybenzaldehyde, 2,4,5-trimethoxybenzaldehyde, 2,5,6-trimethoxybenzaldehyde, 2-hydroxybenzaldehyde, 3-hydroxybenzaldehyde, 4-hydroxybenzaldehyde, 2,3-dihydroxybenzaldehyde, 2,4-dihydroxybenzaldehyde, 2,5-dihydroxybenzaldehyde, 2,6-dihydroxybenzaldehyde, 3,4-dihydroxybenzaldehyde, 3,5-dihydroxybenzaldehyde, 2,3,4-trihydroxybenzaldehyde, 2,3,5-trihydroxybenzaldehyde, 2,3,6-trihydroxybenzaldehyde, 2,4,6-trihydroxybenzaldehyde, 2,4,5-trihydroxybenzaldehyde, 2,5,6-trihydroxybenzaldehyde, 4-hydroxy-2-methoxybenzaldehyde, 4-dimethylaminobenzaldehyde, 4-diethylaminobenzaldehyde, 4-dimethylamino-2-hydroxybenzaldehyde, 4-diethylamino-2-hydroxybenzaldehyde, 4-pyrrolidinobenzaldehyde, 4-morpholinobenzaldehyde, 2-morpholinobenzaldehyde, 4-piperidinobenzaldehyde, 2-methoxy-1-naphthaldehyde, 4-methoxy-1-naphthaldehyde, 2-hydroxy-1-naphthaldehyde, 2,4-dihydroxy-1-napthaldehyde, 4-hydroxy-3-methoxy-1-naphthaldehyde, 2-hydroxy-4-methoxy-1-naphthaldehyde, 3-hydroxy-4-methoxy-1-naphthaldehyde, 2,4-dimethoxy-1-naphthaldehyde, 3,4-dimethoxy-1-naphthaldehyde, 4-hydroxy-1-naphthaldehyde, 4-dimethylamino-1-naphthaldehyde, 4-dimethylaminocinnamaldehyde, 2-dimethylaminobenzaldehyde, 2-chloro-4-dimethylaminobenzaldehyde, 4-dimethylamino-2-methylbenzaldehyde, 4-diethylamino-cinnamaldehyde, 4-dibutylamino-benzaldehyde, 4-diphenylamino-benzaldehyde, 4-dimethylamino-2-methoxybenzaldehyde, 4-(1-imidazolyl)-benzaldehyde, piperonal, 2,3,6,7-tetrahydro-1H,5H-benzo[ij]quinolizin-9-carboxaldehyde, 2,3,6,7-tetrahydro-8-hydroxy-1H,5H-benzo[ij]quinolizin-9-carboxaldehyde, N-ethylcarbazol-3-aldehyde, 2-formylmethylene-1,3,3-trimethylindoline, 2-indolaldehyde, 3-indolaldehyde, 1-methylindol-3-aldehyde, 2-methylindol-3-aldehyde, 1-acetylindol-3-aldehyde, 3-acetylindole, 1-methyl-3-acetylindole, 2-(1',3',3'-trimethyl-2-indolinylidene)-acetaldehyde, 1-methylpyrrol-2-aldehyde, 1-methyl-2-acetylpyrrol, 4-pyridinealdehyde, 2-pyridinealdehyde, 3-pyridinealdehyde, 4-acetylpyridine, 2-acetylpyridine, 3-acetylpyridine, pyridoxal, quinoline-3-aldehyde, quinoline-4-aldehyde, antipyrine-4-aldehyde, furfural, 5-nitrofurfural, 2-thenoyl-trifluoroacetone, chromone-3-aldehyde, 3-(5'-nitro-2'-furyl)-acrolein, 3-(2'-furyl)-acrolein, imidazol-2-aldehyde, 1,3-diacetylbenzene, 1,4-diacetylbenzene, 1,3,5-triacetylbenzene, 2-benzoyl-acetophenone, 2-(4'-methoxybenzoyl)-acetophenone, 2-(2'-furoyl)-acetophenone, 2-(2'-pyridoyl)-acetophenone 2-(3'-pyridoyl)-acetophenone, benzylideneacetone, 4-hydroxybenzylideneacetone, 2-hydroxybenzylideneacetone, 4-methoxybenzylideneacetone, 4-hydroxy-3-methoxybenzylideneacetone, 4-dimethylaminobenzylideneacetone, 3,4-methylendioxybenzylideneacetone, 4-pyrrolidinobenzylideneacetone, 4-piperidinobenzylideneacetone, 4-Morpholinobenzylideneacetone, 4-diethylaminobenzylideneacetone, 3-benzylidene-2,4-pentanedione, 3-(4'-hydroxybenzylidene)-2,4-pentanedione, 3-(4'-dimethylaminobenzylidene)-2,4-pentandione, 2-benzylidenecyclohexanone, 2-(4'-hydroxybenzylidene)-cyclohexanone, 2-(4'-dimethylaminobenzylidene)-cyclohexanone, 2-benzylidene-1,3-cyclohexanedione, 2-(4'-hydroxybenzylidene)-1,3-cyclohexanedione, 3-(4'-dimethylaminobenzylidene)-1,3-cyclohexanedione, 2-benzylidene-5,5-dimethyl-1,3-cyclohexanedione, 2-(4'-hydroxybenzylidene)-5,5-dimethyl-1,3-cyclohexanedione, 2-(4'-hydroxy-3-methoxybenzylidene)-5,5-dimethyl-1,3-cyclohexanedione, 2-(4'-dimethylaminobenzylidene)-5,5-dimethyl-1,3-cyclohexanedione, 2-benzylidenecyclopentanone, 2'-(4-hydroxybenzylidene)-cyclopentanone, 2-(4'-dimethylaminobenzylidene)-cyclopentanone, 5-(4-dimethylaminophenyl)penta-2,4-dienal, 5-(4-diethylaminophenyl)penta-2,4-dienal, 5-(4-methoxyphenyl)penta-2,4-dienal, 5-(3,4-dimethoxyphenyl)penta-2,4-dienal, 5-(2,4-dimethoxyphenyl)penta-2,4-dienal, 5-(4-piperidinophenyl)penta-2,4-dienal, 5-(4-morpholinophenyl)penta-2,4-dienal, 5-(4-pyrrolidinophenyl)penta-2,4-dienal, 6-(4-dimethylaminophenyl)hexa-3,5-dien-2-one, 6-(4-diethylaminophenyl)hexa-3,5-dien-2-one, 6-(4-methoxyphenyl)hexa-3,5-dien-2-one, 6-(3,4-dimethoxyphenyl)hexa-3,5-dien-2-one, 6-(2,4-dimethoxyphenyl)hexa-3,5-dien-2-one, 6-(4-piperidinophenyl)hexa-3,5-dien-2-one, 6-(4-morpholinophenyl)hexa-3,5-dien-2-one, 6-(4-pyrrolidinophenyl)hexa-3,5-dien-2-one, 5-(4-dimethylamino-1-naphthyl)penta-3,5-dienal, 2-nitrobenzaldehyde, 3-nitrobenzaldehyde, 4-nitrobenzaldehyde, 4-methyl-3-nitrobenzaldehyde, 3-hydroxy-4-nitrobenzaldehyde, 4-hydroxy-3-nitrobenzaldehyde, 5-hydroxy-2-nitrobenzaldehyde, 2-hydroxy-5-nitrobenzaldehyde, 2-hydroxy-3-nitrobenzaldehyde, 2-fluoro-3-nitrobenzaldehyde, 3-methoxy-2-nitrobenzaldehyde, 4-chloro-3-nitrobenzaldehyde, 2-chloro-6-nitrobenzaldehyde, 5-chloro-2-nitrobenzaldehyde, 4-chloro-2-nitrobenzaldehyde, 2,4-dinitrobenzaldehyde, 2,6-dinitrobenzaldehyde, 2-hydroxy-3-methoxy-5-nitrobenzaldehyde, 4,5-dimethoxy-2-nitrobenzaldehyde, 6-nitropiperonal, 2-nitropiperonal, 5-nitrovanillin, 2,5-dinitrosalicylaldehyde, 5-bromo-3-nitrosalicylaldehyde, 3-nitro-4-formylbenzenesulfonic acid, 4-nitro-1-naphthaldehyde, 2-nitrocinnamaldehyde, 3-nitrocinnamaldehyde, 4-nitrocinnamaldehyde, 9-methyl-3-carbazolaldehyde, 9-ethyl-3-carbazolaldehyde, 3-acetylcarbazole, 3,6-diacetyl-9-ethylcarbazole, 3-acetyl-9-methylcarbazole, 1,4-dimethyl-3-carbazolaldehyde, 1,4,9-trimethyl-3-carbazolaldehyde, 4-formyl-1-methylpyridinium-, 2-formyl-1-methylpyridinium-, 4-formyl-1-ethylpyridinium-, 2-formyl-1-ethylpyridinium-, 4-formyl-1-benzylpyridinium-, 2-formyl-1-benzylpyridinium-, 4-formyl-1,2-dimethylpyridinium-, 4-formyl-1,3-dimethylpyridinium-, 4-formyl-1-methylquinolinium-, 2-formyl-1-methylquinolinium-, 4-acetyl-1-methylpyridinium-, 2-acetyl-1-methylpyridinium-, 4-acetyl-1-methylquinolinium-, 5-formyl-1-methylquinolinium-, 6-formyl-1-methylquinolinium-, 7-formyl-1-methylquinolinium-, 8-formyl-1-methylquinolinium-, 5-formyl-1-ethylquinolinium-, 6-formyl-1-ethylquinolinium-, 7-formyl-1-ethylquinolinium-, 8-formyl-1-ethylquinolinium-, 5-formyl-1-benzylquinolinium-, 6-formyl-1-benzylquinolinium-, 7-formyl-1-benzylquinolinium-, 8-formyl-1-benzylquinolinium, 5-formyl-1-allylquinolinium-, 6-formyl-1-allylquinolinium-, 7-formyl-1-allylquinolinium- and 8-formyl-1-allylquinolinium-, 5-acetyl-1-methylquinolinium-, 6-acetyl-1-methylquinolinium-, 7-acetyl-1-methylquinolinium-, 8-acetyl-1-methylquinolinium, 5-acetyl-1-ethylquinolinium-, 6-acetyl-1-ethylquinolinium-, 7-acetyl-1-ethylquinolinium-, 8-acetyl-1-ethylquinolinium, 5-acetyl-1-benzylquinolinium-, 6-acetyl-1-benzylquinolinium-, 7-acetyl-1-benzylquinolinium-, 8-acetyl-1-benzylquinolinium-, 5-acetyl-1-allylquinolinium-, 6-acetyl-1-allylquinolinium-, 7-acetyl-1-allylquinolinium-, 8-acetyl-1-allylquinolinium-, 9-formyl-10-methylacridinium-, 4-(2'-formylvinyl)-1-methylpyridinium-, 1,3-dimethyl-2-(4'-formylphenyl)-benzimidazolium-, 1,3-dimethyl-2-(4'-formylphenyl)-imidazolium-, 2-(4'-formylphenyl)-3-methylbenzothiazolium-, 2-(4'-acetylphenyl)-3-methylbenzothiazolium-, 2-(4'-formylphenyl)-3-methylbenzoxazolium-, 2-(5'-formyl-2'-furyl)-3-methylbenzothiazolium-2-(5'-formyl-2'-furyl)-3-methylbenzothiazolium-, 2-(5'-formyl-2'-thienyl)-3-methylbenzothiazolium-, 2-(3'-formylphenyl)-3-methylbenzothiazolium-, 2-(4'-formyl-1-naphthyl)-3-methylbenzothiazolium-, 5-chloro-2-(4'-formylphenyl)-3-methylbenzothiazolium-, 2-(4'-formylphenyl)-3,5-dimethylbenzothiazolium-benzenesulfonate, isatin, 1-methyl-isatin, 1-allyl-isatin, 1-hydroxymethyl-isatin, 5-chloro-isatin, 5-methoxy-isatin, 5-nitroisatin, 6-nitroisatin, 5-sulfo-isatin, 5-carboxy-isatin, quinisatin, and 1-methylquinisatin.

9. The composition of claim 1 further comprising at least one compound as component C selected from the group consisting of (a) CH-acid compounds and (b) compounds having primary or secondary amino or hydroxyl groups, selected from aromatic hydroxyl compounds, primary or secondary aromatic amines and nitrogen-containing heterocyclic compounds.

10. The composition of claim 9 wherein the CH-acid compounds of component C are selected from the group consisting of 1,2,3,3-tetramethyl-3H-indolium iodide, 1,2,3,3-tetramethyl-3H-indolium p-toluenesulfonate, 1,2,3,3-tetramethyl-3H-indolium methanesulfonate, 1,3,3-trimethyl-2-methyleneindoline (Fischer Base), 2,3-dimethyl-benzothiazolium iodide, 2,3-dimethylbenzothiazolium p-toluenesulfonate, 2,3-dimethyl-naphtho[1,2-d]thiazolium p-toluenesulfonate, 3-ethyl-2-methyl-naphtho[1,2-d]thiazolium p-toluenesulfonate, rhodanine, rhodanine-3-acetic acid, 1,4-dimethylquinolinium iodide, 1,2-dimethylquinolinium iodide, barbituric acid, thiobarbituric acid, 1,3-dimethylthiobarbituric acid, 1,3-diethyl-thiobarbituric acid, 1,3-diethylbarbituric acid, oxindole, 3-indoxyl acetate, 2-cumaranone, 5-hydroxy-2-cumaranone, 6-hydroxy-2-cumaranone, 3-methyl-1-phenyl-pyrazolin-5-one, indane-1,2-dione, indane-1,3-dione, indan-1-one, benzoylacetonitril, 3-dicyanomethyleneindan-1-one, 2-amino-4-imino-1,3-thiazoline hydrochloride, 5,5-dimethylcyclohexane-1,3-dione, 2H-1,4-benzoxazine-4H-3-one, 3-ethyl-2-methyl-benzoxazolium iodide, 3-ethyl-2-methylbenzothiazolium iodide, 1-ethyl-4-methylquinolinium iodide, 1-ethyl-2-methylquinolinium iodide, 1,2,3-trimethylquinoxalinium iodide, 3-ethyl-2-methylbenzoxazolium p-toluenesulfonate, 3-ethyl-2-methyl-benzothiazolium p-toluenesulfonate, 1-ethyl-4-methyl-quinolinium p-toluenesulfonate, 1-ethyl-2-methylquinolinium p-toluenesulfonate, and 1,2,3-trimethylquinoxalinium p-toluenesulfonate.

11. The composition of claim 9 wherein the primary and secondary aromatic amines of component C are selected from the group consisting of N,N-dimethyl-p-phenylenediamine, N,N-diethyl-p-phenylenediamine, N-(2-hydroxyethyl)-N-ethyl-p-phenylenediamine, N,N-bis-(2-hydroxyethyl)-p-phenylenediamine, N-(2-methoxyethyl)-p-phenylenediamine, 2,3-dichloro-p-phenylenediamine, 2,4-dichloro-p-phenylenediamine, 2,5-dichloro-p-phenylenediamine, 2-chloro-p-phenylenediamine, 2,5-dihydroxy-4-morpholinoaniline, 2-aminophenol, 3-aminophenol, 4-aminophenol, 2-aminomethyl-4-aminophenol, 2-hydroxymethyl-4-aminophenol, o-phenylenediamine, m-phenylenediamine, p-phenylenediamine, 2,5-diaminotoluene, 2,5,-diaminophenol, 2,5-diaminoanisole, 2,5,-diaminophenethol, 4-amino-3-methylphenol, 2-(2,5-diaminophenyl)ethanol, 2,4-diaminophenoxyethanol, 2-(2,5-diaminophenoxy)ethanol, 3-amino-4-(2-hydroxyethyloxy) phenol, 3,4-methylenedioxyphenol, 3,4-methylenedioxyaniline, 3-amino-2,4-dichlorophenol, 4-methylaminophenol, 2-methyl-5-aminophenol, 3-methyl-4-aminophenol, 2-methyl-5-(2-hydroxyethylamino)phenol, 3-amino-2-chloro-6-methylphenol, 2-methyl-5-amino-4-chlorophenol, 5-(2-hydroxyethylamino)-4-methoxy-2-methylphenol, 4-amino-2-hydroxymethylphenol, 2-(diethylaminomethyl)-4-aminophenol, 4-amino-1-hydroxy-2-(2-hydroxyethylaminomethyl)benzene, 1-hydroxy-2-amino-5-methyl-benzene, 1-hydroxy-2-amino-6-methyl-benzene, 2-amino-5-acetamidophenol, 1,3-dimethyl-2,5-diaminobenzene, 5-(3-hydroxypropylamino)-2-methylphenol, 5-amino-4-methoxy-2-methylphenol, N,N-dimethyl-3-aminophenol, N-cyclopentyl-3-aminophenol, 5-amino-4-fluoro-2-methylphenol, 2,4-diamino-5-fluorotoluene, 2,4-diamino-5-(2-hydroxyethoxy)-toluene, 2,4-diamino-5-methylphenetol, 3,5-diamino-2-methoxy-1-methylbenzene, 2-amino-4-(2-hydroxyethylamino)anisole, 2,6-bis-(2-hydroxyethylamino)-1-methylbenzene, 1,3-diamino-2,4-dimethoxybenzene, 3,5-diamino-2-methoxy-toluene, 2-aminobenzoic acid, 3-aminobenzoic acid, 4-aminobenzoic acid, 2-aminophenylacetic acid, 3-aminophenylacetic acid, 4-aminophenylacetic acid, 2,3-diaminobenzoic acid, 2,4-diaminobenzoic acid, 2,5-diaminobenzoic acid, 3,4-diaminobenzoic acid, 3,5-diaminobenzoic acid, 4-aminosalicylic acid, 5-aminosalicylic acid, 3-amino-4-hydroxybenzoic acid, 4-amino-3-hydroxybenzoic acid, 2-aminobenzenesulfonic acid, 3-aminobenzenesulfonic acid, 4-aminobenzenesulfonic acid, 3-amino-4-hydroxybenzenesulfonic acid, 4-amino-3-hydroxynaphthalene-1-sulfonic acid, 6-amino-7-hydroxynaphthalene-2-sulfonic acid, 7-amino-4-hydroxynaphthalene-2-sulfonic acid, 4-amino-5-hydroxynaphthalene-2,7-disulfonic acid, 3-amino-2-naphthoic acid, 3-aminophthalic acid, 5-aminoisophthalic acid, 1,3,5-triaminobenzene, 1,2,4-triaminobenzene, 1,2,4,5-tetraaminobenzene, 2,4,5-triaminophenol, pentaaminobenzene, hexaaminobenzene, 2,4,6-triaminoresorcine, 4,5-diaminopyrocatechol, 4,6-diaminopyrogallol, 1-(2-hydroxy-5-aminobenzyl)-2-imidazolidinone, 4-amino-2((4-[(5-amino-2-hydroxyphenyl)methyl]-piperazinyl)methyl) phenol, 3,5-diamino-4-hydroxypyrocatechol, 1,4-bis-(4-aminophenyl)-1,4-diazacycloheptane, aromatic nitriles, 2-amino-4-hydroxybenzonitrile, 4-amino-2-hydroxybenzonitrile, 4-aminobenzonitrile, 2,4-diaminobenzonitrile, amino compounds with nitro groups, 3-amino-6-methylamino-2-nitropyridine, picramic acid, [8-[(4-amino-2-nitrophenyl)-azo]-7-hydroxy-naphth-2-yl]-trimethylammonium chloride, [8-((4-amino-3-nitrophenyl)-azo)-7-hydroxy-naphth-2-yl]-trimethylammonium chloride (Basic Brown 17), 1-hydroxy-2-amino-4,6-dinitrobenzene, 1-amino-2-nitro-4-[bis-(2-hydroxyethyl)amino]benzene, 1-amino-2-[(2-hydroxyethyl)amino]-5-nitrobenzene (HC Yellow Nr. 5), 1-amino-2-nitro-4-[(2-hydroxyethyl)amino]benzene (HC Red Nr. 7), 2-chloro-5-nitro-N-2-hydroxyethyl-1,4-phenylenediamine, 1-[(2-hydroxyethyl)amino]-2-nitro-4-aminobenzene (HC Red Nr. 3), 4-amino-3-nitrophenol, 4-amino-2-nitrophenol, 6-nitro-o-toluidine, 1-amino-3-methyl-4-[(2-hydroxyethyl)amino]-6-nitrobenzene (HC Violet Nr. 1), 1-amino-2-nitro-4-[(2,3-dihydroxypropyl)amino]-5-chlorobenzene (HC Red Nr. 10), 2-(4-amino-2-nitroanilino) benzoic acid, 6-nitro-2,5-diaminopyridine, 2-amino-6-chloro-4-nitrophenol, 1-amino-2-(3-nitrophenylazo)-7-phenylazo-8-naphthol-3,6-disulfonic acid, disodium salt (acid blue Nr.29), 1-amino-2-(2-hydroxy-4-nitrophenylazo)-8-naphthol-3,6-disulfonic acid, disodium salt (Palatinchrome green), 1-amino-2-(3-chloro-2-hydroxy-5-nitrophenylazo)-8-naphthol-3,6-disulfonic acid, disodium salt (Gallion), 4-amino-4'-nitrostilbene-2,2'-disulfonic acid, disodium salt, 2,4-diamino-3',5'-dinitro-2'-hydroxy-5-methylazobenzene (Mordant brown 4), 4'-amino-4-nitrodiphenylamine-2-sulfonic acid, 4'-amino-3'-nitrobenzophenone-2-carboxylic acid, 1-amino-4-nitro-2-(2-nitrobenzylideneamino)benzene, 2-[2-(diethylamino) ethylamino]-5-nitroaniline, 3-amino-4-hydroxy-5-nitrobenzenesulfonic acid, 3-amino-3'-nitrobiphenyl, 3-amino-4-nitro-acenaphthene, 2-amino-1-nitronaphthalene, 5-amino-6-nitrobenzo-1,3-dioxol, anilines, particularly anilines containing nitro groups, 4-nitroaniline, 2-nitroaniline, 1,4-diamino-2-nitrobenzene, 1,2-diamino-4-nitrobenzene, 1-amino-2-methyl-6-nitrobenzene, 4-nitro-1,3-phenylenediamine, 2-nitro-4-amino-1-(2-hydroxyethylamino)benzene, 2-nitro-1-amino-4-[bis-(2-hydroxyethyl)amino]benzene, 4-amino-2-nitrodiphenylamine-2'-carboxylic acid, 1-amino-5-chloro-4-(2-hydroxyethylamino)-2-nitrobenzene, aromatic anilines or phenols with a further aromatic radical, as illustrated in Formula VI

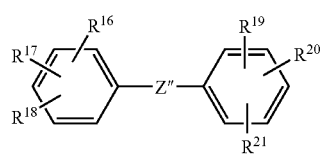

(VI)

in which
R$^{16}$ is a hydroxyl or amino group that can be substituted with $C_1$–$C_6$ alkyl-, $C_1$–$C_6$ hydroxyalkyl-, $C_1$–$C_6$ alkoxy- or $C_1$–$C_6$ alkoxy-$C_1$–$C_6$ alkyl groups,
R$^{17}$, R$^{18}$, R$^{19}$, R$^{20}$ and R$^{21}$ independently of one another are a hydrogen atom, a hydroxyl or an amino group that can be substituted with $C_1$–$C_6$ alkyl-, $C_1$–$C_6$ hydroxyalkyl-, $C_1$–$C_6$ alkoxy-, $C_1$–$C_6$aminoalkyl- or $C_1$–$C_6$ alkoxy-$C_1$–$C_6$ alkyl groups, and
Z" is a direct bond, a saturated or unsaturated carbon chain with 1 to 4 carbon atoms, optionally substituted with hydroxyl groups, a carbonyl-, sulfonyl- or imino group, an oxygen- or sulfur atom, or a group with the Formula VII

(VII)

in which
Q is a direct bond, a CH$_2$— or CHOH group,
Q' and Q" independently of one another are an oxygen atom, an NR$^{22}$ group, in which R$^{22}$ means a hydrogen atom, a $C_1$–$C_6$ alkyl group or $C_1$–$C_6$ hydroxyalkyl group wherein also both groups, together with the remainder of the molecule can form a 5-, 6- or 7-membered ring, the groups O—(CH$_2$)$_p$—NH or NH—(CH$_2$)$_{p'}$—O, in which p and p' are 2 or 3, and
o is a number from 1 to 4,
4,4'-diaminostilbene and its hydrochloride, mono- or di-Na-salt of 4,4'-diaminostilbene-2,2'-disulfonic acid, 4-amino-4'-dimethylaminostilbene and its hydrochloride, 4,4'-diaminodiphenylmethane, 4,4'-diaminodiphenylsulfide, 4,4'-diaminodiphenylsulfoxide, 4,4'-diaminodiphenylamine, 4,4'-diaminodiphenylamine-2-sulfonic acid, 4,4'-diaminobenzophenone, 4,4'-diaminodiphenylether, 3,3',4,4'-tetraaminodiphenyl, 3,3',4,4'-tetraamino-benzophenone, 1,3-bis-(2,4-diaminophenoxy)propane, 1,8-bis-(2,5-diaminophenoxy)-3,6-dioxaoctane, 1,3-bis-(4-aminophenylamino)propane, 1,3-bis-(4-aminophenylamino)-2-propanol, 1,3-bis-[N-(4-aminophenyl)-2-hydroxyethylamino]-2-propanol, N,N-bis-[2-(4-aminophenoxy)ethyl]methyl amine, N-phenyl-1,4-phenylenediamine and bis-(5-amino-2-hydroxyphenyl)methane.

12. The composition of claim 9 wherein the aromatic hydroxyl compounds of component C are selected from the group consisting of 2-, 4-, 5-methylresorcinol, 2,5-dimethylresorcinol, resorcinol, 3-methoxyphenol, pyrocatechol, hydroquinone, pyrogallol, phloroglucine, hydroxyhydroquinone, 2-, 3-, 4-methoxy-, 3-dimethylamino-, 2-(2-hydroxyethyl)-, 3,4-methylenedioxyphenol, 2,4-, 3,4-dihydroxybenzoic acid, -phenylacetic acid, gallic acid, 2,4,6-trihydroxybenzoic acid, -acetophenone, 2-, 4-chlororesorcinol, 1-naphthol, 1,5-, 2,3-, 2,7-dihydroxynaphthalene, 6-dimethylamino-4-hydroxy-2-naphthalenesulfonic acid and 3,6-dihydroxy-2,7-naphthalenesulfonic acid.

13. The composition of claim 9 wherein the nitrogen-containing heterocyclic compounds of component C are selected from the group consisting of 2-aminopyridine, 3-aminopyridine, 4-aminopyridine, 2-amino-3-hydroxypyridine, 2,6-diaminopyridine, 2,5-diaminopyridine, 2-(aminoethylamino)-5-aminopyridine, 2,3-diaminopyridine, 2-dimethylamino-5-aminopyridine, 2-methylamino-3-amino-6-methoxypyridine, 2,3-diamino-6-methoxypyridine, 2,6-dimethoxy-3,5-diaminopyridine, 2,4,5-triaminopyridine, 2,6-dihydroxy-3,4-dimethylpyridine, N-[2-(2,4-diaminophenyl)aminoethyl]-N-(5-amino-2-pyridyl)amine, N-[2-(4-aminophenyl)aminoethyl]-N-(5-amino-2-pyridyl)

amine, 2,4-dihydroxy-5,6-diaminopyrimidine, 4,5,6-triaminopyrimidine, 4-hydroxy-2,5,6-triaminopyrimidine, 2-hydroxy-4,5,6-triaminopyrimidine, 2,4,5,6-tetraaminopyrimidine, 2-methylamino-4,5,6-triaminopyrimidine, 2,4-diaminopyrimidine, 4,5-diaminopyrimidine, 2-amino-4-methoxy-6-methylpyrimidine, 3,5-diaminopyrazole, 3,5-diamino-1,2,4-triazole, 3-aminopyrazole, 3-amino-5-hydroxypyrazole, 1-phenyl-4,5-diaminopyrazole, 1-(2-hydroxyethyl)-4,5-diaminopyrazole, 1-phenyl-3-methyl-4,5-diaminopyrazole, 4-amino-2,3-dimethyl-1-phenyl-3-pyrazolin-5-one (4-aminoantipyrine), 1-phenyl-3-methylpyrazol-5-one, 2-aminoquinoline, 3-aminoquinoline, 8-aminoquinoline, 4-aminoquinaldine, 2-aminonicotinic acid, 6-aminonicotinic acid, 5-aminoisoquinoline, 5-aminoindazole, 6-aminoindazole, 5-aminobenzimidazole, 7-aminobenzimidazole, 5-aminobenzothiazole, 7-aminobenzothiazole, 2,5-dihydroxy-4-morpholino-aniline as well as indole- and indoline derivatives, 4-aminoindole, 5-aminoindole, 6-aminoindole, 7-aminoindole, 5,6-dihydroxyindole, 5,6-dihydroxyindoline, 4-hydroxyindoline and hydroxypyrimidine derivatives and the physiologically compatible salts hereof.

14. The composition of claim 1 wherein the compounds of Formula 1, the compounds of component B and the compounds of component C are each independently present in an amount from 0.03 to 65 mmol based on 100 g of the total composition.

15. The composition of claim 1 comprising a compound according to Formula VIII,

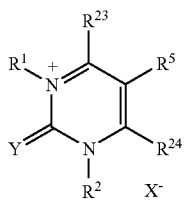

(VIII)

in which
R$^1$, R$^2$, R$^5$, Y and X$^-$ are as defined in claim 1,
R$^{23}$ and R$^{24}$ independently of one another are a hydrogen atom, a C$_1$–C$_6$ alkyl group, a group according to Formula IX,

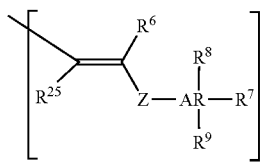

(IX)

in which
R$^6$, R$^7$, R$^8$, R$^9$, AR and Z are as defined according to claim 7,
R$^{25}$ stands for a hydrogen atom or a C$_1$–C$_5$ alkyl group, with the proviso that at least one of the radicals R$^{23}$ and R$^{24}$ stands for a group according to Formula IX.

16. The composition of claim 15 wherein AR is benzene or naphthalene.

17. The composition of claim 15 wherein Z is or a direct bond or vinylene.

18. The composition of claim 15 wherein R$^{25}$ is a hydrogen atom.

19. The composition of claim 15 wherein R$^7$, R$^8$ and R$^9$ independently of one another are a hydrogen atom, a halogen atom, a C$_1$–C$_6$ alkyl group, a hydroxyl group, a C$_1$–C$_6$ alkoxy group, an amino group, a C$_1$–C$_6$ dialkylamino group, a di(C$_2$–C$_6$ hydroxyalkyl)amino group, a di(C$_1$–C$_6$ alkoxy-C$_1$–C$_6$-alkyl)amino group, a C$_1$–C$_6$ hydroxyalkyloxy group, a sulfonyl group, a carboxyl group, a sulfonamide group, a carbamoyl group, a C$_2$–C$_6$ acyl group, an acetyl group, a sulfonic acid group, a sulfonamide group or a nitro group.

20. The composition of claim 15 wherein the compound of Formula VIII is present in an amount from about 0.03 to 65 mmol based on 100 g of the total composition.

21. The composition of claim 1 further comprising a color enhancer selected from the group consisting of piperidine, piperidine-2-carboxylic acid, piperidine-3-carboxylic acid, piperidine-4-carboxylic acid, pyridine, 2-hydroxypyridine, 3-hydroxypyridine, 4-hydroxypyridine, imidazole, 1-methylimidazole, arginine, histidine, pyrrolidine, proline, pyrrolidone, pyrrolidone-5-carboxylic acid, pyrazole, 1,2,4-triazole, piperazidine or their mixtures.

22. The composition of claim 1 further comprising at least one substantive dyestuff, preferably in an amount from 0.01 to 20 wt. %, based on the total composition.

23. The composition of claim 1 further comprising at least one developer component and optionally at least one coupler component as an oxidation dyestuff precursor.

24. The composition of claim 1 further comprising ammonium- or metal salts selected from the group consisting of formates, carbonates, halides, sulfates, butyrates, valeriates, capronates, acetates, lactates, glycolates, tartrates, citrates, gluconates, propionates, phosphates and phosphonates of alkali metals, potassium, sodium or lithium, alkaline-earth metals, magnesium, calcium, strontium or barium, or of aluminum, manganese, iron, cobalt, copper or zinc.

25. The composition of claim 1 further comprising oxidizing agents in an amount of from about 0.01 to 6 wt. %, based on the total weight of the composition.

26. The composition of claim 1 further comprising anionic, zwitterionic or nonionic surfactants.

27. A composition for dyeing keratin-containing fibers comprising at least one compound according to Formula VIII as a substantive dyestuff,

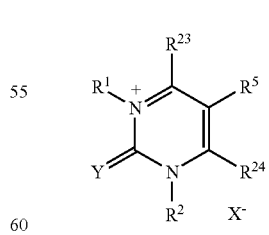

(VIII)

in which
R$^1$, R$^2$, R$^5$, Y and X$^-$ are as defined according to claim 1,
R$^{23}$ and R$^{24}$ independently of one another stand for a hydrogen atom, a C$_1$–C$_6$ alkyl group, a group according to Formula IX,

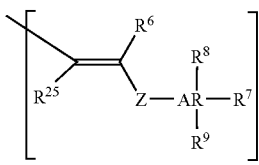

(IX)

in which

R⁶, R⁷, R⁸, R⁹, AR and Z are as defined according to claim 7,

R²⁵ stands for a hydrogen atom or a $C_1$–$C_5$ alkyl group, with the proviso that at least one of the radicals $R^{23}$ and $R^{24}$ is a group according to Formula IX.

28. The composition of claim 27 wherein AR is benzene or naphthalene.

29. The composition of claim 27 wherein Z is or a direct bond or vinylene.

30. The composition of claim 27 wherein $R^{25}$ is a hydrogen atom.

31. The composition of claim 27 wherein $R^7$, $R^8$ and $R^9$ independently of one another are a hydrogen atom, a halogen atom, a $C_1$–$C_6$ alkyl group, a hydroxyl group, a $C_1$–$C_6$ alkoxy group, an amino group, a $C_1$–$C_6$ dialkylamino group, a di($C_2$–$C_6$ hydroxyalkyl)amino group, a di($C_1$–$C_6$ alkoxy-$C_1$–$C_6$-alkyl)amino group, a $C_1$–$C_6$ hydroxyalkyloxy group, a sulfonyl group, a carboxyl group, a sulfonamide group, a carbamoyl group, a $C_2$–$C_6$ acyl group, an acetyl group, a sulfonic acid group, a sulfonamide group or a nitro group.

32. The composition of claim 27 wherein the compound of Formula VIII is present in an amount from about 0.03 to 65 mmol based on 100 g of the total composition.

33. The composition of claim 27 further comprising a color enhancer selected from the group consisting of piperidine, piperidine-2-carboxylic acid, piperidine-3-carboxylic acid, piperidine-4-carboxylic acid, pyridine, 2-hydroxypyridine, 3-hydroxypyridine, 4-hydroxypyridine, imidazole, 1-methylimidazole, arginine, histidine, pyrrolidine, proline, pyrrolidone, pyrrolidone-5-carboxylic acid, pyrazole, 1,2,4-triazole, piperazidine or their mixtures.

34. The composition of claim 27 further comprising at least one substantive dyestuff, in an amount from 0.01 to 20 wt. %, based on the total composition.

35. The composition of claim 27 further comprising at least one developer component and optionally at least one coupler component as an oxidation dyestuff precursor.

36. The composition of claim 27 further comprising ammonium- or metal salts selected from the group consisting of formates, carbonates, halides, sulfates, butyrates, valeriates, capronates, acetates, lactates, glycolates, tartrates, citrates, gluconates, propionates, phosphates and phosphonates of alkali metals, potassium, sodium or lithium, alkaline-earth metals, magnesium, calcium, strontium or barium, or of aluminum, manganese, iron, cobalt, copper or zinc.

37. The composition of claim 27 further comprising oxidizing agents in an amount of from about 0.01 to 6 wt. %, based on the total weight of the composition.

38. The composition of claim 27 further comprising anionic, zwitterionic or nonionic surfactants.

39. A method for dyeing keratin-containing fibers comprising applying to the keratin-containing fibers a composition in accordance with claim 1, leaving the composition on the keratin-containing fibers for a period of time of about 15–30 minutes and subsequently rinsing or washing out said composition with a shampoo.

40. The method of claim 39 further comprising applying component B on the keratin-containing fibers before or after the application of the compound according to Formula I, leaving the resulting mixture on the keratin-containing fibers for a period of time of about 15–30 minutes, and subsequently rinsing or washing out the mixture with a shampoo.

41. The method of claim 39 further comprising adding a bleaching composition or an oxidation colorant to the keratin-containing fibers during a pretreatment prior to adding the composition of claim 1.

* * * * *